US008921324B2

(12) United States Patent
Phiasivongsa et al.

(10) Patent No.: US 8,921,324 B2
(45) Date of Patent: Dec. 30, 2014

(54) CRYSTALLINE PEPTIDE EPOXY KETONE PROTEASE INHIBITORS AND THE SYNTHESIS OF AMINO ACID KETO-EPOXIDES

(71) Applicant: Onyx Therapeutics, Inc., San Francisco, CA (US)

(72) Inventors: Pasit Phiasivongsa, Brentwood, CA (US); Louis C. Sehl, Redwood City, CA (US); William Dean Fuller, San Diego, CA (US); Guy J. Laidig, Menlo Park, CA (US)

(73) Assignee: Onyx Therapeutics, Inc., South San Francisco, CA (US)

(*) Notice: Subject to any disclaimer, the term of this patent is extended or adjusted under 35 U.S.C. 154(b) by 45 days.

(21) Appl. No.: 13/757,148

(22) Filed: Feb. 1, 2013

(65) Prior Publication Data
US 2013/0150290 A1 Jun. 13, 2013

Related U.S. Application Data

(63) Continuation of application No. 12/287,043, filed on Oct. 3, 2008, now Pat. No. 8,367,617.

(60) Provisional application No. 61/008,987, filed on Dec. 20, 2007, provisional application No. 60/997,613, filed on Oct. 4, 2007.

(51) Int. Cl.
| C07K 4/00 | (2006.01) |
| C07K 1/30 | (2006.01) |
| C07C 51/41 | (2006.01) |
| C07K 5/107 | (2006.01) |
| C07D 301/03 | (2006.01) |
| C07D 303/36 | (2006.01) |
| C07D 301/00 | (2006.01) |
| C07K 5/103 | (2006.01) |
| C07K 1/107 | (2006.01) |
| C07C 53/18 | (2006.01) |
| A61K 38/00 | (2006.01) |

(52) U.S. Cl.
CPC .............. *C07K 5/1016* (2013.01); *C07K 1/306* (2013.01); *C07C 51/412* (2013.01); *C07D 301/03* (2013.01); *A61K 38/00* (2013.01); *C07D 303/36* (2013.01); *C07D 301/00* (2013.01); *C07K 5/1008* (2013.01); *C07K 1/1075* (2013.01); *C07C 53/18* (2013.01)
USPC ...................................................... 514/20.1

(58) Field of Classification Search
None
See application file for complete search history.

(56) References Cited

U.S. PATENT DOCUMENTS

| 4,733,665 | A | 3/1988 | Palmaz |
| 4,990,448 | A | 2/1991 | Konishi et al. |
| 5,071,957 | A | 12/1991 | Konishi et al. |
| 5,134,127 | A | 7/1992 | Stella et al. |
| 5,135,919 | A | 8/1992 | Folkman et al. |
| 5,340,736 | A | 8/1994 | Goldberg |
| 5,376,645 | A | 12/1994 | Stella et al. |
| 5,441,944 | A | 8/1995 | Weisz et al. |
| 5,723,492 | A | 3/1998 | Chandrakumar et al. |
| 5,756,764 | A | 5/1998 | Fenteany et al. |
| 5,831,081 | A | 11/1998 | Reuscher |
| 5,874,418 | A | 2/1999 | Stella et al. |
| 6,046,177 | A | 4/2000 | Stella et al. |
| 6,066,730 | A | 5/2000 | Adams et al. |
| 6,075,150 | A | 6/2000 | Wang et al. |
| 6,099,851 | A | 8/2000 | Weisman et al. |
| 6,133,248 | A | 10/2000 | Stella |
| 6,133,308 | A | 10/2000 | Soucy et al. |
| 6,150,415 | A | 11/2000 | Hammock et al. |
| 6,204,257 | B1 | 3/2001 | Stella et al. |
| 6,235,717 | B1 | 5/2001 | Leban et al. |
| 6,294,560 | B1 | 9/2001 | Soucy et al. |
| 6,297,217 | B1 | 10/2001 | Adams et al. |
| 6,410,512 | B1 | 6/2002 | Mundy et al. |
| 6,462,019 | B1 | 10/2002 | Mundy et al. |
| 6,492,333 | B1 | 12/2002 | Mundy |
| 6,548,668 | B2 | 4/2003 | Adams et al. |
| 6,613,541 | B1 | 9/2003 | Vaddi et al. |
| 6,617,309 | B2 | 9/2003 | Tung et al. |
| 6,656,904 | B2 | 12/2003 | Mundy et al. |
| 6,660,268 | B1 | 12/2003 | Palombella et al. |
| 6,699,835 | B2 | 3/2004 | Plamondon et al. |
| 6,740,674 | B2 | 5/2004 | Klimko et al. |
| 6,781,000 | B1 | 8/2004 | Wang et al. |
| 6,794,516 | B2 | 9/2004 | Soucy et al. |
| 6,831,099 | B1 | 12/2004 | Crews et al. |
| 6,838,252 | B2 | 1/2005 | Mundy et al. |

(Continued)

FOREIGN PATENT DOCUMENTS

| EP | 0 411 660 | 2/1991 |
| EP | 1 136 498 | 9/2001 |

(Continued)

OTHER PUBLICATIONS

Demo et al., "Antitumor Activity of PR-171, a Novel Irreversible Inhibitor of the Proteasome," Cancer Research, 67(13):6383-6391 (2007).
Elofsson et al., "Towards subunit-specific proteasome inhibitors: synthesis and evaluation of peptide α, β-epoxyketones," Chemistry & Biology, 6(11):811-822 (1999(.

(Continued)

*Primary Examiner* — Christina Bradley
(74) *Attorney, Agent, or Firm* — Marshall, Gerstein & Borun LLP

(57) ABSTRACT

The invention relates to crystalline peptide keto epoxide compounds, methods of their preparation, and related pharmaceutical compositions. This invention also relates to methods for the preparation of amino acid keto-epoxides. Specifically, allylic ketones are stereoselectively converted to the desired keto epoxides.

15 Claims, 12 Drawing Sheets

(56) References Cited

U.S. PATENT DOCUMENTS

| | | |
|---|---|---|
| 6,838,436 B1 | 1/2005 | Mundy et al. |
| 6,849,743 B2 | 2/2005 | Soucy et al. |
| 6,884,769 B1 | 4/2005 | Mundy et al. |
| 6,902,721 B1 | 6/2005 | Mundy et al. |
| 7,109,323 B2 | 9/2006 | Plamondon et al. |
| 7,189,740 B2 | 3/2007 | Zeldis |
| 7,232,818 B2 | 6/2007 | Smyth et al. |
| 7,388,017 B2 | 6/2008 | Tung et al. |
| 7,417,042 B2 | 8/2008 | Smyth et al. |
| 7,442,830 B1 | 10/2008 | Olhava et al. |
| 7,491,704 B2 | 2/2009 | Smyth et al. |
| 7,531,526 B2 | 5/2009 | Adams et al. |
| 7,687,456 B2 | 3/2010 | Zhou et al. |
| 7,691,852 B2 | 4/2010 | Shenk et al. |
| 7,700,588 B2 | 4/2010 | Merkus |
| 7,737,112 B2 | 6/2010 | Lewis et al. |
| 7,863,297 B2 | 1/2011 | Zeldis |
| 7,968,569 B2 | 6/2011 | Zeldis |
| 8,080,545 B2 | 12/2011 | Shenk et al. |
| 8,080,576 B2 | 12/2011 | Shenk et al. |
| 8,088,741 B2 | 1/2012 | Smyth |
| 8,129,346 B2 | 3/2012 | Smyth et al. |
| 8,198,262 B2 | 6/2012 | Zeldis |
| 8,198,270 B2 | 6/2012 | Smyth et al. |
| 8,198,306 B2 | 6/2012 | Zeldis |
| 8,207,124 B2 | 6/2012 | Smyth et al. |
| 8,207,125 B2 | 6/2012 | Smyth et al. |
| 8,207,126 B2 | 6/2012 | Smyth et al. |
| 8,207,127 B2 | 6/2012 | Smyth et al. |
| 8,207,297 B2 | 6/2012 | Smyth et al. |
| 8,324,174 B2 | 12/2012 | Smyth et al. |
| 8,357,683 B2 | 1/2013 | Shenk et al. |
| 8,367,617 B2 | 2/2013 | Phiasivongsa et al. |
| 8,431,571 B2 | 4/2013 | Shenk et al. |
| 2002/0103127 A1 | 8/2002 | Mundy et al. |
| 2002/0107203 A1 | 8/2002 | Mundy et al. |
| 2002/0111292 A1 | 8/2002 | Mundy et al. |
| 2003/0224469 A1 | 12/2003 | Buchholz et al. |
| 2003/0236223 A1 | 12/2003 | Wagner et al. |
| 2004/0097420 A1 | 5/2004 | Palombella et al. |
| 2004/0106539 A1 | 6/2004 | Schubert et al. |
| 2004/0116329 A1 | 6/2004 | Epstein |
| 2004/0138153 A1 | 7/2004 | Ramesh et al. |
| 2004/0167139 A1 | 8/2004 | Potter |
| 2004/0171556 A1 | 9/2004 | Purandare et al. |
| 2004/0254118 A1 | 12/2004 | He et al. |
| 2004/0266664 A1 | 12/2004 | Crews et al. |
| 2005/0025734 A1 | 2/2005 | Garrett et al. |
| 2005/0101781 A1 | 5/2005 | Agoulnik et al. |
| 2005/0245435 A1 | 11/2005 | Smyth et al. |
| 2005/0256324 A1 | 11/2005 | Laidig et al. |
| 2006/0030533 A1 | 2/2006 | Smyth et al. |
| 2006/0088471 A1 | 4/2006 | Bennett et al. |
| 2006/0128611 A1 | 6/2006 | Lewis |
| 2006/0241056 A1 | 10/2006 | Orlowski et al. |
| 2007/0105786 A1 | 5/2007 | Zhou et al. |
| 2007/0207950 A1 | 9/2007 | Yao et al. |
| 2007/0212756 A1 | 9/2007 | Greene et al. |
| 2008/0090785 A1 | 4/2008 | Smythe et al. |
| 2009/0099132 A1 | 4/2009 | Olhava et al. |
| 2009/0105156 A1 | 4/2009 | Phiasivongsa et al. |
| 2009/0131421 A1 | 5/2009 | Smyth et al. |
| 2009/0156473 A1 | 6/2009 | Schubert |
| 2009/0182149 A1 | 7/2009 | Kawahara et al. |
| 2009/0203698 A1 | 8/2009 | Zhou et al. |
| 2009/0215093 A1 | 8/2009 | Bennett et al. |
| 2010/0144648 A1 | 6/2010 | Shenk et al. |
| 2010/0144649 A1 | 6/2010 | Shenk et al. |
| 2010/0240903 A1 | 9/2010 | Phiasivongsa et al. |
| 2011/0236428 A1 | 9/2011 | Kirk et al. |
| 2012/0077855 A1 | 3/2012 | Phiasivongsa et al. |
| 2012/0088903 A1 | 4/2012 | Phiasivongsa et al. |
| 2012/0101025 A1 | 4/2012 | Smyth et al. |
| 2012/0101026 A1 | 4/2012 | Smyth et al. |
| 2012/0277146 A1 | 11/2012 | Smyth et al. |
| 2012/0329705 A1 | 12/2012 | Smyth et al. |
| 2013/0035295 A1 | 2/2013 | Kirk et al. |
| 2013/0041008 A1 | 2/2013 | Shenk et al. |
| 2013/0053303 A1 | 2/2013 | Shenk et al. |
| 2013/0065827 A1 | 3/2013 | Phiasivongsa |
| 2013/0072422 A1 | 3/2013 | Shenk et al. |
| 2013/0130968 A1 | 5/2013 | Zhou et al. |
| 2013/0150289 A1 | 6/2013 | Phiasivongsa et al. |

FOREIGN PATENT DOCUMENTS

| | | |
|---|---|---|
| WO | WO 91/13904 | 9/1991 |
| WO | WO 94/15956 | 7/1994 |
| WO | WO 95/23797 | 9/1995 |
| WO | WO 95/24914 | 9/1995 |
| WO | WO 96/13266 | 5/1996 |
| WO | WO 96/32105 | 10/1996 |
| WO | WO 98/10779 | 3/1998 |
| WO | WO 00/02548 | 1/2000 |
| WO | WO 00/61167 | 10/2000 |
| WO | WO 01/28579 | 4/2001 |
| WO | WO 03/059898 | 7/2003 |
| WO | WO 2004/089341 | 10/2004 |
| WO | WO 2005/065649 | 7/2005 |
| WO | WO 2005/105827 | 11/2005 |
| WO | WO 2005/111008 | 11/2005 |
| WO | WO 2005/111009 | 11/2005 |
| WO | WO 2006/017842 | 2/2006 |
| WO | WO2006/017842 A | 2/2006 |
| WO | WO 2006/045066 | 4/2006 |
| WO | WO 2006/063154 | 6/2006 |
| WO | WO 2006/086600 | 8/2006 |
| WO | WO 2006/099261 | 9/2006 |
| WO | WO 2006/113470 | 10/2006 |
| WO | WO 2007/021666 | 2/2007 |
| WO | WO 2007/056464 | 5/2007 |
| WO | WO 2007/067976 | 6/2007 |
| WO | WO 2007/149512 | 12/2007 |
| WO | WO 2008/033807 | 3/2008 |
| WO | WO 2008/091620 | 7/2008 |
| WO | WO 2008/140782 | 11/2008 |
| WO | WO 2009/020448 | 2/2009 |
| WO | WO 2009/045497 | 4/2009 |
| WO | WO 2009/051581 | 4/2009 |
| WO | WO 2009/067453 | 5/2009 |
| WO | WO 2009/154737 | 12/2009 |
| WO | WO 2010/036357 | 4/2010 |
| WO | WO 2010/048298 | 4/2010 |
| WO | WO 2010/145376 | 4/2010 |
| WO | WO 2010/108172 | 9/2010 |
| WO | WO 2011/060179 | 5/2011 |
| WO | WO 2011/109355 | 9/2011 |
| WO | WO 2011/123502 | 10/2011 |
| WO | WO 2011/136905 | 11/2011 |

OTHER PUBLICATIONS

Partial International Search Report for PCT/US2008/011443 dated Dec. 9, 2008.

Morris, R.K., Structural Aspects of Hydrates and Solvates in Polymorphism in Pharmaceutical Solids, Ed. H.G. Brittain, marcel Dekker, New York, pp. 125-181 (1999).

Polymorphism in the Pharmaceutical Industry, Ed. Rolf Hilfiker, p. 12 (2006).

Acharyya et al., "Cancer cachexia is regulated by selective targeting of skeletal muscle gene products", JCI, 114:370-378, 2004.

Altun et al., "Effects of PS-341 on the Activity and Composition of Proteasomes in Multiple Myeloma Cells" Cancer Res 65:7896, 2005.

Alves et al. "Diels-alder reactions of alkyl 2H-azirine-3-carboxylates with furans", J. Chem. Soc. Perkin Trans, 1:2969-2976, 2001.

Arastu Kapur et al., "Nonproteasomal targets of the proteasome inhibitors bortezomib and carfilzomib: a link to clinical adverse events", Clin Cancer Res., 17:2734-43, 2011.

Boccadoro et al. "Preclinical evaluation of the proteasome inhibitor bortezomib in cancer therapy", Cancer Cell International, 5(18), Jun. 1, 2005.

(56) References Cited

OTHER PUBLICATIONS

Bogyo et al. "Substrate binding and sequence preference of the proteasome revealed by active-site-directed affinity probes", Chemistry & Biology, 5(6)307-320, Jun. 1998.
Cascio et al., "26S proteasomes and immunoproteasomes produce mainly N-extended versions of an antigenic peptide" EMBO J, 20:2357-2366, 2001.
Diaz-Hernandez et al., "Neuronal Induction of the Immunoproteasome in Huntington's Disease" J. Neurosci., 23:11653-1161, 2003.
Egerer et al., "Tissue-Specific Up-Regulation of the Proteasome Subunit beta5i (LMP7) in Sjogren's Syndrome" Arthritis Rheum 54:1501-8, 2006.
Favit et al. "Prevention of β-Amyloid Neurotoxicity by Blockade of the Ubiquitin-Proteasome Protealytic Pathway", Journ of Neurochemistry, 75(3):1258-1263, 2000.
FDA mulls drug to slow late-stage Alzheimers[Online], [retrieved on Sep. 23, 2003]. Retrieved from the internet.
Figueiredo-Pereira et al., The Antitumor Drug Aclacinomycin A, Which Inhibits the Degradation of Ubiquitinated Proteins, Shows Selectivity for the Chymotrypsin-like Activity of the Bovine Pituitary 20 S Proteasome, The Journal of Biological Chemistry, 271(2):16455-16459, Jul. 1996.
First Vitality (2008, updated) Alzheimer's & Senile Dementia, http://www.1stvitality.co.uk/health/alzheimers/.
Gan et al., "Identification of Cathepsin B as a Mediator of Neuronal Death Induced by A -activated Microglial Cells Using a Functional Genomics Approach", J. Biol. Chem. 279:5565-5572, 2004.
Garcia-Echeverria, "Peptide and Peptide-Like Modulators of 20S Proteasome Enzymatic Activity in Cancer Cells", International J. of Peptide Res. and Ther., 12(1):49-64, Mar. 1, 2006.
Gordon et al, "1207 Results of study PX-171-007 a phase 1b/2 study of carfilzomib, a selective proteasome inhibitor, in patients with selected advanced metastatic solid tumors" Eur. Journ. of Cancer. Supplement, 7(2):122-123, Sep. 2009.
Groettrup et al. "Selective proteasome inhibitors: modulators of antigen presentation?", Drug Discovery Today, 4(2):63-71, Feb. 1999.
Hanada et al, "Epoxomicin, A New Antitumor Agent of Microhial Origin", The Journal of Antihiotics, 45(11):1746-1752, Nove 1992.
Huff, Joel R., "HIV Protease: A Novel Chemotherapeutic Target for AIDS," Journal of Medicinal Chemistry, 34(8):2305-2314, Aug. 1991.
Holbeck et al.,"Analysis of Food and Drug Administration—Approved Anticancer Agents in the NC160 Panel of Human Tumor Cell Lines", Mol Cancer Ther, 9:1451-1460, May 4, 2010.
International Search Report and Written Opinion for PCT/US2010/056395, mailed Mar. 15, 2011, 10 pages.
International Search Report and Written Opinion for PCT/US2011/026629, mailed Jun. 30, 2011, 18 pages.
International Search Report and Written Opinion for PCT/US2011/031436, mailed Nov. 28, 2011, 5 pages.
International Search Report and Written Opinion of the Internatinal Searching Authority for PCT/US2010/028126, mailed Jun. 9, 2010, 13 pages.
Jung et al. "Melatonin in cancer management: progress and promise" Cancer Res., 66(22):9789-9793, 2006.
Khan et al., "Immunoproteasomes Largely Replace Constitutive Proteasomes During an Antiviral and Antibacterial Immune Response in the Liver", J Immunol 5 167:6859-6868, 2001.
Kisselev et al., "Proteasome inhibitirs: from research tools to drug candidates", Chemistry and Bioloty, 8(8):739-758, 2001.
Kijima et al. "Trapoxin, an antitumor cyclic tetrapeptide, is an irreversible inhibitor of mammalian histone deacetylase" J. Biol. Chem. 268(30):22429-22435, 1993.
Kreidenweiss et al. "Comprehensive study of proteasome nhibitors against *Plasmodium falciparum* laboratory strains and field isolates from Gabon", Malar J., 7(187):1-8, 2008.
Kuhn et al.:"Potent activity of carfilzomib, a novel, irreversible inhibitor of the ubiquitin-proteasome pathway, against preclinical models of multiple myeloma", BLOOD, 110(9): 3281-3290 prepublished online: Jun. 25, 2007.

Lecker et al. "Multiple types of skeletal muscle atrophy involve a common program of changes in gene expression", FASEB J 18:39-51, 2004.
Lin et al. "Alteration of substrate and inhibitor specificity of feline immunodeficiency virus protease", J. Virol., 74(10):4710-4720, 2000.
MacAry et al., "Mobilization of MHC class I molecules from late endosomes to the cell surface following activation of CD34-derived human Langerhans cells", PNAS 98:3982-3987, 2001.
Mandel et al., "Neuroprotective Strategies in Parkinson's Disease", CNS Drugs, 2003: 17(10); 729-62.
McGraw-Hill Dictionary of Chemical Terms, 1990, p. 282.
Mishto et al, "Immunoproteasome and LMP2 polymorphism in aged and Alzheimer's disease brains", Neurobiol. Aging, 27:54-66, 2006.
Morissette Sherry, et al. "high-thoughput crystallization: polymorphs, salts, co-crystals and solvates of pharmaceutical solids, advanced drug delivery reivews" Amsterdam, vol. 56, No. 3, 2004 p. 276.
Pivazyan et al., "Inhibition of HIC-1 Protease by a Boron-Modified Polypeptide", Biochem. Pharm. 60:927-936, Mar. 2000.
Schwarz et al., 'The Selective Proteasome Inhibitors Lactacystin and Epoxomicin Can Be Used to Either Up- or Down-Regulate Antigen Presentation at Nontoxic Doses', The Journal of Immunology, 164: 6148-6157. 2000.
Shoemaker, "The NCI60 human tumour cell line anticancer drug screen",Cancer, Nature Reviews, 6:813-823, Oct. 2006.
Sin et al., "Eponymycin analogues: syntheses and use as probes of angiogenesis," Bioorganic & Medicinal Chemistry Letters, 6(8):1209-1217, Aug. 1998.
Stoklosa et al. "Prospects for p53-based cancer therapy", Acta Biochim Pol., 52(2): 321-328, 2005.
Sun et al., inhimbition of acute graft-versus-host disease with retention of graft-versus-tumor effects by the proteasome inhibitor bortezomib: PNAS, 101(21):8120-8125, (2004).
Tawa et al., "Inhibitors of the Proteasome Reduce the Accelerated Proteolysis in Atrophying Rat Skeletal Muscles", JCI 100:197-203, 1997.
Watanabe et al. "Synthesis of boronic acid derivatives of tyropeptin: Proteasome inhibitors", Bioorg. & Med. Chem., 19(8):2343-2345, Apr. 2009.
WebMD "HIV and Aids", www.webmd.com/hiv-aids/guide/sexual-health-aids pp. 1-2, 2009, updated.
Wilson et al., "Novel disease targets and management approaches for diffuse large B-cell lymphoma", Leukemia & Lymphoma, 51 suppl. 1:1-10 abstract only, 2010.
Wipf et al., "Methyl- and (Trifluoromethyl)alkene Peptide Isosteres: Synthesis and Evaluation of Their Potential as .beta.-Turn Promoters and Peptide Mimetics," J. Org. Chem., 1998, 63:6088-6089.
Zhu et al., "3D-QSAR studies of boron-containing dipeptides as proteasome inhibitors with CoMFA and CoMSIA methods", Eur Journ. Med. Chem., 44(4):1486-1499, Apr. 2009.
Zhu et al., "Design, Synthesis and biological evaluation of tripeptide boronic acid proteasome inhibitors", Bioorg & Med. Chem., 17(19):6851-6861, Oct. 2009.
Zollner et al. "Proteasome inhibition reduces superantigen-mediated T cell activation and the severity of psoriasis in a SCID-hu model", J. Clin. Invest., 109(5): 671-679, 2002.
"Definition of Cancer," [Retrieved from] http://www.medterms.com, 1 page [retrieved on Sep. 16, 2005].
Adams et al., "Proteasome Inhibitors: A Novel Class of Potent and Effective Antitumor Agents," Cancer Research, 1999, 59:2615-2622.
Almond et al. "The proteasome: a novel target for cancer chemotherapy" Leukemia, 16(4), 433-443, Apr. 2002.
Argiriadi, "Binding of alkylurea inhibitors to epoxide hydrolase implicates active site tyrosines in substrate activation," J. Biol. Chem., 2000, 275(20):15265-15270.
Bao et al. "PR-39 and PR-11 peptides inhibit ischemia-reperfusion injury by blocking proteasome-mediated IκBα degradation" Am. J. Physiol. Heart Circ. Physiol. 281:H2612-H2618, 2001.
Benedetti et al., "Versatile and Stereoselective Synthesis of Diamino Diol Dipeptide Isosteres, Core Units of Pseudopeptide HIV Protease Inhibitors," J. Org. Chem., 1997, 62:9348-9353.

(56) References Cited

OTHER PUBLICATIONS

Berge et al. "Pharmaceutical Salts", J. Pharm. Sci. 66(1), Jan. 1-19, 1977.
Bernier et al. "A Methionine aminopeptidase-2 Inhibitor, PPI-2458, for the treatment of rheumatoid arthritis", PNAS 101(29):10768-10773, Jul. 20, 2004.
Bogyo et al. "Biochemistry", PNAS 94:6629-6634, 1997.
Bougauchi et al., "Catalytic Asymmetric Epoxidation of .alpha., .beta.-Unsaturated Ketones Promoted by Lanthanoid Complexes," J. Am. Chem. Soc., 1997, 119:2329-2330.
Brinkley, Michael "A Brief Survey of Methods for Preparing Protein Conjugates with Dyes, Haptens, and Cross-Linking Reagents", Bioconjug. Chem 3:2-13, 1992.
Brown et al., "Selective Reductions. 37. Asymmetric Reduction of Prochiral Ketones with .beta,-(3-Pinanyl)-9- borabicyclo[3.3.1]nonane," J. Org. Chem., 1985, 50:1384-1394.
Caira, "Crystalline Polymorphism of Organic Compounds," Topics in Current Chemistry, 1998, 198:163-208.
Ciechanover, "The Ubiquitin-Proteasome Proteolytic Pathway," Cell, 1994, 79:13-21.
Cohen, "AIDS Mood Upbeat-For a Change," Science, 1995, 267:959-960.
Collins, Tucker, "Endothelial nuclear factor- κB and the initiation of the atherosclerotic lesion", Lab. Invest. 68(5), 499-508, 1993.
Concise Encyclopedia Chemistry, 1993, p. 490.
Corey et al., "A General, Catalytic, and Enantioselective Synthesis of .alpha.-Amino Acids," J. Am. Chem. Soc., 1992, 114:1906-1908.
Corey et al., "Highly Enantioselective Borane Reduction of Ketones Catalyzed by Chiral Oxazaborolidines. Mechanism and Synthetic Implications," J. Am. Chem. Soc., 1987, 109:5551-5553.
Craiu et al. "Lactacystin and clasto-lactacystin β-lactone modify multiple proteasome β-subunits and inhibit intracellular protein degradation and major hisotcompatibility complex class I antigen presentation" J. of Biol. Chem. 272(20), 13437-13445, May 16, 1997.
Datta et al., "A Stereoselective Route to Hydroxyethylamine Dipeptide Isosteres," J. Am. Chem. Soc., 2000, 65:7609-7611.
Demo et al., "Antitumor Activity of PR-171, a Novel Irreversible Inhibitor of the Proteasome," Cancer Research, 2007, 67(13):6383-6391.
Dess et al., "A Useful 12-I-5 Triacetoxyperiodinane (the Dess-Martin Periodinane) for the Selective Oxidation of Primary or Secondary Alcohols and a Variety of Related 12-I-5 Species," J. Am. Chem. Soc., 1991, 113:7277-7287.
Dess et al., "Readily Accessible 12-I-5 Oxidant for the Conversion of Primary and Secondary Alcohols to Aldehydes and Ketones," J. Org. Chem., 1983, 48:4155-4156.
Dobler, "Total synthesis of (+)-epopromycin B and its analogues-studies on the inhibition of cellulose biosynthesis," Tetrahedron Letters, 2001, 42(2):215-218.
Elofsson et al., "Towards subunit-specific proteasome inhibitors: synthesis and evaluation of peptide .alpha.',.beta.'-epoxyketones," Chemistry & Biology, 1999, 6:811-822.
Fenteany et al. "A β-lactone related to lactacystin induces neurite outgrowth in a neuroblastoma cell line and inhibits cell cycle progression in an osteosarcoma cell line", PNAS 91:3358-3362, Apr. 1994.
Fox et al. "Organic Chemistry", Publisher: Jones & Bartlett Pub, Published Jun. 15, 2004, Sec. 5-6, pp. 177-178, ISBN-10: 0763721972, ISBN-13: 9780763721978.
Gao et al. "Inhibition of ubiquitin-proteasome pathway—mediated IκBα degradation by a naturally occurring antibacterial peptide" J. Clin, Invest. 106:439-448, 2000.
Garrett et al., "Selective inhibitors of the osteoblast proteasome stimulate bone formation in vivo and in vitro," J Clinical Investigation, 2003, 111:1771-1782.
Golub et al., "Molecular Classification of Cancer: Class Discovery and Class Prediction by Genes Expression Monitoring," Science, 1999, 286:531-537.
Gonzales et al. "Pain relief in chronic pancreatitis by pancreaticojejunostomy. An institutional experience" Arch. Med. Res. 28(3), 387-390, 1997.
Graz University of Technology, "Database of Fluorescent Dyes Properties and Applications" WWW.Fluorophonres.org, 33 pgs, Exhibit B to response filed with US Patent office on Sep. 16, 2008 for U.S. Appl. No. 11/254,541 (now abandoned).
Green et al. "Protective Groups in Organic Synthesis", 2nd ed., Wiley & Sons, Inc., New York (1991).
Griffith et al., "Molecular recognition of angiogenesis inhibitors fumagillin and ovalicin by methionine aminopeptidase", PNAS 95:15183-15188, Dec. 1998.
Groll et al., "Crystal Structure of Epoxomicin:20S Proteasome Reveals a Molecular Basis for Selectivity of r¢,â¢-Epoxyketone Proteasome Inhibitors," J. Am. Chem. Soc. 2000, 122:1237-1238.
Gura, "Systems for Identifying New Drugs Are Often Faulty," Science, Nov. 7, 1997, 278(5340):1041-1042.
Hanson et al., "Synthesis of New Dipeptide Analogues Containing Novel Ketovinyl and Hydroxyethylidene Isosteres via Grignard Addition to Chiral .alpha.-Amino Aldehydes," J. Org. Chem., 1985, 50:5399-5401.
Harding et al., "Novel Dipeptide Aldehydes Are Proteasome Inhibitors and Block the MHC-1 Antigen-Processing Pathway," J. Immunology, 1995, 155:1767-1775.
Hardy, "The secret life of the hair follicle," Trends in Genetics, 1992, 8:55-61.
Harris et al. "Effects of transforming growth factor βon bone nodule formation and expression of bone morphogenetic protein 2, osteocalcin, osteopontin, alkaline phosphatase, and type I collagen mRNA in long-term cultures of fetal rat calvarial osteoblasts", J. Bone Miner. Res. 9(6), 855-863, 1994.
Hawley's Condensed Chemical Dictionary, 1993, p. 594.
Haugland, Rosaria "Coupling of Monoclonal Antibodies with Fluorophores", Methods Mol. Biol. 45, 205-221, 1995.
Hilfiker, Ed., Polymorphism in the Pharmaceutical Industry, 2006, pp. 12-15.
Hoffman et al., "Highly Stereoselective Syntheses of syn- and anti-1,2-Amino Alcohols," J. Org. Chem., 2002, 67:1045-1056.
Iqbal et al. "Potent Inhibitors of Proteasome", J. Med Chem. 38:2276-2277, 1995.
Iqbal et al., "Potent .alpha.-ketocarbonyl and boronic ester derived inhibitors of proteasome," Bioorganic & Medicinal Chemistry Letters, 1996, 6:287-290.
Jacobsen et al., "Asymmetric Dihydroxylation via Ligand-Accelerated Catalysis," J. Am. Chem. Soc., 1988, 110:1968-1970.
Jain, "Delivery of Molecular Medicine to Solid Tumors," Science, 1996, 271(5252):1079-1080.
Jones et al., "Total Synthesis of the Immunosuppressant (−)-FK-506," J. Am. Chem. Soc., 1989, 111:1157-1159.
Kessler et al. "Extended peptide-based inhibitors efficiently target the proteasome and reveal overlapping specificities of the catalytic β-subunits", Chem & Biol. 8(9), 913-929, Aug. 8, 2001
Kim et al., "Proteasome inhibition by the natural products epoxomicin and dihydroeponemycin: insights into specificity and potency," Bioorganic & Medicinal Chemistry Letters, 1999, 9:3335-3340.
Kojima et al., "Two-way cleavage of β-amyloid protein precursor by multicatalytic proteinase" Fed. Eur. Biochem. Soc. 304:57-60, Jun. 1992.
Koong et al. Hypoxia causes the activation of nuclear factor- kB through the phosphorylation of IκBα on tyrosine residues1, Cancer Research, 54:1425-1430, Mar. 15, 1994.
Koong et al. Hypoxic activation of nuclear factor- κB is mediated by a Ras and Raf signaling pathway and does not involve MAP kinase (ERK1 or ERK2)1, Cancer Research, 54:5273-5279, Oct. 15, 1994.
Krise et al. "A Novel Prodrug Approach for Tertiary Amines: Synthesis and Preliminary Evaluation of N-Phosphonooxyrnethyl Prodrugs", J. Med. Chem. 42:3094-3100, 1999.
Kumatori et al., "Abnormally high expression of proteasomes in human leukemic cells," Proc. Natl. Acad. Sci. USA, 1990, 87:7071-7075.

(56) References Cited

OTHER PUBLICATIONS

Lala et al., "Role of notric oxide in tymor progression: Lessons from experimental tumors," Cancer and Metastasis Reviews, 1998, 17:91-106.
Liang et al., "Synthesis of Cryptophycin 52 Using the Sharpless Asymmetric Dihydroxylation: Diol to Epoxide Transformation Optimized for a Base-Sensitive Substrate," J. Am. Chem. Soc., 2000, 65:3143-3147.
Loftsson et al., "Pharmaceutical Applications of Cyclodextrins. 1. Drug Solubilization and Stabalization," Journal of Pharmaceutical Sciences, American Pharmaceutical Association, 85(10):1017-1025 (1996).
Marx et al., "Reactivity-Selectivity in the Swern Oxidation of Alcohols Using Dimethyl Sulfoxide-Oxalyl Chloride," J. Org. Chem., 1984, 49:788-793.
Meng et al., "Eponemycin Exerts Its Antitumor Effect through the Inhibition of Proteasome Function," Cancer Research, 1999, 59:2798-2801.
Meng et al., "Epoxomicin, a potent and selective proteasome inhibitor, exhibits in vivo antiinflamatory activity," Proc. Natl. Acad. Sci. USA, 1999, 96:10403-10408.
Molecular biology and biotechnology a comprehensive desk reference: Edited by R A Meyers. pp. 658-664. VCH, Weinheim, Germany, 1995, DM89 ISBN 1-56081-925-1.
Molecular Probes, Inc., "Introduction to Fluorescence techniques", invitrogen detection technologies, 11 pgs, Molecular Probes, Inc. (2007), Exhibit A to response filed with US Patent Office on Sep. 16, 2008 for U.S. Appl. No. 11/254,541 (now abandoned).
Morris, "Structural Aspects of Hydrates and Solvates in Polymorphism in Pharmaceutical Solids," Polymorphism in Pharmaceutical Solids, 1999, Ed. H.G. Nbrittain, Marcel Dekker, New York, pp. 125-181.
Myung et al., "Lack of Proteasome Active Site Allostery as Revealed by Subunit-Specific Inhibitors," Molecular Cell, 2001, 7(2):411-420.
Myung et al., "The Ubiquitin-Proteasome Pathway and Proteasome Inhibitors," Medicinal Research Reviews, 2001, 21(4):245-273.
Nemoto et al., "Catalytic Asymmetric Epoxidation of Enones Using La-BINOL-Triphenylarsine Oxide Complex; Structural Determination of the Asymmetric Catalyst," J. Am. Chem. Soc., 2001, 123:2725-2732.
Oishi et al., "Diastereoselective synthesis of new psi '(E)-CH=CMel- and psi '(Z)-CH=CMel- type alkene dipeptide isosteres by organocopper reagents and application to conformationally restricted cyclic RGD peptidomimetics," J. Org. Chem., 2002, 67:6162-6173.
Overkleeft et al. "Solid phase synthesis of peptide vinyl sulfone and peptide expoxyketone proteasome inhibitors", Tetrahedron Letters, 41(32), 6005-6009, 2000.
Palombella et al., "The Ubiquitin-Proteasome Pathway Is Required for Processing the NF-.kappa.B1 Precursor Protein and the Activation of NF-.kappa.B," Cell, 1994, 78:773-785.
Paugam et al., "Characterization and role of protozoan parasite proteasomes," Trends Parasitol., 2003, 19:55-59.
Pye et al. "Proteasome inhibition ablates activation of NF-κB in myocardial reperfusion and reduces reperfusion of injury", Am. J. Physiol. Heart Circ. Physiol 284:H919-H926, 2003.
Qureshi et al., "The Proteasome as a Lipopolysaccharide-Binding Protein in Macrophages: Differential Effects of Proteasome Inhibition on Lipopolysaccharide-Induced Signaling Events," J. Immunology, 2003, 171:1515-1525.
Reidlinger et al. "Catalytic Properties of 26 S and 20 S Proteasomes and Radiolabling of MB 1, LMP7, and C7 Subunits Associated with Trypsin-like and Chymotrypsin-like Activities", J. of Biol Chem. 272(40), 24899-24905, May 27, 1997.
Safadi et al., "Phosphoryloxymet hyl Carbamates and Carbonates-Novel Water-Soluble Prodrugs for Amines and Hindered Alcohols", Pharmaceutical Research 10(9), 1350-1355, Mar. 2, 1993.
Shao et al., "A New Asymmetric Synthesis of .alpha.-Methylcysteines via Chiral Aziridines," J. Org. Chem., 1995, 60:790-91.

Sharpless et al., "High Stereo- and Regioselectivities in the Transition Metal Catalyzed Epoxidations of Olefmic Alcohols by tert-Butyl Hydroperoxide," J. Am. Chem. Soc., 1973, 95:6136-6137.
Simsek et al. "Hepatitis B Virus Large and Middle Glycoproteins Are Degraded by a Proteasome Pathway in Glucosidase-Inhibited Cells but Not in Cells with Functional Glucosidase Enzyme", J. Virol. 79(20), 12914-12920, Oct. 2005.
Sin et al., "Total synthesis of the potent proteasome inhibitor epoxomicin; a useful tool for understanding proteasome biology," Bioorganic & Medicinal Chemistry Letters, 1999, 9:2283-2288.
Spaltenstein et al., "Design and Synthesis of Novel Protease Inhibitors, Tripeptide .alpha.',.beta.'-Epoxyketones as Nanomolar Inactivators of the Proteasome," Tetrahedron Letters, 1996, 37:1343-1346.
Stein et al., "Kinetic Characterization of the Chymotryptic Activity of the 20S Proteasome," Biochemistry, 1996, 35:3899-3908.
Strickley, Robert G., "Solubilizing Excipients in Oral and Injectable Formulations," Pharmaceutical Research, 21(2):201-230 (2004).
Szalay et al. "Ongoing coxsackievirus myocarditis is associated with increased formation and activity of myocardial immunoproteaseomes", Am. J. Pathol. 168(5), 1542-1552, May 2006.
Terato et al. "Induction of arthritis with monoclonal antibodies to collagen1" J. Immunol, 148(7), 2103-2108, Apr. 1, 1992.
Thanos et al., "NF-.kappa.B: A Lesson in Family Values," Cell, 1995, 80:529-532.
Thompson., "Cyclodextrins-enabling excipients: their present and future use in pharmaceuticals," Critical Reviews in Therapeutic Drug Carrier Systems, 14(1):1-104 (1997).
Tong, Wei-Qin (Tony), "Applications of Complexation in the Formulation of Insoluble Compounds," R. Liu, Ed., pp. 111-139 (2000).
Traenckner et al,, "A proteasome inhibitor prevents activation of NF-,kappa.B and stabilizes a newly phosphorylated form of I.kappa.B-.alpha. that is still bound to NF-.kappa.B," EMBO J., 1994, 13:5433-5441.
Tu et al., "An Efficient Assymettric Epoxidation Method for trans-Olefins Mediated by a Fructose-Derived Ketone," J. Am, Chem. Soc., 1996, 118:9806-9807.
Vogel's textbook of practical organic chemistry, 5th Ed. See p. 135, "2.20 Recrystallisation Techniques" and p. 141, 2nd paragraph onwards, 1996.
Voskoglou-Nomikos, "Clinical Predictive Value of the in Vitro Cell Line, Human Xenograft, and Mouse Allograft Preclinical Cancer Models," Clin Cancer Res., 2003, 9(11):4227-4239.
Wang et al., "A New Type of Ketone Catalyst for Asymmetric Epoxidation," J. Org. Chem., 1997, 62:8622-8623.
Wipf et al., "Methyl- and (Trifluorornethyl)alkene Peptide lsosteres: Synthesis and Evaluation of Their Potential as .beta.-Turn Promoters and Peptide Mimetics," J. Org. Chem., 1998, 63:6088-6089.
Xu et al. "Mutations in the tumor suppressors Smad2 and Smad4 inactivate transforming growth factor βsignaling by targeting Smads to the ubiquitin-proteasome pathway", PNAS 97(9), 4820-4825, Apr. 25, 2000.
Yu et al, "The Ubiquitin-Proteasome System Facilitates the Transfer of Murine Coronavirus from Endosome to Cytoplasm during Virus Entry", J. Virol. 79(1), 644-648, Jan. 2005.
Zhou et al., "Design and Synthesis of an Orally Bioavailable and Selectrive Peptide Epoxyketone Proteasome Inhibitor (PR-047)," J. Med. Chem., 2009, 52 (9):3028-3038.
Elliott et al., "The Proteasome a New Target for Novel Drug Therapies," Am J Clin Pathol., 2001, 116:637-646.
Le Blanc et al., "Growth in Vivo and Prolongs Survival in a Murine Model Proteasome Inhibitor PS-341 Inhibits Human Myeloma Cell," Cancer Research, 2002, 62:4996-5000, Published online Sep. 1, 2002.
Adams, "The development of proteasome inhibitors as anticancer drugs," Cancer Cell, May 2003, 5:417-421.
Adams, Cancer Drug Discovery and Development, Protease Inhibitors in Cancer Therapy, 2004. Human Press, Chapter 20, Phase I trials, pp. 271-282.
Rossi et al., "Proteasome inhibitors in cancer therapy: death by indigestion," Cell Death and Differentiation, 2005, as:1255-1257.

(56) References Cited

OTHER PUBLICATIONS

Roccaro et al., "Selective inhibition of chymotrypsin-like activity of the immunoproteasome and constitutive proteasome in Waldenström macroglobulimia," Blood, 2010, 115:4051-4060.
Orlowski and Kuhn, "Proteasome Inhibitors in Cancer Therapy: Lessons from the First Decade," Clin. Canc. Res., 2008, 14:1649-165.
Center for Drug Evaluation and Research, Application No. 21-602, Medical Review, Clinical NDA Review, "NDA 21-602 VELCADE™ (bortexomib) for injection," Clinical Review, 1-47, 2003.
Center for Drug Evaluation and Research, Application No. 21-602, Medical Review, Clinical NDA Review, "NDA 21-602 VELCADE™ (bortexomib) for injection," Clinical Review, 81-125, 2003.
Center for Drug Evaluation and Research, Application No. 21-602, Medical Review, Clinical, NDA Review, "NDA 21-602 VELCADE™ (bortexomib) for injection," Clinical Review, 1-34, 2003.
Orlowski et al., "Phase I Trial of the Proteasome Inhibitor PS-341 in Patients With Refractory Hematologic Malignancies," Journal of Clinical Oncology, 2002, 20(22):4420-4427.
European Search Report, EP 08 16 4241, completed Jan. 22, 2009, 5 pages.
International Search Report and Written Opinion for corresponding PCT Application No. PCT/US2005/016335, mailed Jan. 2, 2006, 17 pgs.
International Preliminary Report on Patentability for corresponding PCT Application No. PCT/US2005/016335, issued Nov. 14, 2006, 11 pgs.
International Search Report and Written Opinion for corresponding PCT Application No. PCT/US2005/012740, mailed Jan. 9, 2006, 16 pgs.
International Preliminary Report on Patentability for corresponding PCT Application No. PCT/US2005/012740, issued Oct. 19, 2006, 11 pgs.
Authorized Officer M. Kollmannsberger, International Search Report and Written Opinion for PCT/US2007/014427, mailed Dec. 3, 2007, 12 pages.
Authorized Officer M. Kollmannsberger, International Preliminary Report on Patentability PCT/US2007/014427, issued Dec. 22, 2008, 8 pages.
European Search Report, EP 09 00 6228, completed Aug. 25, 2009, 7 pages.
Authorized Officer A. Schleifenbaum, International Search Report and Written Opinion of the International Searching Authority for PCT/US2008/005997, mailed Nov. 7, 2008, 8 pages.
Authorized Officer Philippe Becamel, International Preliminary Report on Patentability for PCT/US2008/005997, issued Nov. 10, 2009, 7 pages.
Authorized Officer Grant McNeice, International Search Report for PCT/US2009/061498, mailed Dec. 10, 2009, 5 pages.
Authorized Officer Sonya James, International Search Report and Written Opinion of the International Searching Authority for PCT/US2006/043503, mailed Feb. 19, 2007, 17 pages.
Authorized Officer Dorothée Mülhausen, International Search Report and Written Opinion of the International Searching Authority for PCT/US2006/043503, mailed Feb. 19, 2007, 17 pages.
Authorized Officer Marc Kloth, International Search Report and Written Opinion of the Internatinal Searching Authority for PCT/US2010/028126, mailed Jun. 9, 2010, 13 pages.
Partial International Search Report for PCT/US2008/011443, dated Dec. 9, 2008, 6 pages.
Authorized Officer M. Groenendijk, International Search Report and Written Opinion of the International Searching Authority for PCT/US2005/028246, mailed Jan. 19, 2006, 11 pages.
Authorized Officer Yoshiko Kuwahara, International Preliminary Report on Patentability for PCT/US2005/028246, issued Feb. 6, 2007, 8 pages.
Authorized Officer D. Grassi, International Search Report and Written Opinion of the International Searching Authority for PCT/US2005/017000, mailed Feb. 3, 2006, 12 pages.

Authorized Beate Giffo-Schmitt, International Preliminary Report on Patentability for PCT/US2005/017000, issued Nov. 21, 2006, 12 pages.
Authorized Officer M. Groenendijk, International Search Report and Written Opinion of the International Searching Authority for PCT/US2005/037966, mailed Jan. 24, 2006, 17 pages.
Authorized Officer Dorothée Mülhausen, International Preliminary Report on Patentability for PCT/US2005/037966, issued Apr. 24, 2007, 12 pages.
Authorized Officer M. Groenendijk, International Search Report and Written Opinion of the International Searching Authority for PCT/US2005/044451, mailed May 2, 2006, 12 pages.
Authorized Officer Philippe Becamel, International Preliminary Report on Patentability for PCT/US2005/044451, issued Jun. 13, 2007, 8 pages.
Authorized Officer Sonya James, International Search Report and Written Opinion of the International Searching Authority for PCT/US2008/011443, mailed Mar. 25, 2009, 16 pages.
Authorized Officer Athina Nickitas-Etienne, International Preliminary Report on Patentability for PCT/US2008/011443, issued Apr. 7, 2010, 12 pages.
Bis et al. "Defining & Addressing Solid-State Risks After the Proof-of-Concept Stage of Pharmaceutical evelopment," Drug Development & Delivery, pp. 32-34, 2011.
Blackburn et al., "Characterization of a new series of non-covalent proteasome inhibitors with exquisite potency and selectivity for the 2OS β5-subunit," *Biochem J.*, 2010, 430:461-476.
Brittain et al. "Physical Characterization of Pharmaceutical Solids," Pharmaceutical Research, 8(8):963-973, 1991.
Byrn et al., "Pharmaceutical Solids: A Strategic Approach to Regulatory Considerations," Pharma. Res., 1995, 12(7):945-954.
Cancer [online], [retrieved on Jun. 7, 2007] Retrieved from the Internet, URL: http://www.nlm.nih.gov/medlineplus/cancer.html.
Dasmahapatra et al., "Carfilzomib Interacts Synergistically with Histone Deacetylase Inhibitors in Mantle Cell Lymphoma Cells In Vitro and In Vivo," Mol. Cancer. Ther., 2011, 10:1686-1697.
Dimopoulos et al. "Lenalidomide plus Dexamethasone for Relapsed or Refractory Multiple Myeloma," N. Engl J Med., 2007, 357(21):2123-2132.
Dinger et al., "Some Crystal Growing Tips," 2006, http://xray.chem.ufl.edu/growing%20tips.htm. 3 pages.
European Search Report, EP 09822636.8, dated Aug. 1, 2012, 6 pages.
Extended European Search Report, EP 12189466.1, dated Jul. 23, 2013, 10 pages.
Extended European Search Report, EP 13167148.9, dated Aug. 2, 2013, 7 pages.
Gennaro, "Remington: Practice of the Science of Pharmacy," 19th Edition, 1995, Mack Publishing Company, Chapter 83, pp. 1447-1462.
International Preliminary Report on Patentability for PCT/US2010/056395, mailed May 24, 2012, 8 pages.
International Preliminary Report on Patentability for PCT/US2011/026629, dated Sep. 4, 2012, 11 pages.
International Preliminary Report on Patentability PCT/US2009/061498, dated May 5, 2011, 9 pages.
International Preliminary Report on Patentability PCT/US2011/031436, dated Oct. 9, 2012, 5 pages.
International Search Report and Written Opinion of the International Searching Authority for PCT/US2012/055127, mailed Dec. 18, 2012, 10 pages.
International Search Report and Written Opinion of the International Searching Authority for PCT/US2013/040127, mailed Oct. 22, 2013, 15 pages.
Ivanisevic et al., "Uses of X-Ray Powder Diffraction in the pharmaceutical Industry," Pharmaceutical Sciences Encyclopedia: Drug Discovery, Development, and Manufacturing, Edited by Shayne C. Gad, 2010, pp. 1-42.
Lee and Goldberg, "Proteasome inhibitors: valuable new tools for cell biologists," Trends in Cell Biol., Oct. 1988, 8:397-403.
Luke et al., "Review of the Basic and Clinical Pharmacology of Sulfobutylether-β-0Cyclodextrin (SBECD)," J. of Pharmaceutical Sciences, 2010, 99:3291-3301.

(56) References Cited

OTHER PUBLICATIONS

Min et al., ""Bortezomib in Combination with Conventional Chemotherapeutic Agents for Multiple Myeloma Compared with Bortezomib alone,""Japanese Journal of Clinical Oncology, 2007, 37(12):961-968.

Muchamuel et al., "A selective inhibitor of the immunoproteasome subunit NMP7 blocks cytokine production and attenuates progression of experimental arthritis," Nature Med., Jun. 2009, 15:781-787.

Newman et al. "Solid-state analysis of the active pharmaceutical ingredient in drug products," Drug Discovery Today, 8(19):898-905, 2003.

Paoluzzi et al., "Targeting Bcl-2 family members with the BH3 mimetic AT-101 markedly enhances the therapeutic effects of chemotherapeutic agents in in vitro and in vivo models of B-cell lyphoma", Blood, 111(11):5350-5358, Jun. 2008.

Polymorphism in Pharmaceutical Solids, edited by Brittain, 1999, Marcel Dekker Inc., p. 228-229, 236.

Raw et al. "Regulatory considerations of pharmaceutical solid polymorphism in Abbreviated New Drug Applications (ANDAs)," Advanced Drug Delivery Reviews 56:397-414, 2004.

Rouhi, Chemical & Engineering News, Feb. 24, 2004, p. 32-35.

Shah et al. "Analytical Techniques for Quantification of Amorphous/ Crystalline Phases in Pharmaceutical Solids," Journal of Pharm. Sciences, 95(8):1641-1665, 2006.

Singhal et al. "Drug polymorphism and dosage form design: a practical perspective" Advanced Drug Delivery Reviews, 56:335-347, 2004.

Stahl and Wermuth, Handbook of Pharmaceutical Salts: Properties, Selection, and Use, 2002, pp. 198-200.

U.S. Pharmacopia #23, National Formulary #18 (1995), p. 1843-1844.

Yang et al., "Pharmacokinetics, Pharmacodynamics, Metabolism, Distribution, and Excretion of Carfilzomib in Rats," Drug Metabol. And Disposition, 2011, 39:1873-1882.

CRYSTALLINE PEPTIDE EPOXY KETONE PROTEASE INHIBITORS AND THE SYNTHESIS OF AMINO ACID KETO-EPOXIDES

RELATED APPLICATIONS

This application is a continuation of U.S. application Ser. No. 12/287,043, filed Oct. 3, 2008, which claims the benefit of U.S. Provisional Application Ser. No. 60/997,613, filed Oct. 4, 2007, and U.S. Provisional Application Ser. No. 61/008,987, filed Dec. 20, 2007; each of these earlier filed applications is incorporated herein by reference in its entirety.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasomes thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECL1), which replace their normal counterparts, X, Y and Z respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

What is needed are improved compositions and methods for preparing and formulating proteasome inhibitor(s).

SUMMARY OF THE INVENTION

The invention generally relates to the synthesis of proteasome inhibitors and the preparation and purification of intermediates useful therefor.

One aspect of the invention relates to crystalline compounds having a structure of Formula (I) or a pharmaceutically acceptable salt thereof,

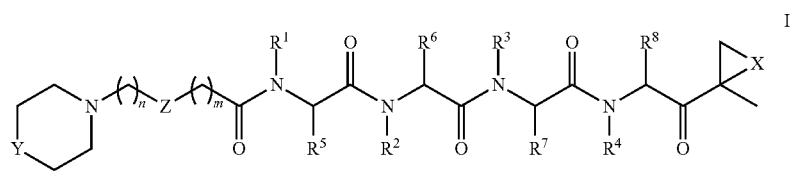

wherein
X is O, NH, or N-alkyl, preferably O;
Y is NH, N-alkyl, O, or $C(R^9)_2$, preferably N-alkyl, O, or $C(R^9)_2$;
Z is O or $C(R^9)_2$, preferably $C(R^9)_2$;
$R^1$, $R^2$, $R^3$, and $R^4$ are hydrogen;
each of $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether, preferably $R^5$, $R^6$, $R^7$, and $R^8$ are independently selected from $C_{1-6}$alkyl, $C_{1-6}$hydroxyalkyl, and $C_{1-6}$aralkyl and each $R^9$ is hydrogen, more preferably, $R^6$ and $R^8$ are independently $C_{1-6}$alkyl, $R^5$ and $R^7$ are independently $C_{1-6}$aralkyl and each $R^9$ is H;
m is an integer from 0 to 2; and
n is an integer from 0 to 2, preferably 0 or 1.

Another aspect of the invention relates to a crystalline compound of Formula (III)

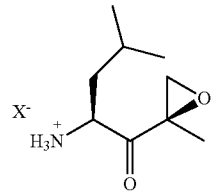

wherein X is any suitable counterion.

Another aspect of this invention relates to methods for the synthesis of amino acid keto-epoxides according to scheme (I)

wherein
R¹ is selected from a protecting group or a further chain of amino acids, which itself may be optionally substituted, preferably a protecting group, most preferably an electron withdrawing protecting group;
R² is selected from hydrogen and $C_{1-6}$alkyl;
R³ is selected from hydrogen, $C_{1-6}$alkyl, $C_{1-6}$alkoxyalkyl, heterocyclyl, aryl, heteroaryl, $C_{1-6}$heteroaralkyl, and $C_{1-6}$aralkyl; and
wherein the method comprises a stereoselective epoxidation under epoxidizing conditions, preferably an aqueous sodium hypochlorite (bleach) or calcium hypochlorite solution in the presence of a cosolvent selected from pyridine, acetonitrile, dimethylformamide (DMF), dimethylsulfoxide (DMSO), N-methylpyrrolidine (NMP), dimethylacetamide (DMA), tetrahydrofuran (THF), and nitromethane.

DETAILED DESCRIPTION OF THE INVENTION

Figure 1:
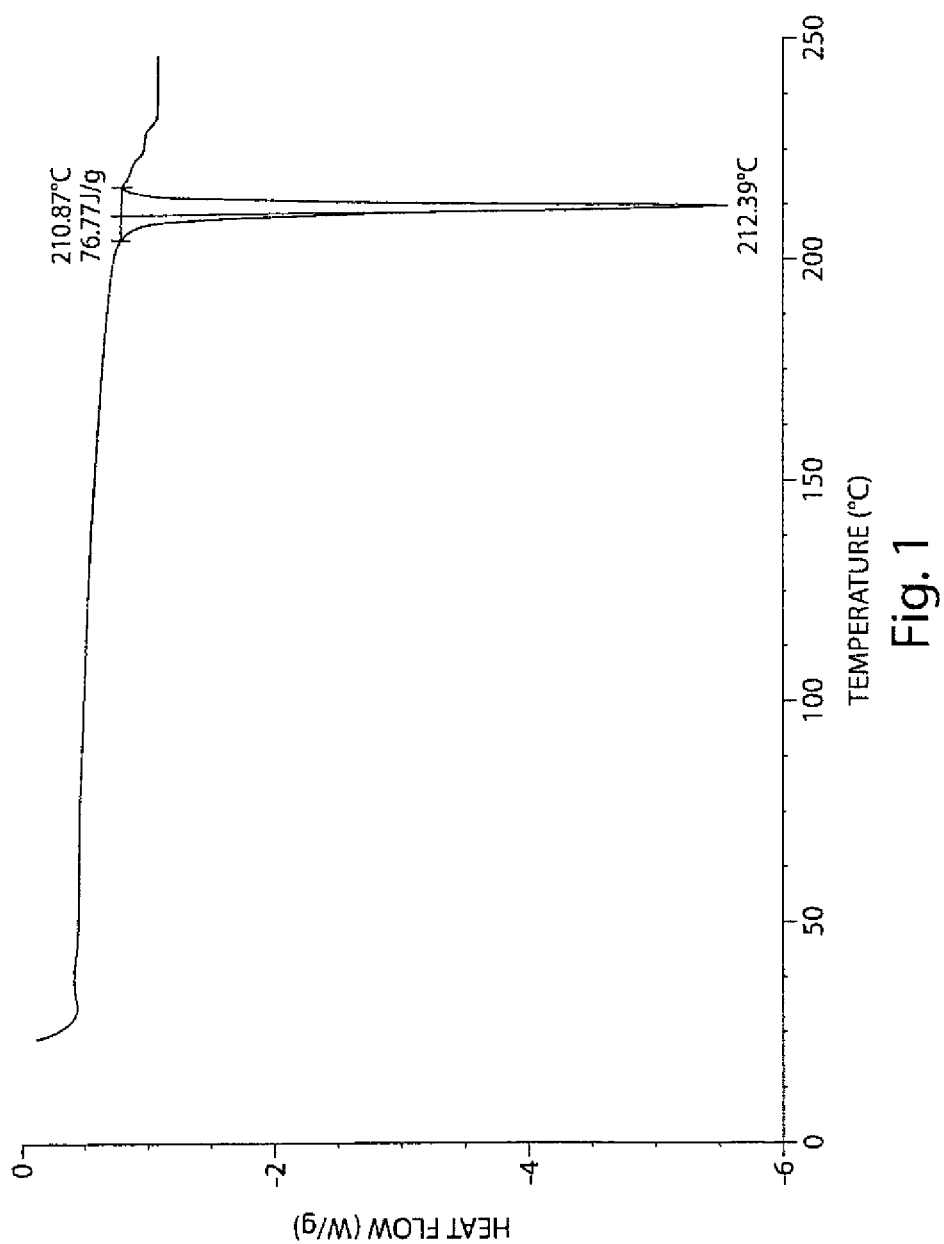
FIG. 1 shows a DSC (differential scanning calorimetry) thermogram of crystalline compound 1.

In certain embodiments, the invention relates to crystalline compounds having a structure of Formula (I) or a pharmaceutically acceptable salt thereof, wherein
X is O, NH, or N-alkyl, preferably O;
Y is NH, N-alkyl, O, or $C(R^9)_2$, preferably N-alkyl, O, or $C(R^9)_2$;
Z is O or $C(R^9)_2$, preferably $C(R^9)_2$;
R¹, R², R³, and R⁴ are hydrogen;
each of R⁵, R⁶, R⁷, R⁸, and R⁹ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether, preferably R⁵, R⁶, R⁷, and R⁸ are independently selected from $C_{1-6}$alkyl, $C_{1-6}$hydroxyalkyl, and $C_{1-6}$aralkyl and each R⁹ is hydrogen, more preferably, R⁶ and R⁸ are independently $C_{1-6}$alkyl, R⁵ and R⁷ are independently $C_{1-6}$aralkyl and each R⁹ is H;
m is an integer from 0 to 2; and
n is an integer from 0 to 2, preferably 0 or 1.

In certain embodiments, X is O and R¹, R², R³, and R⁴ are all the same, preferably R¹, R², R³, and R⁴ are all hydrogen. In certain such embodiments, R⁵, R⁶, R⁷, and R⁸ are independently selected from $C_{1-6}$alkyl, $C_{1-6}$hydroxyalkyl, and $C_{1-6}$aralkyl, more preferably, R⁶ and R⁸ are independently $C_{1-6}$alkyl and R⁵ and R⁷ are independently $C_{1-6}$aralkyl.

In certain preferred embodiments, X is O, R¹, R², R³, and R⁴ are all hydrogen, R⁶ and R⁸ are both isobutyl, R⁵ is phenylethyl, and R⁷ is phenylmethyl.

In certain embodiments, R⁵, R⁶, R⁷, and R⁸ are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether. In certain embodiments, at least one of R⁵ and R⁷ is $C_{1-6}$aralkyl substituted with alkyl, more preferably substituted with perhaloalkyl. In certain such embodiments, R⁷ is $C_{1-6}$aralkyl substituted with trifluoromethyl.

In certain embodiments, Y is selected from N-alkyl, O, and $CH_2$. In certain such embodiments, Z is $CH_2$, and m and n are both 0. In certain alternative such embodiments, Z is $CH_2$, m is 0, and n is 2 or 3. In yet another alternative such embodiments, Z is O, m is 1, and n is 2.

In certain embodiments, the invention relates to a crystalline compound of Formula (II)

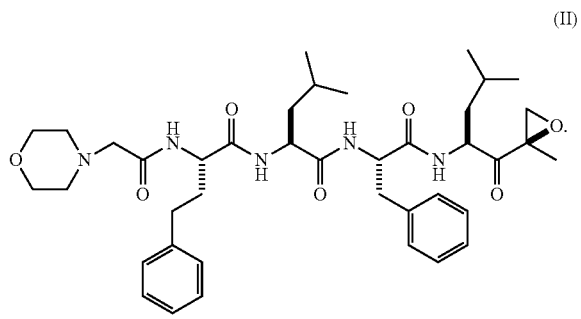

(II)

In certain embodiments, the invention relates to a method for the preparation of a crystalline compound of Formula (I) or (II), comprising one or more of: (i) preparing the amorphous compound, e.g., according to U.S. Pat. No. 7,232,818; (ii) dissolving the amorphous compound in an organic solvent; (iii) bringing the solution to supersaturation to cause formation of crystals; and (iv) isolating the crystals, e.g., by filtering the crystals, by decanting fluid from the crystals, or by any other suitable separation technique. In certain embodiments, preparation further comprises inducing crystallization. In certain embodiments, preparation further comprises washing the filtered crystals, e.g., with a solvent or non-solvent fluid. In certain embodiments, preparation further comprises drying, preferably under reduced pressure, such as under vacuum pressure.

In certain embodiments, the invention relates to a method for the preparation of a crystalline compound of Formula (I) or (II), comprising one or more of: (i) preparing a solution of the amorphous compound, which compound may be prepared according to, for example, U.S. Pat. No. 7,232,818, in an organic solvent; (ii) bringing the solution to supersaturation to cause formation of crystals; and (iii) isolating the crystals, e.g., by filtering the crystals, by decanting fluid from the crystals, or by any other suitable separation technique. In certain embodiments, preparation further comprises inducing crystallization. In certain embodiments, preparation further comprises washing the filtered crystals, e.g., with a solvent or non-solvent fluid. In certain embodiments, preparation further comprises drying, preferably under reduced pressure, such as under vacuum pressure.

In certain embodiments, the amorphous compound may be dissolved in an organic solvent selected from acetonitrile, methanol, ethanol, ethyl acetate, isopropanol, isopropyl acetate, isobutyl acetate, butyl acetate, propyl acetate, methylethyl ketone, methylisobutyl ketone, and acetone, or any combination thereof. In certain embodiments, the amorphous compound may be dissolved in an organic solvent selected from acetonitrile, methanol, ethanol, ethyl acetate, isopropyl acetate, methylethyl ketone, and acetone, or any combination thereof. In certain embodiments, the amorphous compound may be dissolved in an organic solvent selected from acetonitrile, methanol, ethanol, ethyl acetate, methylethylketone, or any combination thereof. In certain embodiments, the organic solvent or solvents may be combined with water.

In certain embodiments, bringing the solution to supersaturation comprises the addition of an anti-solvent, such as water or another polar liquid miscible with the organic solvent, allowing the solution to cool, reducing the volume of the solution, or any combination thereof. In certain embodiments, bringing the solution to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the method further comprises inducing precipitation or crystallization. In certain embodiments inducing precipitation or crystallization comprises secondary nucleation, wherein nucleation occurs in the presence of seed crystals or interactions with the environment (crystallizer walls, stirring impellers, sonication, etc.).

In certain embodiments, washing the crystals comprises washing with a liquid selected from anti-solvent, acetonitrile, methanol, ethanol, ethyl acetate, methylethyl ketone, acetone, or a combination thereof. Preferably the crystals are washed with a combination of anti-solvent and the organic solvent. In certain embodiments, the anti-solvent is water.

In certain embodiments, washing the crystals comprises washing the crystalline compound of Formula (II) with methanol and water.

In certain embodiments, a crystalline compound of Formula (II) is substantially pure. In certain embodiments, the melting point of the crystalline compound of Formula (II) is in the range of about 200 to about 220° C., about 205 to about 215° C., about 211 to about 213° C., or even about 212° C.

In certain embodiments, the DSC of a crystalline compound of Formula (II) has a sharp endothermic maximum at about 212° C., e.g., resulting from melting and decomposition of the crystalline form as shown in FIG. 1.

Figure 2:
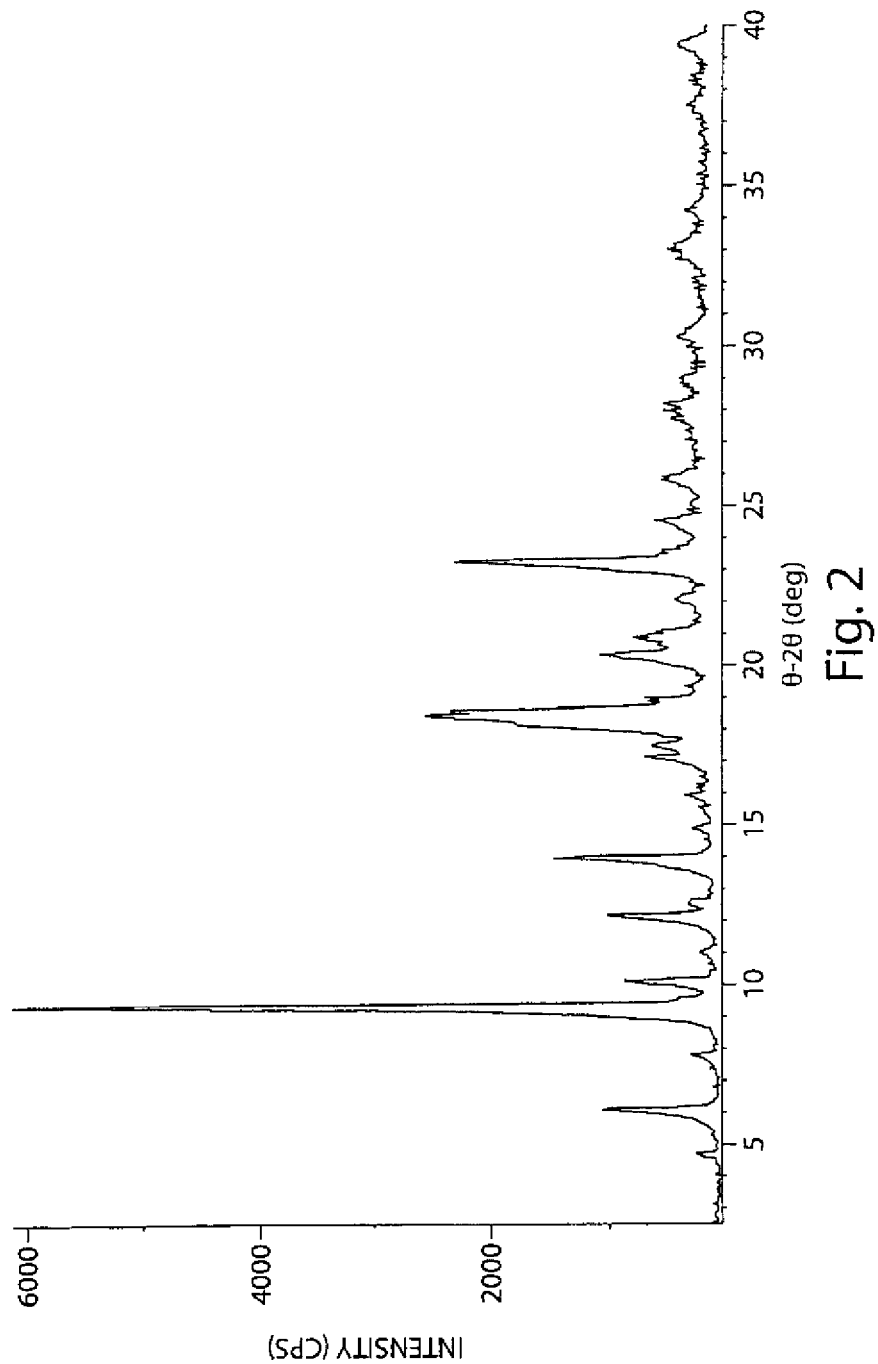
FIG. 2 shows an XRPD (X-ray powder diffraction) pattern of crystalline compound 1.

In certain embodiments, the X-ray powder pattern of a crystalline compound of Formula (II) is (θ-2θ°): 6.10; 8.10; 9.32; 10.10; 11.00; 12.14; 122.50; 13.64; 13.94; 17.14; 17.52; 18.44; 20.38; 21.00; 22.26; 23.30; 24.66; 25.98; 26.02; 27.84; 28.00; 28.16; 29.98; 30.46; 32.98; 33.22; 34.52; 39.46 as shown in FIG. 2.

Figure 3:
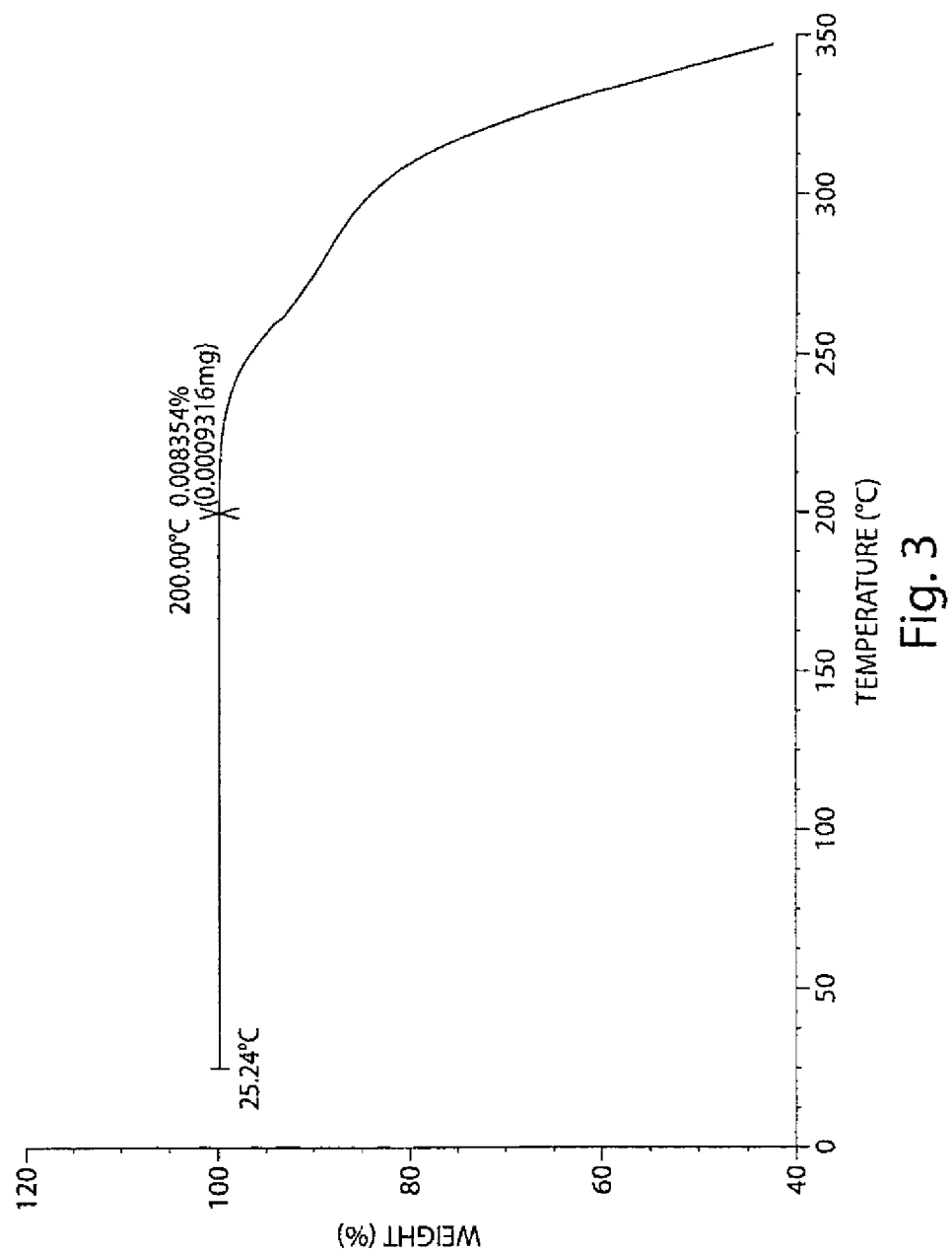
FIG. 3 shows a TG thermogram of crystalline compound 1.
Figure 4:
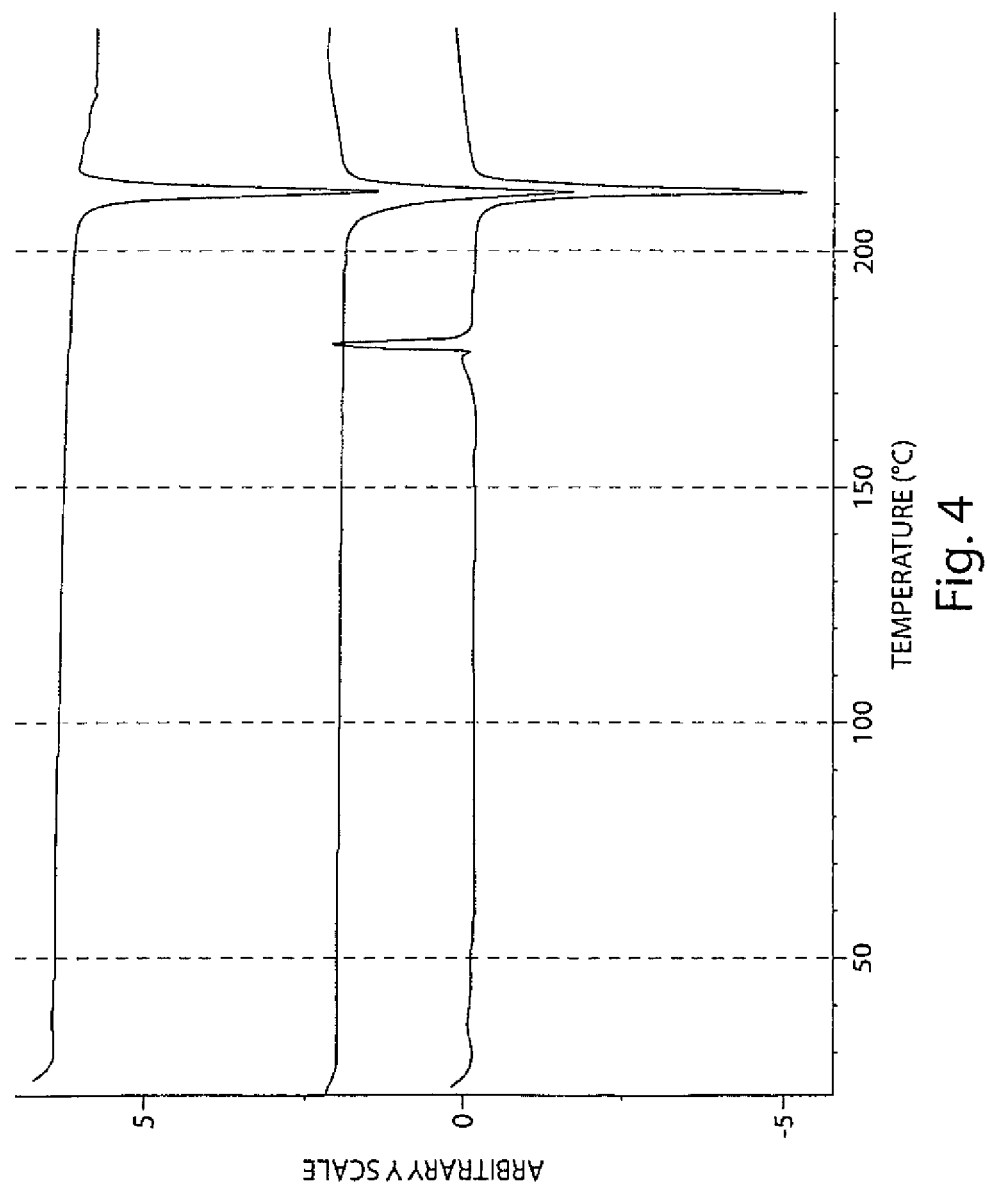
FIG. 4 shows a DSC thermogram of amorphous compound 1 compared to a DSC thermogram of crystalline compound 1.
Figure 5:
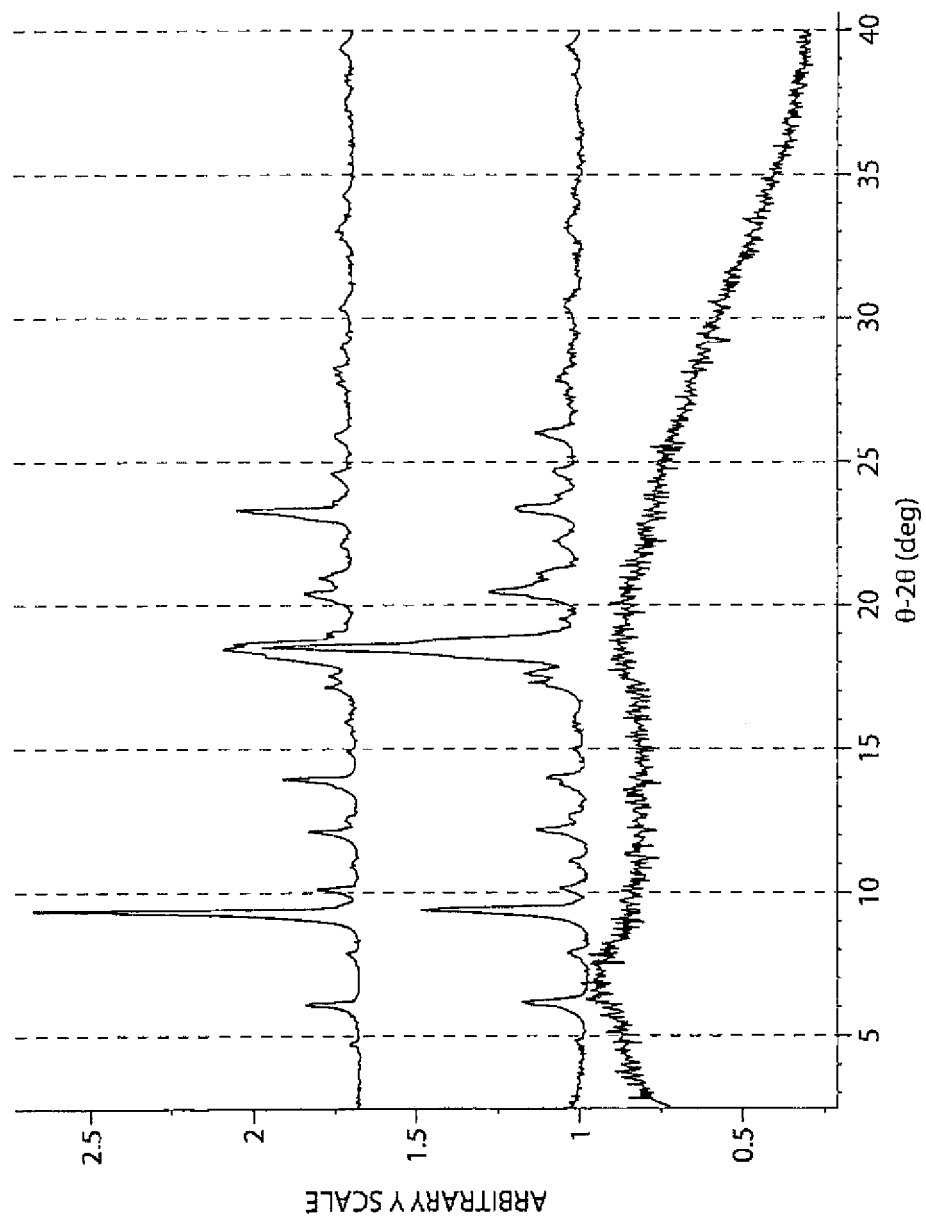
FIG. 5 shows an XRPD pattern of amorphous compound 1 compared to the XRPD pattern of crystalline compound 1.
Figure 6:
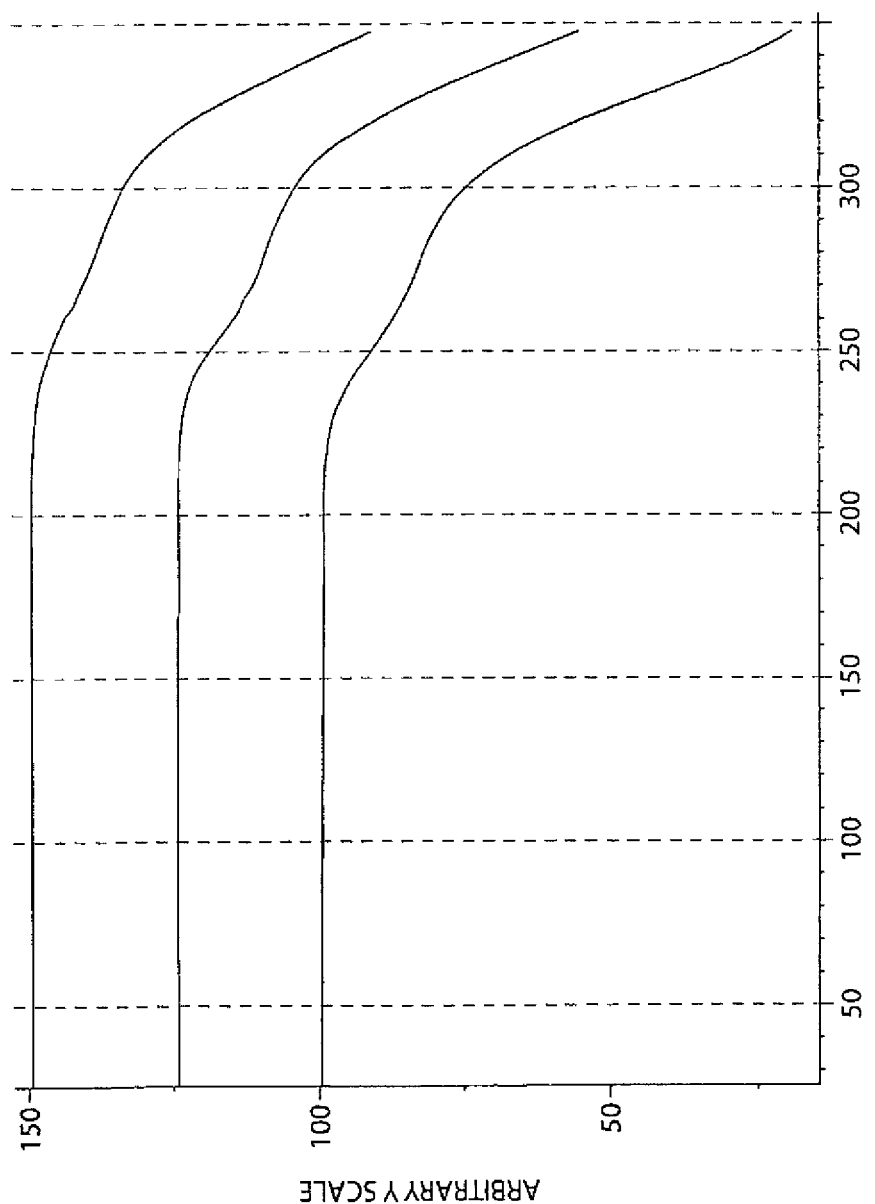
FIG. 6 shows a TG thermogram of amorphous compound 1 compared to the TG pattern of crystalline compound 1.

In certain embodiments, the TG thermogram of a crystalline compound of Formula (II) exhibits from 0.0 to 0.1% weight loss in the temperature range of 25 to 200° C. as shown in FIG. 3.

In certain embodiments, a crystalline compound of Formula (II) is not solvated (e.g., the crystal lattice does not comprise molecules of a solvent). In certain alternative embodiments, a crystalline compound of Formula (II) is solvated.

In certain embodiments, the invention relates to a method for the preparation of an amorphous compound of Formula (II) comprising one or more of (i) dissolving the crystalline compound in an organic solvent; (ii) bringing the solution to supersaturation to cause formation of crystals; and (iii) isolating the crystals, e.g., by filtering the crystals, by decanting fluid from the crystals, or by any other suitable separation technique. In certain embodiments, preparation further comprises inducing precipitation. In certain embodiments, preparation further comprises washing the amorphous compound. In certain embodiments, the method further comprises drying, preferably under reduced pressure, such as under vacuum pressure. In certain embodiments, the invention relates to a crystalline salt of a compound of Formula (I) or (II), wherein the salt counterion is selected from bromide, chloride, sulfate, phosphate, nitrate, acetate, trifluoroacetate, citrate, methanesulfonate, valerate, oleate, palmitate, stearate, laurate, benzoate, lactate, succinate, tosylate, malonate, maleate, fumarate, succinate, tartrate, mesylate, 2-hydroxyethansulfonate, and the like. In certain such embodiments, the salt counterion is selected from citrate, tartrate, trifluoroacetate, methanesulfonate, toluenesulfonate, chloride, and bromide, preferably citrate.

In certain embodiments, the invention relates to a method for the preparation of a crystalline salt of a compound of Formula (II), comprising one or more of: (i) preparing the amorphous compound e.g., according to U.S. Pat. No. 7,232,818; (ii) dissolving the amorphous compound in an organic solvent; (iii) bringing the solution to supersaturation to cause formation of crystals; and (iv) isolating the crystals, e.g., by filtering the crystals, by decanting fluid from the crystals, or by any other suitable separation technique. In certain embodiments, preparation further comprises inducing crystallization. In certain embodiments, preparation further comprises washing the crystals, e.g., with a solvent or non-solvent fluid. In certain embodiments, preparation further comprises drying, preferably under reduced pressure, such as under vacuum pressure.

In certain embodiments, the invention relates to a method for the preparation of a crystalline salt of a compound of Formula (II), comprising one or more of (i) preparing a solution of a compound of Formula (II) in an organic solvent; (ii) adding a suitable acid; (iii) bringing the solution to supersaturation to cause formation of crystals; and (iv) isolating the crystals, e.g., by filtering the crystals, by decanting fluid from the crystals, or by any other suitable separation technique. In certain embodiments, preparation further comprises inducing crystallization. In certain embodiments, preparation further comprises washing the crystals, e.g., with a solvent or non-solvent fluid. In certain embodiments, preparation further comprises drying, preferably under reduced pressure, such as under vacuum pressure. In certain embodiments where the salt is less soluble in a solvent than the free base, adding the acid to a solution may itself be sufficient to bring the solution to supersaturation.

In certain embodiments, the salt counterion is selected from selected from bromide, chloride, sulfate, phosphate, nitrate, acetate, trifluoroacetate, citrate, methanesulfonate, valerate, oleate, palmitate, stearate, laurate, benzoate, lactate, succinate, tosylate, malonate, maleate, fumarate, succinate, tartrate, mesylate, 2-hydroxyethansulfonate, and the like. In certain such embodiments, the salt counterion is selected from citrate, tartrate, trifluoroacetate, methanesulfonate, toluenesulfonate, chloride, and bromide, preferably citrate.

In certain embodiments, the organic solvent is selected from THF, acetonitrile, ether, and MTBE, or any combination thereof, preferably THF or acetonitrile, or a combination thereof.

In certain embodiments, a crystalline citrate salt of a compound of Formula (II) is substantially pure. In certain embodiments, the melting point of the crystalline citrate salt of a compound of Formula (II) is in the range of about 180 to about 190° C. or even about 184 to about 188° C.

Figure 11:
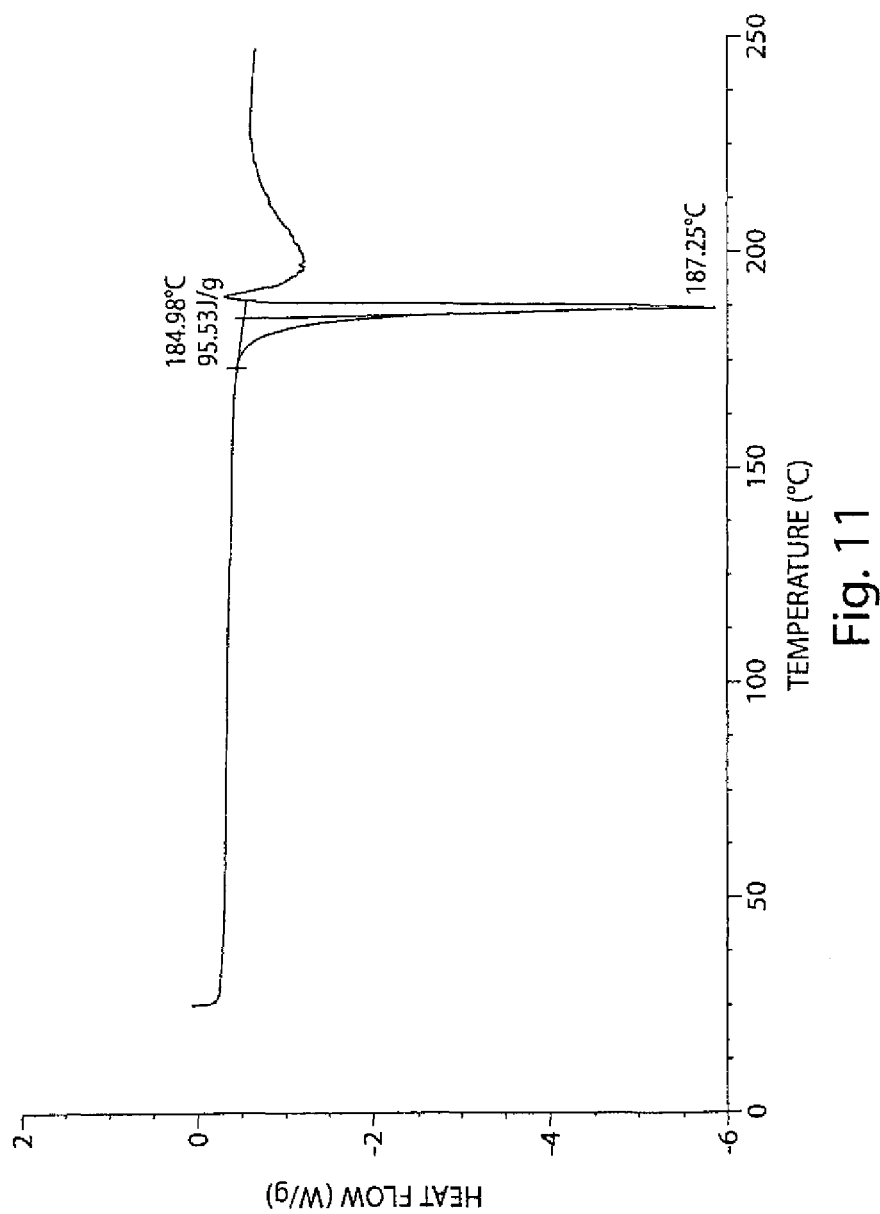
FIG. 11 shows a DSC curve of a crystalline citrate salt of compound 1.

In certain embodiments, the DSC of a crystalline citrate salt of a compound of Formula (II) has a sharp endothermic maximum at about 187° C., e.g., resulting from melting and decomposition of the crystalline form as shown in FIG. 11.

Figure 12:
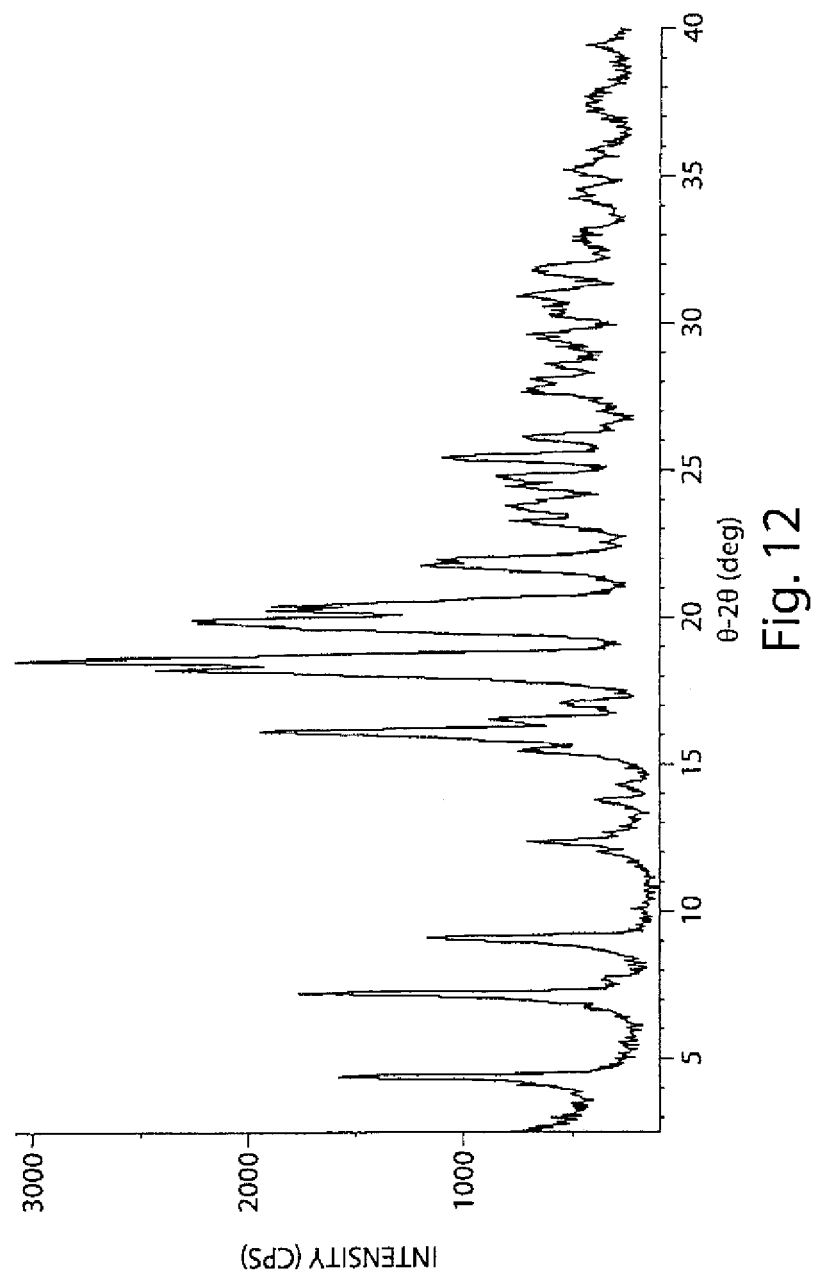
FIG. 12 shows an XRPD pattern of a crystalline citrate salt of compound 1.

In certain embodiments, the X-ray powder pattern of a crystalline citrate salt of a compound of Formula (II) is (θ-2θ°): 4.40; 7.22; 9.12; 12.36; 13.35; 14.34; 15.54; 16.14; 16.54; 17.00; 18.24; 18.58; 19.70; 19.90; 20.30; 20.42; 21.84; 22.02; 23.34; 23.84; 24.04; 24.08; 24.48; 24.76; 25.48; 26.18; 28.14; 28.20; 28.64; 29.64; 31.04; 31.84; 33.00; 33.20; 34.06; 34.30; 34.50; 35.18; 37.48; 37.90; 39.48 as shown in FIG. 12.

In certain embodiments, the invention relates to a crystalline compound of Formula (III)

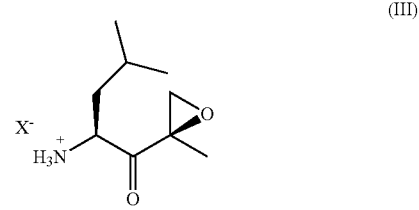

(III)

wherein X is any suitable counterion.

In certain embodiments, X is a counterion selected from bromide, chloride, sulfate, phosphate, nitrate, acetate, trifluoroacetate, citrate, methanesulfonate, valerate, oleate, palmitate, stearate, laurate, benzoate, lactate, succinate, tosylate, malonate, maleate, fumarate, succinate, tartrate, mesylate, 2-hydroxyethansulfonate, and the like. (See, for example, Berge et al. (1977) "Pharmaceutical Salts", J. Pharm. Sci. 66: 1-19.) In certain embodiments X is selected from trifluoroacetate, methanesulfonate, toluenesulfonate, acetate, chloride, and bromide, preferably trifluoroacetate.

In certain embodiments, the invention relates to a method for the preparation of a crystalline compound of Formula (III) comprising one or more of: (i) preparing a compound of Formula (IV), e.g., according to Bioorg. Med. Chem. Letter 1999, 9, 2283-88 or U.S. Patent Application 2005-0256324, wherein PG is a suitable protecting group (e.g., Boc or Cbz)

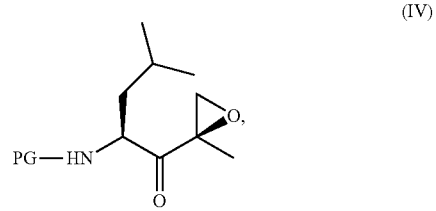

(IV)

(ii) dissolving the compound of Formula (IV) in an organic solvent; (iii) adding a suitable acid; (iv) bringing the solution to supersaturation to cause formation of crystals; and (v) isolating the crystals, e.g., by filtering the crystals, by decanting fluid from the crystals, or by any other suitable separation technique. In certain embodiments, preparation further comprises inducing crystallization. In certain embodiments, preparation further comprises washing the crystals, e.g., with a solvent or non-solvent fluid. In certain embodiments, preparation further comprises drying, preferably under reduced pressure, such as under vacuum pressure.

In certain embodiments, the invention relates to a method for the preparation of a crystalline compound of Formula (III), comprising one or more of: (i) preparing a solution of an amorphous compound of Formula (IV), e.g., according to Bioorg. Med. Chem. Letter 1999, 9, 2283-88 or U.S. Patent Application 2005-0256324, in an organic solvent, wherein PG is a suitable protecting group (e.g., Boc or Cbz).

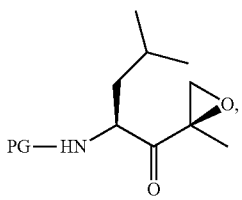

(IV)

(ii) bringing the solution to supersaturation to cause formation of crystals; and (iii) isolating the crystals, e.g., by filtering the crystals, by decanting fluid from the crystals, or by any other suitable separation technique. In certain embodiments, preparation further comprises inducing crystallization. In certain embodiments, preparation further comprises washing the crystals, e.g., with a solvent or non-solvent fluid. In certain embodiments, preparation further comprises drying, preferably under reduced pressure, such as under vacuum pressure.

In certain embodiments the acid is selected from hydrobromic, hydrochloric, sulfuric, phosphoric, nitric, acetic, trifluoroacetic, citric, methanesulfonic, valeric, oleaic, palmitic, stearic, lauric, benzoic, lactic, succinic, p-toluenesulfonic, citric, malonic, maleic, fumaric, succinic, tartaric, methanesulfonic, 2-hydroxyethanesulfonic, and the like. Preferably the acid is trifluoroacetic acid.

In certain embodiments, X is a counterion selected from hydrobromide, hydrochloride, sulfate, phosphate, nitrate, acetate, trifluoroacetate, citrate, methanesulfonate, valerate, oleate, palmitate, stearate, laurate, benzoate, lactate, succinate, tosylate, malonate, maleate, fumarate, succinate, tartrate, mesylate, 2-hydroxyethansulfonate, and the like. (See, for example, Berge et al. (1977) "Pharmaceutical Salts", J. Pharm. Sci. 66: 1-19.) In certain embodiments, X is selected from trifluoroacetate, methanesulfonate, toluenesulfonate, acetate, chloride, and bromide, preferably trifluoroacetate.

In certain embodiments, the compound of Formula (IV) may be dissolved in an organic solvent selected from dichloromethane, ethyl acetate, isopropyl acetate, isobutyl acetate, butyl acetate, propyl acetate, diethyl ether, methyl tert-butyl ether (MTBE), or any combination thereof. In certain embodiments, the organic solvent is selected from dichloromethane, ethyl acetate, MTBE, or any combination thereof, preferably either dichloromethane and MTBE or ethyl acetate and MTBE.

In certain embodiments, bringing the solution to supersaturation comprises the addition of an anti-solvent, such as hexanes or heptanes or another liquid miscible with the organic solvent, allowing the solution to cool, reducing the volume of the solution, or any combination thereof. In certain embodiments, bringing the solution to supersaturation comprises adding an anti-solvent, cooling the solution to ambient temperature or lower, and reducing the volume of the solution, e.g., by evaporating solvent from the solution. In certain embodiments, the anti-solvent is hexanes or heptanes, preferably heptanes.

In certain embodiments, washing the crystals comprises washing with a liquid selected from anti-solvent, ethyl acetate, dichloromethane, or a combination thereof. Preferably the crystals are washed with anti-solvent, preferably heptanes.

Figure 9:
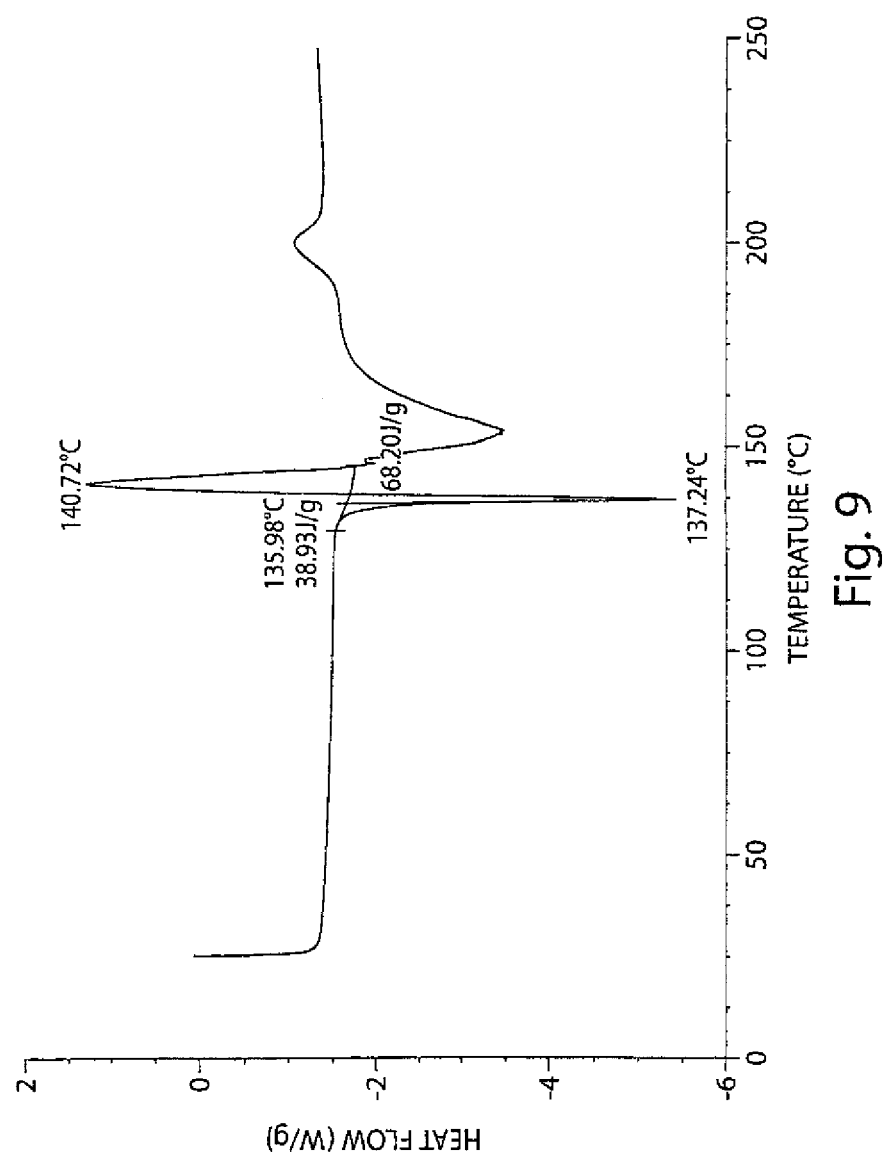
FIG. 9 shows a DSC curve of a crystalline compound F.

In certain embodiments, the DSC of a crystalline compound of Formula (III) has a sharp endothermic maximum at about 137° C., e.g., resulting from melting and decomposition of the crystalline form as shown in FIG. 9.

Figure 10:
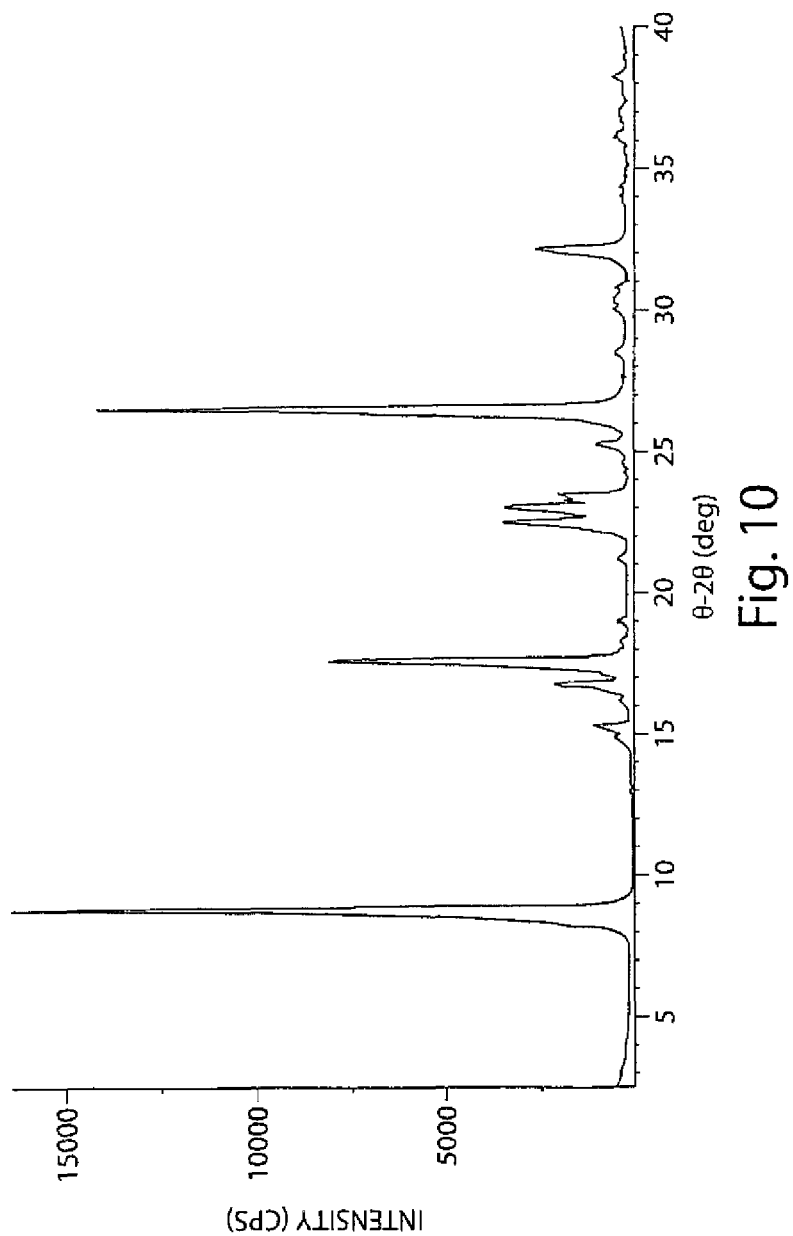
FIG. 10 shows an XRPD pattern of a crystalline compound F.

In certain embodiments, the X-ray powder pattern of a crystalline compound of Formula (II) is (θ-2θ°): 8.84; 15.18; 15.32; 16.20; 16.82; 17.66; 18.26; 19.10; 21.20; 22.58; 23.06; 23.52; 25.32; 26.58; 28.60; 30.08; 30.48; 30.84; 32.20; 36.14; 37.12 as shown in FIG. 10.

In certain embodiments, a crystalline compound of Formula (III) is not solvated (e.g., the crystal lattice does not comprise molecules of a solvent). In certain alternative embodiments, a crystalline compound of Formula (III) is solvated.

In certain embodiments, the invention relates to a method for the preparation of a crystalline compound of Formula (II), comprising one or more of (i) preparing a solution of compound of Formula (IV) wherein PG is a suitable protecting group (e.g., Boc or Cbz), in a first organic solvent

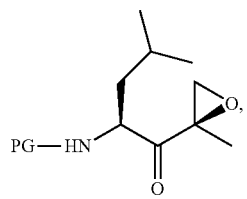

(IV)

(ii) adding a suitable acid; (iii) bringing the solution to supersaturation to cause formation of crystals; (iv) isolating the crystals to provide a crystalline compound of Formula (III); (v) reacting the crystalline compound of Formula (III)

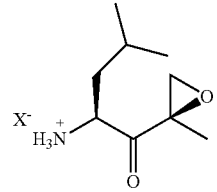

(III)

wherein X is any suitable counterion, with a compound of Formula (V)

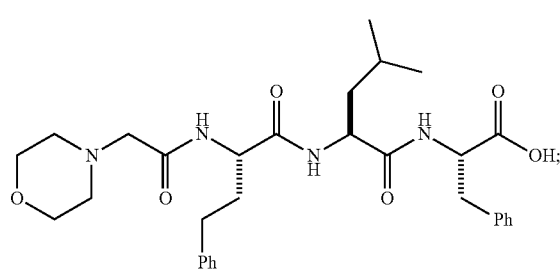

(V)

to provide a compound of Formula (II); (vi) preparing a solution of the compound of Formula (II) in a second organic solvent; (vii) bringing the solution to supersaturation to cause formation of crystals; and (viii) isolating the crystals to provide a crystalline compound of Formula (II), e.g., by filtering the crystals, by decanting, or by any other suitable separation technique. In certain embodiments, preparation further comprises inducing crystallization. In certain embodiments, preparation further comprises washing the crystals, e.g., with a solvent or non-solvent fluid. In certain embodiments, preparation further comprises drying, preferably under reduced pressure, such as under vacuum pressure.

In certain embodiments, the acid is selected from hydrobromic, hydrochloric, sulfuric, phosphoric, nitric, acetic, trifluoroacetic, citric, methanesulfonic, valeric, oleaic, palmitic, stearic, lauric, benzoic, lactic, succinic, p-toluenesulfonic, citric, malonic, maleic, fumaric, succinic, tartaric, methanesulfonic, 2-hydroxyethansulfonic, and the like. Preferably the acid is trifluoroacetic acid.

In certain embodiments, X is a counterion selected from hydrobromide, hydrochloride, sulfate, phosphate, nitrate, acetate, trifluoroacetate, citrate, methanesulfonate, valerate, oleate, palmitate, stearate, laurate, benzoate, lactate, succinate, tosylate, malonate, maleate, fumarate, succinate, tartrate, mesylate, 2-hydroxyethanesulfonate, and the like. (See, for example, Berge et al. (1977) "Pharmaceutical Salts", J. Pharm. Sci. 66: 1-19.) In certain embodiments, X is selected from trifluoroacetate, methanesulfonate, toluenesulfonate, acetate, chloride, and bromide, preferably trifluoroacetate.

In certain embodiments, the first organic solvent is selected from dichloromethane, ethyl acetate, isopropyl acetate, isobutyl acetate, butyl acetate, propyl acetate, diethyl ether, methyl tert-butyl ether (MTBE), or any combination thereof. In certain embodiments, the organic solvent is selected from dichloromethane, ethyl acetate, MTBE, or any combination thereof, preferably either dichloromethane and MTBE or ethyl acetate and MTBE.

In certain embodiments, the second organic solvent is selected from acetonitrile, methanol, ethanol, ethyl acetate, isopropanol, isopropyl acetate, isobutyl acetate, butyl acetate, propyl acetate, methylethyl ketone, methylisobutyl ketone, and acetone, or any combination thereof. In certain embodiments, the amorphous compound may be dissolved in an organic solvent selected from acetonitrile, methanol, ethanol, ethyl acetate, acetone, or any combination thereof. In certain embodiments, the organic solvent or solvents may be combined with water.

In certain embodiments, preparation further comprises washing the crystals of either or both of Formula (II) or (III). In certain embodiments, washing the crystals of a compound of Formula (II) comprises washing with a liquid selected from anti-solvent, acetonitrile, methanol, ethanol, ethyl acetate, acetone, or a combination thereof. Preferably the crystals of a compound of Formula (II) are washed with a combination of anti-solvent and the organic solvent. In certain embodiments, washing the crystals comprises washing the crystalline compound of Formula (II) with methanol and water. In certain embodiments, washing the crystals of a compound of Formula (III) comprises washing with a liquid selected from anti-solvent, ethyl acetate, dichloromethane, or a combination thereof. Preferably the crystals of a compound of Formula (III) are washed with anti-solvent, preferably heptanes.

In certain embodiments, preparation further comprises drying the crystals of either or both of Formula (II) or (III), preferably under reduced pressure, such as under vacuum pressure.

In certain embodiments, the invention relates to a pharmaceutical composition comprising a crystalline compound of Formula (I) or (II) and a pharmaceutically acceptable carrier. In certain embodiments, the pharmaceutical composition is selected from tablets, capsules, and injections.

This invention also relates to methods for the synthesis of epoxyketones, such as formulae (III) and (IV) above. Thus, in another aspect, the invention provides a method for preparing amino acid keto-epoxides according to scheme (I)

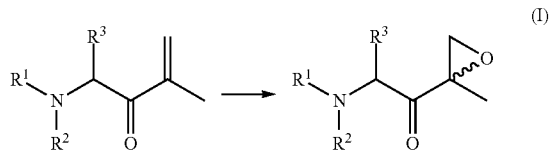

wherein
R$^1$ is selected from a protecting group or a further chain of amino acids, which itself may be optionally substituted, preferably a protecting group, most preferably an electron withdrawing protecting group;
R$^2$ is selected from hydrogen and C$_{1-6}$alkyl; and
R$^3$ is selected from hydrogen, C$_{1-6}$alkyl, C$_{1-6}$alkoxyalkyl, heterocyclyl, aryl, heteroaryl, C$_{1-6}$heteroaralkyl, and C$_{1-6}$aralkyl; and
wherein the method comprises a stereoselective epoxidation under epoxidizing conditions, preferably an aqueous sodium hypochlorite(bleach) or calcium hypochlorite solution in the presence of a cosolvent selected from pyridine, acetonitrile, DMF, DMSO, NMP, DMA, THF, and nitromethane.

In certain embodiments, the cosolvent is selected from NMP and pyridine, preferably pyridine.

In certain embodiments, the epoxidation is performed using aqueous sodium hypochlorite in the presence of a cosolvent selected from pyridine, acetonitrile, DMF, DMSO, NMP, DMA, THF, and nitromethane, preferably NMP or pyridine, more preferably pyridine. In certain embodiments, the epoxidation is performed using a 10% aqueous sodium hypochlorite solution. In certain embodiments, the epoxidation is performed using a 10% aqueous sodium hypochlorite solution in the presence of pyridine. In certain embodiments, the epoxidation is performed using a calcium hypochlorite solution in the presence of NMP.

In certain embodiments, R$^1$ is selected from a protecting group or a further chain of amino acids, which itself may be optionally substituted. In certain such embodiments, R$^1$ is a protecting group, preferably an electron withdrawing protecting group.

In certain embodiments, R$^1$ is selected from t-butoxy carbonyl (Boc), benzoyl (Bz), fluoren-9-ylmethoxycarbonyl (Fmoc), trichloroethoxycarbonyl (Troc), and benzyloxy carbonyl (Cbz). In certain such embodiments, R$^1$ is selected from t-butoxy carbonyl (Boc), benzoyl (Bz), trichloroethoxycarbonyl (Troc), and benzyloxy carbonyl (Cbz), preferably Cbz or Boc. In certain preferred embodiments, R$^1$ is Boc.

In certain embodiments, R$^3$ is selected from hydrogen, C$_{1-6}$alkyl, C$_{1-6}$alkoxyalkyl, heterocyclyl, aryl, heteroaryl, C$_{1-6}$heteroaralkyl, and C$_{1-6}$aralkyl. In preferred embodiments, R$^3$ is C$_{1-6}$alkyl, preferably isobutyl. In certain preferred embodiments, R$^3$ is C$_{1-6}$aralkyl, preferably phenylmethyl, 4-hydroxyphenylmethyl, or 2-phenylethyl.

In certain embodiments, the stereoselective epoxidation is performed under conditions that do not result in significant epimerization of the carbon bearing R$^3$, such that there is less than 10%, less than 5%, less than 2%, or even less than 1% epimerization of the carbon bearing R$^3$. In certain embodiments, the stereoselective epoxidation is performed such that the product is greater than about 90%, greater than 95%, greater than 98%, or even greater than 99% diastereomerically pure.

In certain embodiments, the epoxidation is performed at a temperature in the range of about −15° C. to about 10° C., about −10° C. to about 5° C., or even about −5° C. to about 0° C.

In certain embodiments, the compounds in scheme I have the following stereochemistry

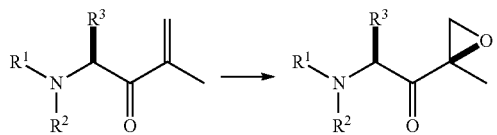

In certain embodiments, the stereoselective epoxidation is performed such that the product is greater than about 90%, greater than 95%, greater than 98%, or even greater than 99% diastereomerically pure.

The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole (HOBT), or 1-hydroxybenzotriazole monohydrate (HOBT), and various cleavage conditions: for example, trifluoroacetic acid (TFA), HCl in dioxane, hydrogenation on Pd/C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds (Greene, T. W.; Wuts, P. G. M. *Protective Groups in Organic Synthesis*, 3$^{rd}$ ed.; Wiley: New York, 1999).

In certain embodiments, the amino acid keto-epoxide may be further modified by deprotection of the amine, if applicable, and coupling with a chain of amino acids. Methods for the coupling of such fragments are well known in the art (Elofsson, M., et al. (1999) *Chemistry & Biology*, 6:811-822; Elofsson, M., et al (1999) *Chemistry & Biology*, 6:811-822). In a preferred embodiment, the chain of amino acids comprises one to three amino acids.

In certain embodiments, the chain of amino acids has a structure of formula (VI) or a pharmaceutically acceptable salt thereof

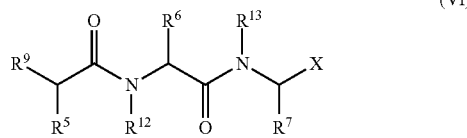

(VI)

wherein each A is independently selected from C=O, C=S, and SO$_2$, preferably C=O; or A is optionally a covalent bond when adjacent to an occurrence of Z;

L is absent or is selected from C=O, C=S, and SO$_2$, preferably L is absent or C=O;

M is absent or is C$_{1-12}$alkyl, preferably C$_{1-8}$alkyl;

Q is absent or is selected from O, NH, and N—C$_{1-6}$alkyl, preferably Q is absent, O, or NH, most preferably Q is absent or O;

X is COOH or an activated form thereof, preferably X is COOH, COCl, or CON(Me)(OMe), most preferably X is COOH or COCl;

Y is absent or is selected from O, NH, N—C$_{1-6}$alkyl, S, SO, SO$_2$, CHOR$^{17}$, and CHCO$_2$R$^{17}$;

each Z is independently selected from O, S, NH, and N—C$_{1-6}$alkyl, preferably O; or Z is optionally a covalent bond when adjacent to an occurrence of A;

R$^5$, R$^6$, and R$^7$ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid (or a salt thereof), ester (including C$_{1-6}$alkyl and C$_{1-5}$alkyl ester and aryl ester), thiol, or thioether substituents;

R$^9$ is N(R$^{10}$)LQR$^{11}$;

R$^{10}$, R$^{12}$, and R$^{13}$ are independently selected from hydrogen, OH, and C$_{1-6}$alkyl, preferably, R$^{10}$ is selected from hydrogen, OH, and C$_{1-6}$alkyl, and R$^{12}$ and R$^{13}$ are independently selected from hydrogen and C$_{1-6}$alkyl, preferably hydrogen;

R$^{11}$ is selected from hydrogen, C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^{15}$ZAZ—C$_{1-8}$alkyl-, R$^{18}$Z—C$_{1-8}$alkyl-, (R$^{15}$O)(R$^{16}$O)P(=O)O—C$_{1-8}$alkyl-ZAZ—C$_{1-8}$alkyl-, R$^{15}$ZAZ—C$_{1-8}$alkyl-ZAZ—C$_{1-8}$alkyl-, heterocyclylM-ZAZ—C$_{1-8}$alkyl-, (R$^{15}$O)(R$^{16}$O)P(=O)O—C$_{1-8}$alkyl-, (R$^{17}$)$_2$N—C$_{1-12}$alkyl-, (R$^{17}$)$_3$N$^+$—C$_{1-12}$alkyl-, heterocyclylM-, carbocyclylM-, R$^{18}$SO$_2$C$_{1-8}$alkyl-, and R$^8$SO$_2$NH; preferably C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^{15}$ZA-C$_{1-8}$alkyl-, R$^{18}$Z—C$_{1-8}$alkyl-, (R$^{15}$O)(R$^{16}$O)P(=O)O—C$_{1-8}$alkyl-ZAZ—C$_{1-8}$alkyl-, (R$^{15}$O)(R$^{16}$O)P(=O)O—C$_{1-8}$alkyl-Z—C$_{1-8}$alkyl-, R$^{15}$ZA-C$_{1-8}$alkyl-ZAZ—C$_{1-8}$alkyl-, heterocyclylMZAZ—C$_{1-8}$alkyl-, (R$^{15}$O)(R$^{16}$O)P(=O) O—C$_{1-8}$alkyl-, (R$^{17}$)$_2$N—C$_{1-8}$alkyl-, (R$^{17}$)$_3$N$^+$—C$_{1-8}$alkyl-, heterocyclylM-, carbocyclylM-, R$^{18}$SO$_2$C$_{1-8}$alkyl-, and R$^{18}$SO$_2$NH, wherein each occurrence of Z and A is independently other than a covalent bond; or R$^{10}$ and R$^{11}$ together are C$_{1-6}$alkyl-Y—C$_{1-6}$alkyl, C$_{1-6}$alkyl-ZAZ—C$_{1-6}$alkyl, ZAZ—C$_{1-6}$alkyl-ZAZ—C$_{1-6}$alkyl, ZAZ—C$_{1-6}$alkyl-ZAZ, or C$_{1-6}$alkyl-A, thereby forming a ring; preferably C$_{1-2}$alkyl-Y—C$_{1-2}$alkyl, C$_{1-2}$alkyl-ZA-C$_{1-2}$alkyl, A-C$_{1-2}$alkyl-ZA-C$_{1-2}$alkyl, A-C$_{1-3}$alkyl-A, or C$_{1-4}$alkyl-A, wherein each occurrence of Z and A is independently other than a covalent bond;

R$^{15}$ and R$^{16}$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^{15}$ and R$^{16}$ together are C$_{1-6}$alkyl, thereby forming a ring;

each R$^{17}$ is independently selected from hydrogen and C$_{1-6}$alkyl, preferably C$_{1-6}$alkyl;

R$^{18}$ is independently selected from hydrogen, OH, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl;

provided that in any occurrence of the sequence ZAZ, at least one member of the sequence must be other than a covalent bond.

In some embodiments, R$^5$, R$^6$, and R$^7$ are selected from C$_{1-6}$alkyl or C$_{1-6}$aralkyl. In preferred embodiments, R$^6$ is C$_{1-6}$alkyl and R$^5$ and R$^7$ are C$_{1-6}$aralkyl. In the most preferred embodiment, R$^6$ is isobutyl, R$^5$ is 2-phenylethyl, and R$^7$ is phenylmethyl.

In certain embodiments, L and Q are absent and R$^{11}$ is selected from C$_{1-6}$alkyl, C$_{1-6}$alkenyl, C$_{1-6}$alkynyl, C$_{1-6}$aralkyl, and C$_{1-6}$heteroaralkyl. In certain such embodiments, R$^{10}$ is C$_{1-6}$alkyl and R$^{11}$ is selected from butyl, allyl, propargyl, phenylmethyl, 2-pyridyl, 3-pyridyl, and 4-pyridyl.

In other embodiments, L is SO$_2$, Q is absent, and R$^{11}$ is selected from C$_{1-6}$alkyl and aryl. In certain such embodiments, R$^{11}$ is selected from methyl and phenyl.

In certain embodiments, L is C=O and $R^{11}$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{15}$ZA-$C_{1-8}$alkyl-, $R^{18}$Z—$C_{1-8}$alkyl-, $(R^{15}O)(R^{16}O)P(=O)O$—$C_{1-8}$alkyl-, $(R^{15}O)(R^{16}O)P(=O)O$—$C_{1-8}$alkyl-ZAZ—$C_{1-8}$alkyl-, $(R^{15}O)(R^{16}O)P(=O)O$—$C_{1-8}$alkyl-Z—$C_{1-8}$alkyl-, $R^{15}$ZA-$C_{1-8}$alkyl-ZAZ—$C_{1-8}$alkyl-, heterocyclylMZAZ—$C_{1-8}$alkyl-, $(R^{17})_2N$—$C_{1-8}$alkyl-, $(R^{17})_3N^+$—$C_{1-8}$alkyl-, heterocyclylM-, carbocyclylM-, $R^{18}SO_2C_{1-8}$alkyl-, and $R^{18}SO_2NH$—, wherein each occurrence of Z and A is independently other than a covalent bond. In certain embodiments, L is C=O, Q is absent, and $R^{11}$ is H.

In certain embodiments, $R^{10}$ is $C_{1-6}$alkyl, $R^{11}$ is $C_{1-6}$alkyl, Q is absent, and L is C=O. In certain such embodiments, $R^{11}$ is ethyl, isopropyl, 2,2,2-trifluoroethyl, or 2-(methylsulfonyl)ethyl.

In other embodiments, L is C=O, Q is absent, and $R^{11}$ is $C_{1-6}$aralkyl. In certain such embodiments, $R^{11}$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^{10}$ is $C_{1-6}$alkyl, and $R^{11}$ is aryl. In certain such embodiments, $R^{11}$ is substituted or unsubstituted phenyl.

In certain embodiments, L is C=O, Q is absent or O, n is 0 or 1, and $R^{11}$ is —$(CH_2)_n$carbocyclyl. In certain such embodiments, $R^{11}$ is cyclopropyl or cyclohexyl.

In certain embodiments, L and A are C=O, Q is absent, Z is O, n is an integer from 1 to 8 (preferably 1), and $R^{11}$ is selected from $R^{15}$ZA-$C_{1-8}$alkyl-, $R^{18}$Z—$C_{1-8}$alkyl-, $R^{15}$ZA-$C_{1-8}$alkyl-ZAZ—$C_{1-8}$alkyl-, $(R^{15}O)(R^{16}O)P(=O)O$—$C_{1-8}$alkyl-ZAZ—$C_{1-8}$alkyl-, $(R^{15}O)(R^{16}O)P(=O)O$—$C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, $R^7$ is heterocyclylMZAZ—$C_{1-8}$alkyl- where heterocyclyl is substituted or unsubstituted oxodioxolenyl or $N(R^{12})(R^{13})$, wherein $R^{12}$ and $R^{13}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, n is an integer from 1 to 8, and $R^{11}$ is selected from $(R^{15}O)(R^{16}O)P(=O)O$—$C_{1-8}$alkyl-, $(R^{17})_2NC_{1-8}$alkyl-, $(R^{17})_3N^+(CH_2)_n$—, and heterocyclyl-M-. In certain such embodiments, $R^{11}$ is —$C_{1-8}$alkylN$(R^7)_2$ or —$C_{1-8}$alkylN$^+(R^{17})_3$, where $R^{17}$ is $C_{1-8}$alkyl. In certain other such embodiments, $R^{11}$ is heterocyclylM-, where heterocyclyl is selected from morpholino, piperidino, piperazino, and pyrrolidino.

In certain embodiments, L is C=O, $R^{10}$ is $C_{1-6}$alkyl, Q is selected from O and NH and $R^{11}$ is selected from $C_{1-6}$alkyl, cycloalkyl-M, $C_{1-6}$aralkyl, and $C_{1-6}$heteroaralkyl. In other embodiments, L is C=O, $R^{10}$ is $C_{1-6}$alkyl, Q is selected from O and NH, and $R^{11}$ is $C_{1-6}$alkyl, where $C_{1-6}$alkyl is selected from methyl, ethyl, and isopropyl. In further embodiments, L is C=O, $R^{10}$ is $C_{1-6}$alkyl, Q is selected from O and NH and $R^{11}$ is $C_{1-6}$aralkyl, where aralkyl is phenylmethyl. In other embodiments, L is C=O, $R^{10}$ is $C_{1-6}$alkyl, Q is selected from O and NH, and $R^{11}$ is $C_{1-6}$heteroaralkyl, where heteroaralkyl is (4-pyridyl)methyl.

In certain embodiments, L is absent or is C=O, and $R^{10}$ and $R^{11}$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^{10}$ and $R^{11}$ together are $C_{1-3}$alkyl-Y—$C_{1-3}$alkyl. In another preferred embodiment, L and A are absent, and $R^{10}$ and $R^{11}$ together are $C_{1-3}$alkyl-Y—$C_{1-3}$alkyl. In another preferred embodiment, L is C=O, Q is absent, Y is selected from NH and N—$C_{1-6}$alkyl, and $R^{10}$ and $R^{11}$ together are $C_{1-3}$alkyl-Y—$C_{1-3}$alkyl. In another preferred embodiment, L is C=O, Y is absent, and $R^{10}$ and $R^{11}$ together are $C_{1-3}$alkyl-Y—$C_{1-3}$alkyl. In another preferred embodiment, L and A are C=O, and $R^{10}$ and $R^{11}$ together are $C_{1-2}$alkyl-ZA-$C_{1-2}$alkyl. In another preferred embodiment, L and A are C=O and $R^{10}$ and $R^{11}$ together are $C_{2-3}$alkyl-A.

In certain embodiments, the chain of amino acids has a structure of formula (VII)

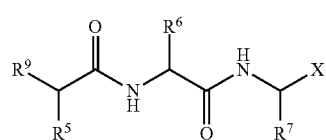

(VII)

wherein each A is independently selected from C=O, C=S, and $SO_2$, preferably C=O; or A is optionally a covalent bond when adjacent to an occurrence of Z;

each B is independently selected from C=O, C=S, and $SO_2$, preferably C=O;

D is absent or is $C_{1-8}$alkyl;

G is selected from O, NH, and N—$C_{1-6}$alkyl;

K is absent or is selected from C=O, C=S, and $SO_2$, preferably K is absent or is C=O;

L is absent or is selected from C=O, C=S, and $SO_2$, preferably L is absent or C=O;

M is absent or is $C_{1-8}$alkyl;

Q is absent or is selected from O, NH, and N—$C_{1-6}$alkyl, preferably Q is absent, O, or NH, most preferably Q is absent;

X is COOH or an activated form thereof, preferably X is COOH, COCl, or CON(Me)(OMe), most preferably X is COOH or COCl;

each V is independently absent or is selected from O, S, NH, and N—$C_{1-6}$alkyl, preferably V is absent or O;

W is absent or is independently selected from O, S, NH, and N—$C_{1-6}$alkyl, preferably O;

Y is absent or is selected from O, NH, N—$C_{1-6}$alkyl, S, SO, $SO_2$, $CHOR^{17}$, and $CHCO_2R^{17}$;

each Z is independently selected from O, S, NH, and N—$C_{1-6}$alkyl, preferably O; or Z is optionally a covalent bond when adjacent to an occurrence of A;

$R^5$, $R^6$, and $R^7$ are each independently selected from $C_{1-6}$alkyl, $C_{1-6}$hydroxyalkyl, $C_{1-6}$alkoxyalkyl, aryl, $C_{1-6}$aralkyl, and $R^{16}$DVKOC$_{1-3}$alkyl-, wherein at least one of $R^5$ and $R^7$ is $R^{16}$DVKOC$_{1-3}$alkyl-;

$R^9$ is $N(R^{10})LQR^{11}$;

$R^{10}$ is selected from hydrogen, OH, and $C_{1-6}$alkyl, preferably hydrogen or $C_{1-6}$alkyl;

$R^{11}$ is a further chain of amino acids, hydrogen, a protecting group, aryl, or heteroaryl, any of which is optionally substituted with halogen, carbonyl, nitro, hydroxy, aryl, $C_{1-5}$alkyl; or $R^{11}$ is selected from $C_{1-6}$alkyl, $C_{1-6}$alkenyl, $C_{1-6}$alkynyl, $C_{1-6}$aralkyl, $C_{1-6}$heteroaralkyl, $R^{12}$ZAZ—$C_{1-8}$alkyl-, $R^{15}$ZAZ—$C_{1-8}$alkyl-, $(R^{12}O)(R^{13}O)P(=O)O$—$C_{1-8}$alkyl-ZAZ—$C_{1-8}$alkyl-, $R^{12}$ZAZ—$C_{1-8}$alkyl-ZAZ—$C_{1-8}$alkyl-, heterocyclylMZAZ—$C_{1-8}$alkyl-, $(R^{12}O)(R^{13}O)P(=O)O$—$C_{1-8}$alkyl-, $(R^{14})_2N$—$C_{1-8}$alkyl-, $(R^{14})_3N^+$—$C_{1-8}$alkyl-, heterocyclylM-, carbocyclylM-, $R^{15}SO_2C_{1-8}$alkyl-, and $R^{15}SO_2NH$—; or $R^{10}$ and $R^{11}$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-ZAZ;

$R^{12}$ and $R^{13}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{12}$ and $R^{13}$ together are $C_{1-6}$alkyl, thereby forming a ring;

each $R^{14}$ is independently selected from hydrogen and $C_{1-6}$alkyl, preferably $C_{1-6}$alkyl;

each $R^{15}$ is independently selected from hydrogen, $OR^{14}$, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{16}$ is selected from hydrogen, $(R^{17}O)(R^{18}O)P(=O)W—$, $R^{17}GB—$, heterocyclyl-, $(R^{19})_2N—$, $(R^{19})_3N^+—$, $R^{19}SO_2GBG-$, and $R^{17}GBC_{1-8}$alkyl- where the $C_{1-8}$alkyl moiety is optionally substituted with OH, $C_{1-8}$alkylW (optionally substituted with halogen, preferably fluorine), aryl, heteroaryl, carbocyclyl, heterocyclyl, and $C_{1-6}$aralkyl, preferably at least one occurrence of $R^{16}$ is other than hydrogen;

$R^{17}$ and $R^{18}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{17}$ and $R^{18}$ together are $C_{1-6}$alkyl, thereby forming a ring; and each $R^{19}$ is independently selected from hydrogen, $OR^{14}$, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl; and D, G, V, K, and W are selected such that there are no O—O, N—O, S—N, or S—O bonds.

In certain embodiments, $R^5$, $R^6$, and $R^7$ are each independently selected from $C_{1-6}$alkyl, $C_{1-6}$hydroxyalkyl, $C_{1-6}$alkoxyalkyl, aryl, $C_{1-6}$aralkyl, and $R^{16}DVKOC_{1-3}$alkyl- wherein at least one of $R^5$ and $R^7$ is $R^{16}DVKOC_{1-3}$alkyl-. In preferred embodiments, one of $R^5$ and $R^7$ is $C_{1-6}$aralkyl and the other is $R^{16}DVKOC_{1-3}$alkyl-, and $R^6$ is independently $C_{1-6}$alkyl. In the most preferred embodiment, one of $R^5$ and $R^7$ is 2-phenylethyl or phenylmethyl and the other is $R^{16}DVKOCH_2—$ or $R^{16}DVKO(CH_3)CH—$, and $R^6$ is isobutyl.

In certain embodiments, each $R^{15}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, each $R^{19}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, L and Q are absent and $R^{11}$ is selected from hydrogen, a further chain of amino acids, $C_{1-6}$acyl, a protecting group, aryl, heteroaryl, $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^{10}$ is $C_{1-6}$alkyl and $R^{11}$ is selected from butyl, allyl, propargyl, phenylmethyl, 2-pyridyl, 3-pyridyl, and 4-pyridyl.

In other embodiments, L is $SO_2$, Q is absent, and $R^{11}$ is selected from $C_{1-6}$alkyl and aryl. In certain such embodiments, $R^{11}$ is selected from methyl and phenyl.

In certain embodiments, L is C=O and $R^{11}$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{12}ZA-C_{1-8}$alkyl-, $R^{15}Z—C_{1-8}$alkyl-, $(R^{12}O)(R^{13}O)P(=O)O—C_{1-8}$alkyl-, $(R^{12}O)(R^{13}O)P(=O)O—C_{1-8}$alkyl-ZAZ—$C_{1-8}$alkyl-, $(R^{12}O)(R^{13}O)P(=O)O—C_{1-8}$alkyl-Z—$C_{1-8}$alkyl-, $R^{12}ZA-C_{1-8}$alkyl-ZAZ—$C_{1-8}$alkyl-, heterocyclylMZAZ—$C_{1-8}$alkyl-, $(R^{14})_2N—C_{1-8}$alkyl-, $(R^{14})_3N^+—C_{1-8}$alkyl-, heterocyclylM-, carbocyclylM-, $R^{15}SO_2C_{1-8}$alkyl-, and $R^{15}SO_2NH—$. In certain embodiments, L is C=O, Q is absent, and $R^{11}$ is H.

In certain embodiments, $R^{10}$ is $C_{1-6}$alkyl, $R^{11}$ is $C_{1-6}$alkyl, Q is absent, and L is C=O. In certain such embodiments, $R^{11}$ is ethyl, isopropyl, 2,2,2-trifluoroethyl, or 2-(methylsulfonyl)ethyl.

In other embodiments, L is C=O, Q is absent, and $R^{11}$ is $C_{1-6}$aralkyl. In certain such embodiments, $R^{11}$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^{10}$ is $C_{1-6}$alkyl, and $R^{11}$ is aryl. In certain such embodiments, $R^{11}$ is substituted or unsubstituted phenyl.

In certain embodiments, L is C=O, Q is absent or O, and $R^{11}$ is —$(CH_2)_n$carbocyclyl. In certain such embodiments, $R^{11}$ is cyclopropyl or cyclohexyl.

In certain embodiments, L and A are C=O, Q is absent, Z is O, and $R^{11}$ is selected from $R^{12}ZA-C_{1-8}$alkyl-, $R^{15}Z—C_{1-8}$alkyl-, $R^{12}ZA-C_{1-8}$alkyl-ZAZ—$C_{1-8}$alkyl-, $(R^{12}O)(R^{13}O)P(=O)O—C_{1-8}$alkyl-ZAZ—$C_{1-8}$alkyl-, $(R^{12}O)(R^{13}O)P(=O)O—C_{1-8}$alkyl-Z—$C_{1-8}$alkyl-, and heterocyclylMZAZ—$C_{1-8}$alkyl-. In certain such embodiments, $R^{11}$ is heterocyclylMZAZ—$C_{1-8}$alkyl- where heterocyclyl is substituted or unsubstituted oxodioxolenyl or $N(R^{20})(R^{21})$, wherein $R^{20}$ and $R^{21}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, and $R^{11}$ is selected from $(R^{12}O)(R^{13}O)P(=O)O—C_{1-8}$alkyl-, $(R^{14})_2NC_{1-8}$alkyl, $(R^{14})_3N^+(CH_2)_n—$, and heterocyclyl-M-. In certain such embodiments, $R^{11}$ is —$C_{1-8}$alkylN$(R^{14})_2$ or —$C_{1-8}$alkylN$^+(R^{14})_3$, where $R^{14}$ is $C_{1-6}$alkyl. In certain other such embodiments, $R^{11}$ is heterocyclylM-, where heterocyclyl is selected from morpholino, piperidino, piperazino, and pyrrolidino.

In certain embodiments, L is C=O, $R^{10}$ is $C_{1-6}$alkyl, Q is selected from O and NH and $R^{11}$ is selected from $C_{1-6}$alkyl, cycloalkyl-M, $C_{1-6}$araalkyl, and $C_{1-6}$heteroaralkyl. In other embodiments, L is C=O, $R^{10}$ is $C_{1-6}$alkyl, Q is selected from O and NH, and $R^{11}$ is $C_{1-6}$alkyl, where $C_{1-6}$alkyl is selected from methyl, ethyl, and isopropyl. In further embodiments, L is C=O, $R^{10}$ is $C_{1-6}$alkyl, Q is selected from O and NH and $R^{11}$ is $C_{1-6}$aralkyl, where aralkyl is phenylmethyl. In other embodiments, L is C=O, $R^{10}$ is $C_{1-6}$alkyl, Q is selected from O and NH, and $R^{11}$ is $C_{1-6}$heteroaralkyl, where heteroaralkyl is (4-pyridyl)methyl.

In certain embodiments, L is absent or is C=O, and $R^{10}$ and $R^{11}$ together are $C_{1-6}$alkyl-Y—$C_{1-6}$alkyl, $C_{1-6}$alkyl-ZA-$C_{1-6}$alkyl, or $C_{1-6}$alkyl-A, thereby forming a ring. In certain preferred embodiments, L is C=O, Q and Y are absent, and $R^{10}$ and $R^{11}$ together are $C_{1-3}$alkyl-Y—$C_{1-3}$alkyl. In another preferred embodiment, L and Q are absent, and $R^{10}$ and $R^{11}$ together are $C_{1-3}$alkyl-Y—$C_{1-3}$alkyl. In another preferred embodiment, L is C=O, Q is absent, Y is selected from NH and N—$C_{1-6}$alkyl, and $R^{10}$ and $R^{11}$ together are $C_{1-3}$alkyl-Y—$C_{1-3}$alkyl. In another preferred embodiment, L is C=O, Y is absent, and $R^{10}$ and $R^{11}$ together are $C_{1-3}$alkyl-Y—$C_{1-3}$alkyl. In another preferred embodiment, L and A are C=O, and $R^{10}$ and $R^{11}$ together are $C_{1-2}$alkyl-ZA-$C_{1-2}$alkyl. In another preferred embodiment, L and A are C=O and $R^{10}$ and $R^{11}$ together are $C_{2-3}$alkyl-A.

In certain embodiments, $R^{16}$ is $(R^{17}O)(R^{18}O)P(=O)W—$. In certain such embodiments, D, V, K, and W are absent. In other such embodiments, V and K are absent, D is $C_{1-8}$alkyl, and W is O. In yet other such embodiments, D is $C_{1-8}$alkyl, K is C=O, and V and W are O.

In certain embodiments, $R^{16}$ is $R^{17}GB$—. In preferred embodiments, B is C=O, G is O, D is $C_{1-8}$alkyl, V is O, and K is C=O.

In certain embodiments, $R^{16}$ is heterocyclyl-. In preferred such embodiments, D is $C_{1-8}$alkyl. In certain such embodiments, V is O, K is C=O, and heterocyclyl is oxodioxolenyl. In other such embodiments, V is absent, K is absent or is C=O, and heterocyclyl is $N(R^{20})(R^{21})$, where $R^{20}$ and $R^{21}$ together are J-T-J, J-WB-J, or B-J-T-J, T is absent or is selected from O, $NR^{17}$, S, SO, $SO_2$, $CHOR^{19}$, $CHCO_2R^{17}$, C=O, $CF_2$, and CHF, and J is absent or is $C_{1-3}$alkyl.

In certain embodiments, $R^{16}$ is $(R^{19})_2N$— or $(R^{19})_3N^+$—, and preferably V is absent. In preferred such embodiments, D is $C_{1-8}$alkyl and K is absent or C=O. In certain embodiments where V is absent and $R^{16}$ is $(R^{19})_2N$—, D is absent K is absent or is C=O, preferably K is C=O.

In certain embodiments, $R^{16}$ is $R^{19}SO_2GBG$-. In preferred such embodiments, B is C=O, D, V, and K are absent, and G is NH or $NC_{1-6}$alkyl.

In certain embodiments, $R^{16}$ is $R^{17}GBC_{1-8}$alkyl-. In preferred embodiments, B is C=O, G is O, and the $C_{1-8}$alkyl moiety is optionally substituted with OH, $C_{1-8}$alkyl (optionally substituted with halogen, preferably fluorine), $C_{1-8}$alkylW, aryl, heteroaryl, carbocyclyl, heterocyclyl, and $C_{1-6}$aralkyl. In certain such embodiments, the $C_{1-8}$alkyl moiety is an unsubstituted, mono-, or disubstituted $C_1$alkyl.

In certain embodiments, the chain of amino acids has a structure of formula (VIII) or (IX) or a pharmaceutically acceptable salt thereof

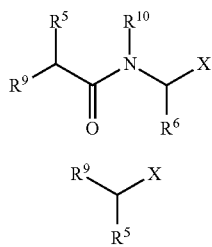

wherein
each Ar is independently an aromatic or heteroaromatic group optionally substituted with 1 to 4 substituents;
L is absent or is selected from C=O, C=S, and $SO_2$, preferably $SO_2$ or C=O;
X is COOH or an activated form thereof, preferably X is COOH, COCl, or CON(Me)(OMe), most preferably X is COOH or COCl;
Y is absent or is selected from C=O and $SO_2$;
Z is absent or is $C_{1-6}$alkyl;
$R^5$ and $R^6$ are each independently selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents;
$R^9$ is $N(R^{10})L$-Z—$R^{11}$;
$R^{10}$ is selected from hydrogen, OH, $C_{1-6}$aralkyl-Y—, and $C_{1-6}$alkyl-Y—, preferably hydrogen;
$R^{11}$ is selected from hydrogen, $OR^{12}$, $C_{1-6}$alkenyl, Ar—Y—, carbocyclyl, and heterocyclyl; and
$R^{12}$ is selected from hydrogen, $C_{1-6}$alkyl, and $C_{1-6}$aralkyl, preferably hydrogen.

In certain embodiments, L is selected from C=O, C=S, and $SO_2$, preferably $SO_2$ or C=O.

In certain embodiments, $R^{10}$ is selected from hydrogen, OH, $C_{1-6}$aralkyl, and $C_{1-6}$alkyl, preferably hydrogen.

In certain embodiments, $R^{11}$ is selected from hydrogen, $C_{1-6}$alkenyl, Ar—Y—, carbocyclyl, and heterocyclyl.

In certain embodiments, $R^5$ and $R^6$ are each independently selected from $C_{1-6}$alkyl, $C_{1-6}$hydroxyalkyl, and $C_{1-6}$aralkyl. In preferred such embodiments, $R^5$ is $C_{1-6}$alkyl and $R^6$ is $C_{1-6}$aralkyl. In more preferred such embodiments, $R^5$ is isobutyl and $R^6$ is phenylmethyl.

In certain embodiments, $R^{10}$ is hydrogen, L is C=O or $SO_2$, $R^{11}$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-Q-, where Q is selected from a direct bond, —O—, and $C_{1-6}$alkyl. In certain other such embodiments where Z is $C_{1-6}$alkyl, Z may be substituted, preferably with Ar, e.g., phenyl.

In certain embodiments, $R^{10}$ is hydrogen, Z is absent, L is C=O or $SO_2$, and $R^{11}$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^{10}$ is hydrogen, L is C=O or $SO_2$, Z is absent, and $R^{11}$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, $R^{12}$ is selected from hydrogen and $C_{1-6}$alkyl. In certain preferred such embodiments, $R^{12}$ is selected from hydrogen and methyl. In more preferred such embodiments, $R^{12}$ is hydrogen.

In certain preferred embodiments, the chain of amino acids has a structure of formula (X)

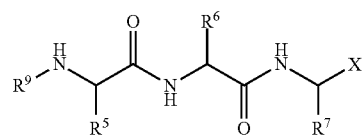

X is COOH or an activated form thereof, preferably X is COOH, COCl, or CON(Me)(OMe), most preferably X is COOH or COCl;
$R^5$, $R^6$, and $R^7$ are independently selected from $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether, preferably $R^6$ is $C_{1-6}$alkyl and $R^5$ and $R^7$ are $C_{1-6}$aralkyl, most preferably, $R^6$ is isobutyl, $R^5$ is 2-phenylethyl, and $R^7$ is phenylmethyl;
$R^9$ is a further chain of amino acids, hydrogen, $C_{1-6}$acyl, a protecting group, aryl, or heteroaryl, where substituents include halogen, carbonyl, nitro, hydroxy, aryl, and $C_{1-8}$alkyl, preferably $R^9$ is $C_{1-6}$acyl, most preferably $R^9$ is acetyl.

In certain preferred embodiments, the chain of amino acids has a structure of formula (XI) or a pharmaceutically acceptable salt thereof,

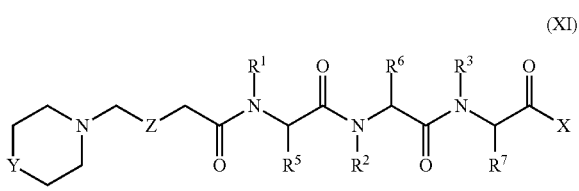

(XI)

wherein

L is absent or is selected from —CO₂ or —C(=S)O;

X is COOH or an activated form thereof, preferably X is COOH, COCl, or CON(Me)(OMe), most preferably X is COOH or COCl;

Y is NH, N-alkyl, O, or C(R⁹)₂, preferably N-alkyl, O, or C(R⁹)₂;

Z is O or C(R⁹)₂, preferably C(R⁹)₂;

R¹, R², and R³ are independently selected from hydrogen and a group of formula (XII), preferably, R¹, R², and R³ are all the same, more preferably R¹, R², and R³ are all hydrogen;

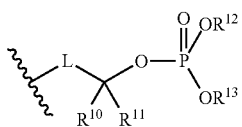

(XII)

each R⁵, R⁶, R⁷, and R⁹ is independently selected from hydrogen, C₁₋₆alkyl, C₁₋₆hydroxyalkyl, C₁₋₆alkoxyalkyl, aryl, and C₁₋₆aralkyl, each of which is optionally substituted with a group selected from alkyl, amide, amine, carboxylic acid or a pharmaceutically acceptable salt thereof, carboxyl ester, thiol, and thioether, preferably R⁵, R⁶, and R⁷ are independently selected from C₁₋₆alkyl, C₁₋₆hydroxyalkyl, and C₁₋₆aralkyl and each R⁹ is hydrogen, more preferably, R⁶ is C₁₋₆alkyl, R⁵ and R⁷ are independently C₁₋₆aralkyl and each R⁹ is H;

R¹⁰ and R¹¹ are independently selected from hydrogen and C₁₋₆alkyl, or R¹⁰ and R¹¹ together form a 3- to 6-membered carbocyclic or heterocyclic ring;

R¹² and R¹³ are independently selected from hydrogen, a metal cation, C₁₋₆alkyl, and C₁₋₆aralkyl, or R¹² and R¹³ together represent C₁₋₆alkyl, thereby forming a ring;

m is an integer from 0 to 2; and n is an integer from 0 to 2, preferably 0 or 1.

In certain embodiments, X is O and R¹, R², and R³ are all the same, preferably R¹, R², and R³ are all hydrogen. In certain such embodiments, R⁵, R⁶, and R⁷ are independently selected from C₁₋₆alkyl, C₁₋₆hydroxyalkyl, and C₁₋₆aralkyl, more preferably, R⁶ is C₁₋₆alkyl and R⁵ and R⁷ are independently C₁₋₆aralkyl.

In certain preferred embodiments, R¹, R², and R³ are all hydrogen, R⁶ and R⁸ are both isobutyl, R⁵ is phenylethyl, and R⁷ is phenylmethyl.

In certain embodiments, R⁵, R⁶, and R⁷ are independently selected from hydrogen, C₁₋₆alkyl, C₁₋₆hydroxyalkyl, C₁₋₆alkoxyalkyl, aryl, and C₁₋₆aralkyl, each of which is optionally substituted with a group selected from alkyl, amide, amine, carboxylic acid or a pharmaceutically acceptable salt thereof, carboxyl ester, thiol, and thioether. In certain embodiments, at least one of R⁵ and R⁷ is C₁₋₆aralkyl substituted with alkyl, more preferably substituted with perhaloalkyl. In certain such embodiments, R⁷ is C₁₋₆aralkyl substituted with trifluoromethyl.

In certain embodiments, Y is selected from N-alkyl, O, and CH₂. In certain such embodiments, Z is CH₂, and m and n are both 0. In certain alternative such embodiments, Z is CH₂, m is 0, and n is 2 or 3. In yet another alternative such embodiments, Z is O, m is 1, and n is 2.

In certain preferred embodiments, the chain of amino acids has a structure of formula (XIII)

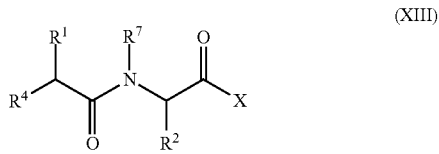

(XIII)

wherein each Ar is independently an aromatic or heteroaromatic group optionally substituted with 1 to 4 substituents;

each A is independently selected from C=O, C=S, and SO₂, preferably C=O; or

A is optionally a covalent bond when adjacent to an occurrence of Z;

B is absent or is N(R⁹)R¹⁰, preferably absent;

L is absent or is selected from C=O, C=S, and SO₂, preferably SO₂ or C=O;

M is absent or is C₁₋₁₂alkyl, preferably C₁₋₈alkyl;

Q is absent or is selected from O, NH, and N—C₁₋₆alkyl;

X is COOH or an activated form thereof, preferably X is COOH, COCl, or CON(Me)(OMe), most preferably X is COOH or COCl;

Y is absent or is selected from C=O and SO₂;

each Z is independently selected from O, S, NH, and N—C₁₋₆alkyl, preferably O; or Z is optionally a covalent bond when adjacent to an occurrence of A;

R¹ is selected from H, —C₁₋₆alkyl-B, C₁₋₆hydroxyalkyl, C₁₋₆alkoxyalkyl, aryl, and C₁₋₆aralkyl;

R² is selected from aryl, C₁₋₆aralkyl, heteroaryl, and C₁₋₆heteroaralkyl;

R⁴ is N(R⁵)L-Q-R⁶;

R⁵ is selected from hydrogen, OH, C₁₋₆aralkyl, and C₁₋₆alkyl, preferably hydrogen;

R⁶ is selected from hydrogen, C₁₋₆alkyl, C₁₋₆alkenyl, C₁₋₆alkynyl, Ar—Y—, carbocyclyl, heterocyclyl, an N-terminal protecting group, aryl, C₁₋₆aralkyl, heteroaryl, C₁₋₆heteroaralkyl, R¹¹ZAZ—C₁₋₈alkyl-, R¹⁴Z—C₁₋₈alkyl-, (R¹¹O)(R¹²O)P(=O)O—C₁₋₈alkyl-ZAZ—C₁₋₈alkyl-, R¹¹ZAZ—C₁₋₈alkyl-ZAZ—C₁₋₈alkyl-, heterocyclylMZAZ—C₁₋₈alkyl-, (R¹¹O)(R¹²O)P(=O)O—C₁₋₈alkyl-, (R¹³)₂N—C₁₋₁₂alkyl-, (R¹³)₃N⁺—C₁₋₁₂alkyl-, heterocyclylM-, carbocyclylM-, R¹⁴SO₂C₁₋₈alkyl-, and R¹⁴SO₂NH; preferably an N-capping group, more preferably t-butoxycarbonyl or benzyloxycarbonyl; or R⁵ and R⁶ together are C₁₋₆alkyl-Y—C₁₋₆alkyl, C₁₋₆alkyl-ZAZ—C₁₋₆alkyl, ZAZ—C₁₋₆alkyl-ZAZ—C₁₋₆alkyl, ZAZ—C₁₋₆alkyl-ZAZ, or C₁₋₆alkyl-A, thereby forming a ring;

R⁷ is selected from hydrogen, C₁₋₆alkyl, and C₁₋₆aralkyl, preferably hydrogen;

R⁹ is selected from hydrogen, OH, and C₁₋₆alkyl, preferably C₁₋₆alkyl; and

R¹⁰ is an N-terminal protecting group;

R¹¹ and R¹² are independently selected from hydrogen, metal cation, C₁₋₆alkyl, C₁₋₆alkenyl, C₁₋₆alkynyl, aryl, heteroaryl, C₁₋₆aralkyl, and C₁₋₆heteroaralkyl, preferably from hydrogen, metal cation, and $C_{1-6}$alkyl, or $R^{11}$ and $R^{12}$ together are $C_{1-6}$alkyl, thereby forming a ring;

each $R^{13}$ is independently selected from hydrogen and $C_{1-6}$alkyl, preferably $C_{1-6}$alkyl; and $R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that in any occurrence of the sequence ZAZ, at least one member of the sequence must be other than a covalent bond.

In certain embodiments, $R^1$ is selected from —$C_{1-6}$alkyl-B and $C_{1-6}$aralkyl. In certain such embodiments, $R^1$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain preferred such embodiments, $R^1$ is substituted with one or more substituents selected from carboxylic acid and ester. In certain embodiments, $R^1$ is selected from methyl, ethyl, isopropyl, carboxymethyl, and benzyl. In certain embodiments $R^1$ is —$C_{1-6}$ alkyl-B and $C_{1-6}$aralkyl. In certain preferred such embodiments, B is absent.

In certain embodiments, $R^2$ is selected from $C_{1-6}$aralkyl and $C_{1-6}$heteroaralkyl. In certain such embodiments, $R^2$ is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl, wherein the alkyl moiety may contain six, five, four, three, two, or one carbon atoms, preferably one or two. In certain such embodiments, $R^2$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^2$ is substituted with a substituent selected from alkyl, trihaloalkyl, alkoxy, hydroxy, or cyano. In certain such embodiments, $R^2$ is selected from $C_{1-6}$alkyl-phenyl and $C_{1-6}$alkyl-indolyl. In certain preferred such embodiments, $R^2$ is selected from

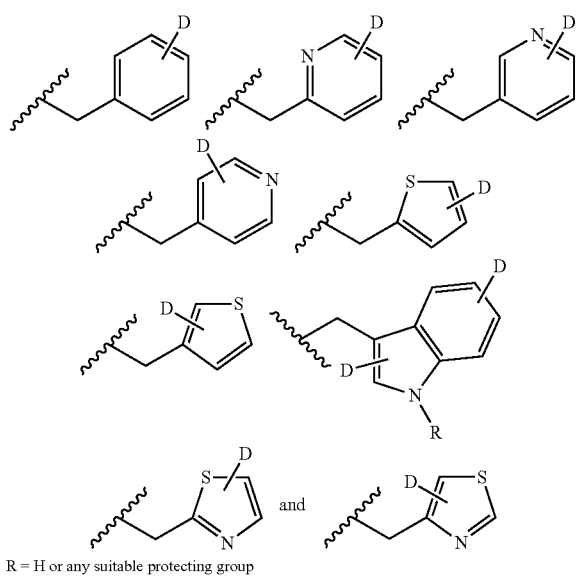

R = H or any suitable protecting group wherein D is selected from H, OMe, OBu′, OH, CN, $CF_3$ and $CH_3$. In certain embodiments D is selected from H, OMe, OH, CN, $CF_3$ and $CH_3$.

In certain preferred such embodiments where D is attached to a six-membered ring, D is attached at the 4-position relative to the point of attachment, preferably excluding embodiments where the 4-position of the ring is occupied by the nitrogen of a pyridine ring.

In certain embodiments, $R^5$ is hydrogen, L is C=O or $SO_2$, $R^6$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-E-, where E is selected from a direct bond, —O—, and $C_{1-6}$alkyl. In certain other such embodiments where Q is $C_{1-6}$alkyl, Q may be substituted, preferably with Ar, e.g., phenyl.

In certain embodiments, $R^5$ is hydrogen, Q is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Q is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, L and Q are absent and $R^6$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^5$ is $C_{1-6}$alkyl and $R^6$ is selected from butyl, allyl, propargyl, phenylmethyl, 2-pyridyl, 3-pyridyl, and 4-pyridyl.

In other embodiments, L is $SO_2$, Q is absent, and $R^6$ is selected from $C_{1-6}$alkyl and aryl. In certain such embodiments, $R^6$ is selected from methyl and phenyl.

In certain embodiments, L is C=O and $R^6$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{11}$ZA-$C_{1-8}$alkyl-, $R^{14}$Z—$C_{1-8}$alkyl-, $(R^{11}O)(R^{12}O)P(=O)O—C_{1-8}$alkyl-, $(R^{11}O)(R^{12}O)P(=O)O—C_{1-8}$alkyl-ZAZ—$C_{1-8}$alkyl-, $(R^{11}O)(R^{12}O)P(=O)O—C_{1-8}$alkyl-Z—$C_{1-8}$alkyl-, $R^{11}$ZA-$C_{1-8}$alkyl-ZAZ—$C_{1-8}$alkyl-, heterocyclylMZAZ—$C_{1-8}$alkyl-, $(R^{13})_2$N—$C_{1-8}$alkyl-, $(R^{13})_3N^+$—$C_{1-8}$alkyl-, heterocyclylM-, carbocyclylM-, $R^{14}SO_2C_{1-8}$alkyl-, and $R^{14}SO_2NH$—, wherein each occurrence of Z and A is independently other than a covalent bond. In certain embodiments, L is C=O, Q is absent, and $R^6$ is H.

In certain embodiments, $R^5$ is $C_{1-6}$alkyl, $R^6$ is $C_{1-6}$alkyl, Q is absent, and L is C=O. In certain such embodiments, $R^6$ is ethyl, isopropyl, 2,2,2-trifluoroethyl, or 2-(methylsulfonyl)ethyl.

In other embodiments, L is C=O, Q is absent, and $R^6$ is $C_{1-6}$aralkyl. In certain such embodiments, $R^6$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^5$ is $C_{1-6}$alkyl, and $R^6$ is aryl. In certain such embodiments, $R^6$ is substituted or unsubstituted phenyl.

In certain embodiments, L is C=O, Q is absent, and $R^6$ is selected from heteroaryl and $C_{1-6}$heteroaralkyl. In certain such embodiments, $R^6$ is heteroaryl selected from pyrrole, furan, thiophene, imidazole, isoxazole, oxazole, oxadiazole, thiazole, thiadiazole, triazole, pyrazole, pyridine, pyrazine, pyridazine and pyrimidine. In certain alternative such embodiments, $R^6$ is $C_{1-6}$heteroaralkyl selected from pyrrolylmethyl, furanylmethyl, thienylmethyl, imidazolylmethyl, isoxazolylmethyl, oxazolylmethyl, oxadiazolylmethyl, thiazolylmethyl, thiadiazolylmethyl, triazolylmethyl, pyrazolylmethyl, pyridylmethyl, pyrazinylmethyl, pyridazinylmethyl and pyrimidinylmethyl.

In certain embodiments, L is C=O, Q is absent or O, and $R^6$ is carbocyclylM-, wherein M is $C_{0-1}$alkyl. In certain such embodiments, $R^6$ is cyclopropyl or cyclohexyl.

In certain embodiments, L and A are C=O, Q is absent, Z is O, M is $C_{1-8}$alkyl, preferably methylene, and $R^6$ is selected from $R^{11}ZA-C_{1-8}$alkyl-, $R^{14}Z-C_{1-8}$alkyl-, $R^{11}ZA-C_{1-8}$alkyl-ZAZ-$C_{1-8}$alkyl-, $(R^{11}O)(R^{12}O)P(=O)O-C_{1-8}$alkyl-ZAZ-$C_{1-8}$alkyl-, $(R^{11}O)(R^{12}O)P(=O)O-C_{1-8}$alkyl-Z-$C_{1-8}$alkyl-, and heterocyclylMZAZ-$C_{1-8}$alkyl-, wherein each occurrence of A is independently other than a covalent bond. In certain such embodiments, $R^6$ is heterocyclylMZAZ-$C_{1-8}$alkyl- where heterocyclyl is substituted or unsubstituted oxodioxolenyl or $N(R^{16})(R^{17})$, wherein $R^{16}$ and $R^{17}$ together are $C_{1-6}$alkyl-Y-$C_{1-6}$alkyl, preferably $C_{1-3}$alkyl-Y-$C_{1-3}$alkyl, thereby forming a ring.

In certain preferred embodiments, L is C=O, Q is absent, M is $C_{1-8}$alkyl, and $R^6$ is selected from $(R^{11}O)(R^{12}O)P(=O)O-C_{1-8}$alkyl-, $(R^{13})_2NC_{1-8}$alkyl-, $(R^{13})_3N^+C_{1-8}$alkyl-, and heterocyclyl-M-. In certain such embodiments, $R^6$ is $(R^{13})_2NC_{1-8}$alkyl or $(R^{13})_3N^+C_{1-8}$alkyl-, where $R^{13}$ is $C_{1-6}$alkyl. In certain other such embodiments, $R^6$ is heterocyclylM-, where heterocyclyl is selected from morpholino, piperidino, piperazino, and pyrrolidino.

In certain embodiments, L is C=O, $R^5$ is $C_{1-6}$alkyl, Q is selected from O and NH and $R^6$ is selected from $C_{1-6}$alkyl, cycloalkyl-M, $C_{1-6}$aralkyl, and $C_{1-6}$heteroaralkyl. In other embodiments, L is C=O, $R^5$ is $C_{1-6}$alkyl, Q is selected from O and NH, and $R^6$ is $C_{1-6}$alkyl, where $C_{1-6}$alkyl is selected from methyl, ethyl, and isopropyl. In further embodiments, L is C=O, $R^5$ is $C_{1-6}$alkyl, Q is selected from O and NH and $R^6$ is $C_{1-6}$aralkyl, where aralkyl is phenylmethyl. In other embodiments, L is C=O, $R^5$ is $C_{1-6}$alkyl, Q is selected from O and NH, and $R^6$ is $C_{1-6}$heteroaralkyl, where heteroaralkyl is (4-pyridyl)methyl.

In certain embodiments, L is absent or is C=O, and $R^5$ and $R^6$ together are $C_{1-6}$alkyl-Y-$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^5$ and $R^6$ together are $C_{1-3}$alkyl-Y-$C_{1-3}$alkyl. In another preferred embodiment, L and Q are absent, and $R^5$ and $R^6$ together are $C_{1-3}$alkyl-Y-$C_{1-3}$alkyl. In another preferred embodiment, L is C=O, Q is absent, Y is selected from NH and N-$C_{1-6}$alkyl, and $R^5$ and $R^6$ together are $C_{1-3}$alkyl-Y-$C_{1-3}$alkyl. In another preferred embodiment, L is C=O, Y is absent, and $R^5$ and $R^6$ together are $C_{1-3}$alkyl-Y-$C_{1-3}$alkyl. In another preferred embodiment, L and A are C=O, and $R^5$ and $R^6$ together are $C_{1-2}$alkyl-ZA-$C_{1-2}$alkyl. In another preferred embodiment, L and A are C=O and $R^5$ and $R^6$ together are $C_{2-3}$alkyl-A.

In certain embodiments, $R^7$ is selected from hydrogen and $C_{1-6}$alkyl. In certain preferred such embodiments, $R^7$ is selected from hydrogen and methyl. In more preferred such embodiments, $R^7$ is hydrogen.

In certain embodiments, $R^2$ and $R^3$ are each independently $C_{1-6}$aralkyl, and $R^1$ is selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents.

In certain preferred embodiments, the chain of amino acids has a structure of formula (XIV)

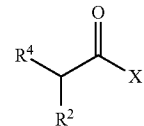

(XIV)

each Ar is independently an aromatic or heteroaromatic group optionally substituted with 1 to 4 substituents;

each A is independently selected from C=O, C=S, and $SO_2$, preferably C=O; or

A is optionally a covalent bond when adjacent to an occurrence of Z;

L is absent or is selected from C=O, C=S, and $SO_2$, preferably $SO_2$ or C=O;

M is absent or is $C_{1-12}$alkyl, preferably $C_{1-8}$alkyl;

Q is absent or is selected from O, NH, and N-$C_{1-6}$alkyl;

X is COOH or an activated form thereof, preferably X is COOH, COCl, or CON(Me)(OMe), most preferably X is COOH or COCl;

Y is absent or is selected from C=O and $SO_2$;

each Z is independently selected from O, S, NH, and N-$C_{1-6}$alkyl, preferably O; or Z is optionally a covalent bond when adjacent to an occurrence of A;

$R^2$ is selected from aryl, $C_{1-6}$aralkyl, heteroaryl, and $C_{1-6}$heteroaralkyl;

$R^4$ is $N(R^5)L-Q-R^6$;

$R^5$ is selected from hydrogen, OH, $C_{1-6}$aralkyl, and $C_{1-6}$alkyl, preferably hydrogen;

$R^6$ is selected from hydrogen, $C_{1-6}$alkyl, $C_{1-6}$alkenyl, $C_{1-6}$alkynyl, Ar-Y-, carbocyclyl, heterocyclyl, an N-terminal protecting group, aryl, $C_{1-6}$aralkyl, heteroaryl, $C_{1-6}$heteroaralkyl, $R^{11}ZAZ-C_{1-8}$alkyl-, $R^{14}Z-C_{1-8}$alkyl-, $(R^{11}O)(R^{12}O)P(=O)O-C_{1-8}$alkyl-ZAZ-$C_{1-8}$alkyl-, $R^{11}ZAZ-C_{1-8}$alkyl-ZAZ-$C_{1-8}$alkyl-, heterocyclylMZAZ-$C_{1-8}$alkyl-, $(R^{11}O)(R^{12}O)P(=O)O-C_{1-8}$alkyl-, $(R^{13})_2N-C_{1-12}$alkyl-, $(R^{13})_3N^+-C_{1-12}$alkyl-, heterocyclylM-, carbocyclylM-, $R^{14}SO_2C_{1-8}$alkyl-, and $R^{14}SO_2NH$; preferably an N-capping group, more preferably t-butoxycarbonyl or benzyloxycarbonyl; or $R^5$ and $R^6$ together are $C_{1-6}$alkyl-Y-$C_{1-6}$alkyl, $C_{1-6}$alkyl-ZAZ-$C_{1-6}$alkyl, ZAZ-$C_{1-6}$alkyl-ZAZ-$C_{1-6}$alkyl, ZAZ-$C_{1-6}$alkyl-ZAZ, or $C_{1-6}$alkyl-A, thereby forming a ring;

$R^9$ is selected from hydrogen, OH, and $C_{1-6}$alkyl, preferably $C_{1-6}$alkyl; and $R^{10}$ is an N-terminal protecting group;

$R^{11}$ and $R^{12}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{11}$ and $R^{12}$ together are $C_{1-6}$alkyl, thereby forming a ring;

each $R^{13}$ is independently selected from hydrogen and $C_{1-6}$alkyl, preferably $C_{1-6}$alkyl; and $R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{15}$ is selected from hydrogen, $C_{1-6}$alkyl, $C_{1-6}$hydroxyalkyl, $C_{1-6}$alkoxy, -C(O)OC_{1-6}alkyl, -C(O)NHC_{1-6}alkyl, and $C_{1-6}$aralkyl, preferably $C_{1-6}$alkyl and $C_{1-6}$hydroxyalkyl, more preferably methyl, ethyl, hydroxymethyl, and 2-hydroxyethyl;

provided that in any occurrence of the sequence ZAZ, at least one member of the sequence must be other than a covalent bond.

In certain embodiments, $R^2$ is selected from $C_{1-6}$aralkyl and $C_{1-6}$heteroaralkyl. In certain such embodiments, $R^2$ is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl, wherein the alkyl moiety may contain six, five, four, three, two, or one carbon atoms, preferably one or two. In certain such embodiments, $R^2$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^2$ is substituted with a substituent selected from alkyl, trihaloalkyl, alkoxy, hydroxy, or cyano. In certain such embodiments, $R^2$ is selected from $C_{1-6}$alkyl-phenyl and $C_{1-6}$alkyl-indolyl. In certain preferred such embodiments, $R^2$ is selected from

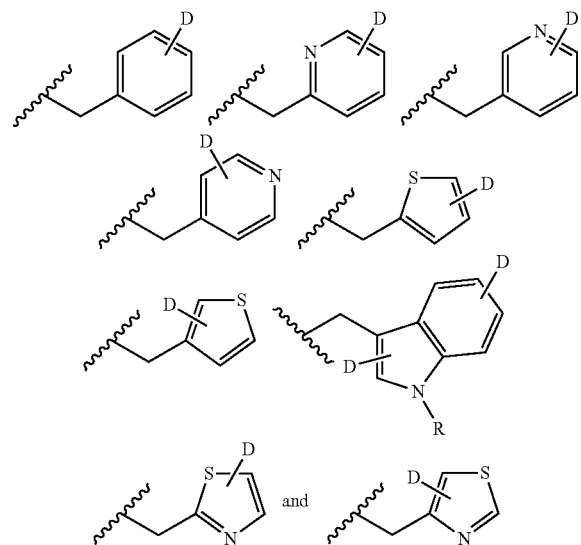

R = H or any suitable protecting group wherein D is selected from H, OMe, OBu$^t$, OH, CN, CF$_3$ and CH$_3$. In certain embodiments D is selected from H, OMe, OH, CN, CF$_3$ and CH$_3$.

In certain preferred such embodiments where D is attached to a six-membered ring, D is attached at the 4-position relative to the point of attachment, preferably excluding embodiments where the 4-position of the ring is occupied by the nitrogen of a pyridine ring.

In certain embodiments, $R^5$ is hydrogen, L is C=O or SO$_2$, $R^6$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-E-, where E is selected from a direct bond, —O—, and $C_{1-6}$alkyl. In certain other such embodiments where Q is $C_{1-6}$alkyl, Q may be substituted, preferably with Ar, e.g., phenyl.

In certain embodiments, $R^5$ is hydrogen, Q is absent, L is C=O or SO$_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or SO$_2$, Q is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, L and Q are absent and $R^6$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^5$ is $C_{1-6}$alkyl and $R^6$ is selected from butyl, allyl, propargyl, phenylmethyl, 2-pyridyl, 3-pyridyl, and 4-pyridyl.

In other embodiments, L is SO$_2$, Q is absent, and $R^6$ is selected from $C_{1-6}$alkyl and aryl. In certain such embodiments, $R^6$ is selected from methyl and phenyl.

In certain embodiments, L is C=O and $R^6$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{11}$ZA-$C_{1-8}$alkyl-, $R^{14}$Z—$C_{1-8}$alkyl-, $(R^{11}O)(R^{12}O)P(=O)O$—$C_{1-8}$alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, $R^{11}$ZA-$C_{1-8}$alkyl-ZAZ—$C_{1-8}$alkyl-, heterocyclylMZAZ—$C_{1-8}$alkyl-, $(R^{13})_2$N—$C_{1-8}$alkyl-, $(R^{13})_3$N$^+$—$C_{1-8}$alkyl-, heterocyclylM-, carbocyclylM-, $R^{14}$SO$_2$C$_{1-8}$alkyl-, and $R^{14}$SO$_2$NH—, wherein each occurrence of Z and A is independently other than a covalent bond. In certain embodiments, L is C=O, Q is absent, and $R^6$ is H.

In certain embodiments, $R^5$ is $C_{1-6}$alkyl, $R^6$ is $C_{1-6}$alkyl, Q is absent, and L is C=O. In certain such embodiments, $R^6$ is ethyl, isopropyl, 2,2,2-trifluoroethyl, or 2-(methylsulfonyl)ethyl.

In other embodiments, L is C=O, Q is absent, and $R^6$ is $C_{1-6}$aralkyl. In certain such embodiments, $R^6$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^5$ is $C_{1-6}$alkyl, and $R^6$ is aryl. In certain such embodiments, $R^6$ is substituted or unsubstituted phenyl.

In certain embodiments, L is C=O, Q is absent, and $R^6$ is selected from heteroaryl and $C_{1-6}$heteroaralkyl. In certain such embodiments, $R^6$ is heteroaryl selected from pyrrole, furan, thiophene, imidazole, isoxazole, oxazole, oxadiazole, thiazole, thiadiazole, triazole, pyrazole, pyridine, pyrazine, pyridazine and pyrimidine. In certain alternative such embodiments, $R^6$ is $C_{1-6}$heteroaralkyl selected from pyrrolylmethyl, furanylmethyl, thienylmethyl, imidazolylmethyl, isoxazolylmethyl, oxazolylmethyl, oxadiazolylmethyl, thiazolylmethyl, thiadiazolylmethyl, triazolylmethyl, pyrazolylmethyl, pyridylmethyl, pyrazinylmethyl, pyridazinylmethyl and pyrimidinylmethyl.

In certain embodiments, L is C=O, Q is absent or O, and $R^6$ is carbocyclylM-, wherein M is $C_{0-1}$alkyl. In certain such embodiments, $R^6$ is cyclopropyl or cyclohexyl.

In certain embodiments, L and A are C=O, Q is absent, Z is O, M is $C_{1-8}$alkyl, preferably methylene, and $R^6$ is selected from $R^{11}$ZA-$C_{1-8}$alkyl-, $R^{14}$Z—$C_{1-8}$alkyl-, $R^{11}$ZA-$C_{1-8}$alkyl-ZAZ—$C_{1-8}$alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, $R^6$ is heterocyclylMZAZ—$C_{1-8}$alkyl- where heterocyclyl is substituted or unsubstituted oxodioxolenyl or $N(R^{16})(R^{17})$, wherein $R^{16}$ and $R^{17}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, M is $C_{1-8}$alkyl, and $R^6$ is selected from $(R^{11}O)(R^{12}O)P(=O)O$—$C_{1-8}$alkyl-, $(R^{13})_2NC_{1-8}$alkyl, $(R^{13})_3N^+C_{1-8}$alkyl-, and heterocyclyl-M-. In certain such embodiments, $R^6$ is $(R^{13})_2NC_{1-8}$alkyl or $(R^{13})_3N^+C_{1-8}$alkyl-, where $R^{13}$ is $C_{1-6}$alkyl. In certain other such embodiments, $R^6$ is heterocyclylM-, where heterocyclyl is selected from morpholino, piperidino, piperazino, and pyrrolidino.

In certain embodiments, L is C=O, $R^5$ is $C_{1-6}$alkyl, Q is selected from O and NH and
$R^6$ is selected from $C_{1-6}$alkyl, cycloalkyl-M, $C_{1-6}$aralkyl, and $C_{1-6}$heteroaralkyl. In other embodiments, L is C=O, $R^5$ is $C_{1-6}$alkyl, Q is selected from O and NH, and $R^6$ is $C_{1-6}$alkyl, where $C_{1-6}$alkyl is selected from methyl, ethyl, and isopropyl. In further embodiments, L is C=O, $R^5$ is $C_{1-6}$alkyl, Q is selected from O and NH and $R^6$ is $C_{1-6}$aralkyl, where aralkyl is phenylmethyl. In other embodiments, L is C=O, $R^5$ is $C_{1-6}$alkyl, Q is selected from O and NH, and $R^6$ is $C_{1-6}$heteroaralkyl, where heteroaralkyl is (4-pyridyl)methyl.

In certain embodiments, L is absent or is C=O, and $R^5$ and $R^6$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^5$ and $R^6$ together are $C_{1-3}$alkyl-Y—$C_{1-3}$alkyl. In another preferred embodiment, L and Q are absent, and $R^5$ and $R^6$ together are $C_{1-3}$alkyl-Y—$C_{1-3}$alkyl. In another preferred embodiment, L is C=O, Q is absent, Y is selected from NH and N—$C_{1-6}$alkyl, and $R^5$ and $R^6$ together are $C_{1-3}$alkyl-Y—$C_{1-3}$alkyl. In another preferred embodiment, L is C=O, Y is absent, and $R^5$ and $R^6$ together are $C_{1-3}$alkyl-Y—$C_{1-3}$alkyl. In another preferred embodiment, L and A are C=O, and $R^5$ and $R^6$ together are $C_{1-2}$alkyl-ZA-$C_{1-2}$alkyl. In another preferred embodiment, L and A are C=O and $R^5$ and $R^6$ together are $C_{2-3}$alkyl-A.

In certain embodiments, $R^2$ is $C_{1-6}$aralkyl, and $R^1$ is selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents.

In certain preferred embodiments, the chain of amino acids has a structure of formula (XV)

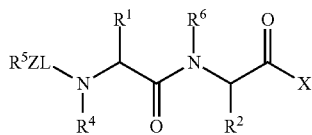

(XV)

wherein

L is selected from C=O, C=S, and $SO_2$, preferably C=O;

X is COOH or an activated form thereof, preferably X is COOH, COCl, or CON(Me)(OMe), most preferably X is COOH or COCl;

Z is absent, $C_{1-6}$alkyl, $C_{1-6}$alkoxy, or NR, e.g., absent, $C_{1-6}$alkyl, or $C_{1-6}$alkoxy, preferably absent;

R is selected from H and $C_{1-6}$alkyl, preferably H or $CH_3$;

$R^1$ and $R^2$ are each independently selected from hydrogen, $C_{1-6}$alkyl, $C_{2-6}$alkenyl, $C_{2-6}$alkynyl, $C_{1-6}$hydroxyalkyl, $C_{1-6}$alkoxyalkyl, aryl, $C_{1-6}$aralkyl, heteroaryl, heterocyclyl, $C_{1-6}$heterocycloalkyl, $C_{1-6}$heteroaralkyl, carbocyclyl, and $C_{1-6}$carbocyclolalkyl;

$R^4$ is selected from hydrogen, $C_{1-6}$aralkyl, and $C_{1-6}$alkyl;
$R^5$ is heteroaryl; and
$R^6$ is selected from hydrogen, $C_{1-6}$alkyl, and $C_{1-6}$aralkyl.

In certain embodiments, $R^1$ and $R^2$ are independently selected from hydrogen, $C_{1-6}$alkyl, $C_{1-6}$hydroxyalkyl, $C_{1-6}$alkoxyalkyl, $C_{1-6}$aralkyl, $C_{1-6}$heterocycloalkyl, $C_{1-6}$heteroaralkyl, and $C_{1-6}$carbocyclolalkyl. In certain embodiments, $R^1$ and $R^2$ are independently $C_{1-6}$alkyl selected from methyl, ethyl, propyl, isopropyl, butyl, sec-butyl, and isobutyl. In certain embodiments, $R^1$ and $R^2$ are independently $C_{1-6}$hydroxyalkyl. In certain preferred such embodiments, $R^1$ and $R^2$ are independently selected from hydroxymethyl and hydroxyethyl, preferably hydroxymethyl. In certain embodiments, $R^1$ and $R^2$ are independently $C_{1-6}$alkoxyalkyl. In certain such embodiments, $R^1$ and $R^2$ are independently selected from methoxymethyl and methoxyethyl, preferably methoxymethyl. In certain embodiments, $R^1$ and $R^2$ are independently $C_{1-6}$heteroaralkyl. In certain such embodiments, $R^1$ and $R^2$ are independently selected from imidazolylmethyl, pyrazolylmethyl, and thiazolylmethyl, and pyridylmethyl, preferably imidazol-4-ylmethyl, thiazol-4-ylmethyl, 2-pyridylmethyl, 3-pyridylmethyl, or 4-pyridylmethyl. In certain embodiments, $R^1$ and $R^2$ are independently $C_{1-6}$aralkyl. In certain such embodiments, $R^1$ and $R^2$ are independently selected from phenylmethyl (benzyl) and phenylethyl, preferably phenylmethyl. In certain embodiments, $R^1$ and $R^2$ are independently $C_{1-6}$carbocycloalkyl. In certain such embodiments $R^1$ is cyclohexylmethyl. In certain embodiments $R^1$ and $R^2$ are different. In certain embodiments, $R^1$ and $R^2$ are the same.

In certain embodiments, at least one of $R^1$ and $R^2$ is selected from $C_{1-6}$hydroxyalkyl and $C_{1-6}$alkoxyalkyl. In certain such embodiments, at least one of $R^1$ and $R^2$ is alkoxyalkyl. In certain embodiments, at least one of $R^1$ and $R^2$ is selected from methoxymethyl and methoxyethyl.

In certain embodiments, $R^4$ and $R^6$ are independently selected from hydrogen and methyl, preferably hydrogen.

In certain embodiments, $R^5$ is a 5- or 6-membered heteroaryl. In certain such embodiments, $R^5$ is selected from isoxazole, isothiazole, furan, thiophene, oxazole, thiazole, pyrazole, or imidazole, preferably isoxazole, furan, or thiazole.

In certain embodiments, $R^5$ is a bicyclic heteroaryl. In certain such embodiments bicyclic heteroaryl is selected from benzisoxazole, benzoxazole, benzothiazole, benzisothiazole.

In certain embodiments, L is C=O, Z is absent, and $R^5$ is a 1,3-thiazol-5-yl or 1,3-thiazol-4-yl. In certain such embodiments, when the thiazole is substituted, it is substituted at least at the 2-position. In other such embodiments, $R^5$ is an unsubstituted 1,3-thiazol-5-yl or 1,3-thiazol-4-yl.

In certain embodiments, L is C=O, Z is absent, and $R^5$ is a substituted 1,3-thiazol-5-yl. In certain such embodiments, $R^5$ is 1,3-thiazol-5-yl substituted with a substituent selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, $(C_{1-6}$alkyl$)_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl. In certain preferred such embodiments, $R^5$ is 1,3-thiazol-5-yl substituted with a substituent selected from methyl, ethyl, isopropyl, and cyclopropylmethyl.

In certain embodiments, L is C=O, Z is absent, and $R^5$ is a substituted 1,3-thiazol-4-yl. In certain such embodiments, $R^5$ is 1,3-thiazol-4-yl substituted with a substituent selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, $(C_{1-6}$alkyl$)_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl. In certain preferred such embodiments, $R^5$ is 1,3-thiazol-4-yl substituted with a substituent selected from methyl, ethyl, isopropyl, and cyclopropylmethyl.

In certain embodiments, L is C=O, Z is absent, and $R^5$ is an isoxazol-3-yl or isoxazol-5-yl. In certain preferred such embodiments, when the isoxazol-3-yl is substituted, it is substituted at least at the 5-position. In certain preferred embodiments, when the isoxazol-5-yl is substituted, it is substituted at least at the 3-position.

In certain embodiments, L is C=O, Z is absent, and $R^5$ is an unsubstituted isoxazol-3-yl.

In certain embodiments, L is C=O, Z is absent, and $R^5$ is a substituted isoxazol-3-yl. In certain such embodiments, $R^5$ is isoxazol-3-yl substituted with a substituent selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, $(C_{1-6}$alkyl$)_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl. In certain preferred such embodiments $R^5$ is isoxazole-3-yl substituted with a substituent selected from methyl, ethyl, isopropyl, and cyclopropylmethyl.

In certain embodiments L is C=O, Z is absent, and $R^5$ is isoxazol-3-yl substituted with a 4- to 6-membered nitrogen-containing $C_{1-6}$heterocycloalkyl. In certain such embodiments, $R^5$ is isoxazol-3-yl substituted with azetidinylmethyl, preferably azetidin-1-ylmethyl. In certain alternative such embodiments, L is C=O, Z is absent, and $R^5$ is isoxazol-3-yl substituted with

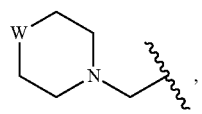

wherein W is O, NR, or $CH_2$, and R is H or $C_{1-6}$alkyl. In certain such embodiments, W is O.

In certain embodiments, L is C=O, Z is absent, and $R^5$ is isoxazol-3-yl substituted with 5-membered nitrogen-containing $C_{1-6}$heteroaralkyl, such as pyrazolylmethyl, imidazolylmethyl, triazol-5-ylmethyl, preferably 1,2,4-triazol-5-ylmethyl.

In certain embodiments, L is C=O, Z is absent, and $R^5$ is isoxazol-3-yl substituted with $C_{1-6}$alkoxy or $C_{1-6}$alkoxyalkyl, preferably methoxy, ethoxy, methoxymethyl, or methoxyethyl.

In certain embodiments, L is C=O, Z is absent, and $R^5$ is isoxazol-3-yl substituted with $C_{1-6}$hydroxyalkyl, preferably hydroxymethyl or hydroxyethyl.

In certain embodiments, L is C=O, Z is absent, and $R^5$ is isoxazol-3-yl substituted with a carboxylic acid, aminocarboxylate, $C_{1-6}$alkylaminocarboxylate, $(C_{1-6}$alkyl$)_2$aminocarboxylate, or $C_{1-6}$alkylcarboxylate. In certain such embodiments, $R^5$ is substituted with methyl carboxylate or ethyl carboxylate, preferably methyl carboxylate.

In certain embodiments, L is C=O, Z is absent, and $R^5$ is an unsubstituted isoxazol-5-yl.

In certain embodiments, L is C=O, Z is absent, and $R^5$ is a substituted isoxazol-5-yl. In certain such embodiments, $R^5$ is isoxazol-5-yl substituted with a substituent selected from $C_{1-6}$alkyl, $C_{1-6}$alkoxy, $C_{1-6}$alkoxyalkyl, $C_{1-6}$hydroxyalkyl, carboxylic acid, aminocarboxylate, $C_{1-6}$alkylaminocarboxylate, $(C_{1-6}$alkyl$)_2$aminocarboxylate, $C_{1-6}$alkylcarboxylate, $C_{1-6}$heteroaralkyl, $C_{1-6}$aralkyl, $C_{1-6}$heterocycloalkyl, and $C_{1-6}$carbocycloalkyl In certain preferred such embodiments $R^5$ is isoxazole-5-yl substituted with a substituent selected from methyl, ethyl, isopropyl, and cyclopropylmethyl.

In certain embodiments L is C=O, Z is absent, and $R^5$ is isoxazol-5-yl substituted with a 4- to 6-membered nitrogen-containing $C_{1-6}$heterocycloalkyl. In certain such embodiments, $R^5$ is isoxazol-5-yl substituted with azetidinylmethyl, preferably azetidin-1-ylmethyl. In certain alternative such embodiments, L is C=O, Z is absent, and $R^5$ is isoxazol-5-yl substituted with

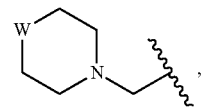

wherein W is O, NR, or $CH_2$, and R is H or $C_{1-6}$alkyl. In certain such embodiments, W is O.

In certain embodiments, L is C=O, Z is absent, and $R^5$ is isoxazol-5-yl substituted with 5-membered nitrogen-containing $C_{1-6}$heteroaralkyl, such as pyrazolylmethyl, imidazolylmethyl, triazol-5-ylmethyl, preferably 1,2,4-triazol-5-ylmethyl.

In certain embodiments, L is C=O, Z is absent, and $R^5$ is isoxazol-5-yl substituted with $C_{1-6}$alkoxy or $C_{1-6}$alkoxyalkyl, preferably methoxy, ethoxy, methoxymethyl, or methoxyethyl.

In certain embodiments, L is C=O, Z is absent, and $R^5$ is isoxazol-5-yl substituted with $C_{1-6}$hydroxyalkyl, preferably hydroxymethyl or hydroxyethyl.

In certain embodiments, L is C=O, Z is absent, and $R^5$ is isoxazol-5-yl substituted with a carboxylic acid, aminocarboxylate, $C_{1-6}$alkylaminocarboxylate, $(C_{1-6}$alkyl$)_2$aminocarboxylate, or $C_{1-6}$alkylcarboxylate. In certain such embodiments, $R^5$ is substituted with methyl carboxylate or ethyl carboxylate, preferably methyl carboxylate.

In certain embodiments, Z is NR, preferably NH.

Uses of Enzyme Inhibitors

Orderly protein degradation is crucial to the maintenance of normal cell functions, and the proteasome is integral to the protein degradation process. The proteasome controls the levels of proteins that are important for cell-cycle progression and apoptosis in normal and malignant cells; for example, cyclins, caspases, BCL2 and nF-kB (Kumatori et al., Proc. Natl. Acad. Sci. USA (1990) 87:7071-7075; Almond et al., Leukemia (2002) 16: 433-443). Thus, it is not surprising that inhibiting proteasome activity can translate into therapies to treat various disease states, such as malignant, non-malignant and autoimmune diseases, depending on the cells involved.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., J. Mol. Med. (1997) 75:5-17; Adams, Nature (2004) 4: 349-360). Therefore, certain embodiments of the invention relate to a method of treating cancers comprising administering to a subject in need of such treatment an effective amount of the proteasome inhibitor compound disclosed herein. As used herein, the term "cancer" includes, but is not limited to, blood born and solid tumors. Cancer refers to disease of blood, bone, organs, skin tissue and the vascular system, including, but not limited to, cancers of the bladder, blood, bone, brain, breast, cervix, chest, colon, endrometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-entero-pancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, the use of proteasome inhibitors for the treatment of such diseases is attractive and being examined (Cilloni et al., Haematologica (2007) 92: 1124-1229). CMPD can include chronic myelogenous leukaemia, chronic neutrophilic leukaemia, chronic eosinophilic leukaemia, polycythaemia vera, chronic idiopathic myelofibrosis, essential thrombocythaemia and unclassifiable chronic myeloproliferative disease. An aspect of the invention is the method of treating CMPD comprising administering to a subject in need of such treatment an effective amount of the proteasome inhibitor compound disclosed herein.

Myelodisplastic/myeloproliferative diseases, such as chronic myelomonocytic leukaemia, atypical chronic myeloid leukemia, juvenile myelomonocytic leukaemia and unclassifiable myelodysplastic/myeloproliferative disease, are characterized by hypercellularity of the bone marrow due to proliferation in one or more of the myeloid lineages. Inhibiting the proteasome with the composition described herein, can serve to treat these myelodisplatic/myeloproliferative diseases by providing a subject in need of such treatment an effective amount or the composition.

Myelodysplastic syndromes (MDS) refer to a group of hematopoietic stem cell disorders characterized by dysplasia and ineffective haematopoiesis in one or more of the major myeloid cell lines. Targeting NF-kB with a proteasome inhibitor in these hematologic malignancies induces apoptosis, thereby killing the malignant cell (Braun et al. Cell Death and Differentiation (2006) 13:748-758). A further embodiment of the invention is a method to treat MDS comprising administering to a subject in need of such treatment an effective amount of the compound disclosed herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del(5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extrcutaneous mastocytoma. Another embodiment of the invention is a method to treat mastocytosis comprising administering an effect amount of the compound disclosed herein to a subject diagnosed with mastocytosis.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Thus, in certain embodiments, the invention relates to methods of affecting the level of expression of IL-2, MHC-I, IL-6, TNFα, IFN-β or any of the other previously-mentioned proteins, each method comprising administering to a subject an effective amount of a proteasome inhibitor composition disclosed herein. In certain embodiments, the invention includes a method of treating an autoimmune disease in a mammal comprising administering a therapeutically effective amount of the compound described herein. An "autoimmune disease" herein is a disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoinimune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation or present unfamiliar peptides on their surface. Intracellular proteolysis generate small peptides for presentation to T-lymphocytes to induce MHC class I-mediated immune responses. Thus, in certain embodiments, the invention relates to a method of using the compound as an immunomodulatory agent for inhibiting or altering antigen presentation in a cell, comprising exposing the cell (or administering to a subject) to the compound described herein. Specific embodiments include a method of treating graft or transplant-related diseases, such as graft-versus-host disease or host versus-graft disease in a mammal, comprising administering a therapeutically effective amount of the compound described herein. The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart. liver, spleen, pancreas, thyroid lobe. lung, kidney, tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same mammal. Preferably the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. Cancer Res. (2006) 66:5461-5468). Thus, another embodiment of the invention comprises administering an effective amount of the composition disclosed herein to a subject with histiocytic or dendritic cell neoplasm. Histiocytic and dindritirc cell neoplasms include histiocytic sarcoma, Langerhans cell histiocytosis, Langerhans cell sarcoma, interdigitating dendritic cell sarcoma/tumor, follicular dendritic cell sarcoma/tumor and non-specified dendritic cell sarcoma.

Inhibition of the proteasome has been shown to be beneficial to treat diseases whereby a cell type is proliferating and immune disorders; thus, an embodiment of the invention includes the treatment of lymphoproliferative diseases (LPD) associated with primary immune disorders (PID) comprising administering an effective amount of the disclosed compound to a subject in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in patients who have received solid organ or bone marrow allografts, and iatrogenis immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Additional embodiments of the invention relate to methods for affecting the proteasome-dependent regulation of oncoproteins and methods of treating or inhibiting cancer growth, each method comprising exposing a cell (in vivo, e.g., in a subject, or in vitro) to the proteasome inhibitor composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. In certain embodiments, the invention relates to a method for treating p53-related apoptosis, comprising administering to a subject an effective amount of a proteasome inhibitor composition disclosed herein.

Another aspect of the invention relates to the use of proteasome inhibitor compositions disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating poly-neuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., *Fed. Eur. Biochem. Soc.*, (1992) 304: 57-60). The APP-processing enzyme cleaves at the $Gln^{15}$--$Lys^{16}$ bond; in the presence of calcium ion, the enzyme also cleaves at the Met-$^1$--$Asp^1$ bond, and the $Asp^1$--$Ala^2$ bonds to release the extracellular domain of β-AP.

One aspect of the invention, therefore, relates to a method of treating Alzheimer's disease, comprising administering to a subject an effective amount of the proteasome inhibitor composition disclosed herein. Such treatment includes reducing the rate of β-AP processing, reducing the rate of β-AP plaque formation, reducing the rate of β-AP generation, and reducing the clinical signs of Alzheimer's disease.

Fibrosis is the excessive and persistent formation of fibrous connective tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity (Xu et al., 2000). However, accelerated degradation of the TGF-β signaling components has been observed in fibrotic conditions, such as cystic fibrosis, injection fibrosis, endomyocardial fibrosis, idiopathic pulmonary fibrosis, myelofibrosis, retroperitoneal fibrosis, progressive massive fibrosis, nephrogenic systemic fibrosis. Other conditions that are often associated with fibrosis include cirrhosis, diffuse parenchymal lung disease, postvasectomy pain syndrome, tuberculsis, sickle-cell anemia and rheumatoid arthritis. An embodiment of the invention is the method of treating a fibrotic or fibrotic-associated condition comprising administering an effective amount of the composition described herein to a subject in need of such treatment.

The treatment of burn victims is often hampered by fibrosis, thus, in certain embodiments, the invention relates to the topical or systemic administration of the inhibitors to treat burns. Wound closure following surgery is often associated with disfiguring scars, which may be prevented by inhibition of fibrosis. Thus, in certain embodiments, the invention relates to a method for the prevention or reduction of scarring.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, the proteasome inhibitor composition may be used for the inhibition of TNFα to prevent and/or treat septic shock.

Ischemia and reperfusion injury results in hypoxia, a condition in which there is a deficiency of oxygen reaching the tissues of the body. This condition causes increased degradation of Iκ-Bα, thereby resulting in the activation of NF-κB (Koong et al., 1994). It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of the proteasome inhibitor compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science*, (1995) 267:960). In certain embodiments, the invention relates to a method for inhibiting or reducing HIV infection in a subject, or a method for decreasing the level of viral gene expression, each method comprising administering to the subject an effective amount of the proteasome inhibitor composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-

12920, 2005). In addition to HBV, other hepatitis viruses (A, C, D and E) may also utilize the ubiquitin-proteasome degradation pathway for secretion, morphogenesis and pathogenesis. Accordingly, in certain embodiments, the invention relates to a method for treating viral infection, such as SARS or hepatitis A, B, C, D and E, comprising contacting a cell with (or administering to a subject) an effective amount of the compound disclosed herein.

In certain embodiments, the disclosed compositions may be useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, *entamoeba* species have been shown to lose encystation capacity when exposed to proteasome inhibitors (Gonzales, et al., Arch. Med. Res. 1997, 28, Spec No: 139-140). In certain such embodiments, the administrative protocols for the proteasome inhibitor compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed proteasome inhibitor compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds that act as proteasome inhibitors in the treatment of parasitic diseases are described in WO 98/10779, which is incorporated herein in its entirety.

In certain embodiments, the proteasome inhibitor compositions inhibit proteasome activity in a parasite without recovery in red blood cells and white blood cells. In certain such embodiments, the long half-life of blood cells may provide prolonged protection with regard to therapy against recurring exposures to parasites. In certain embodiments, the proteasome inhibitor compositions may provide prolonged protection with regard to chemoprophylaxis against future infection.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the 3-subunits. Thus, an embodiment of this invention relates to a method of treating prokaryotic infections, comprising administering to a subject an effective amount of the proteasome inhibitor composition disclosed herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed proteasome inhibitor composition may be useful in the treatment and/or prevention of diseases associated with bone loss, such as osteoporosis.

Thus, in certain embodiments, the invention relates to a method for treating a disease or condition selected from cancer, autoimmune disease, graft or transplant-related condition, neurodegenerative disease, fibrotic-associated condition, ischemic-related conditions, infection (viral, parasitic or prokaryotic) and diseases associated with bone loss, comprising administering a crystalline compound of Formula (II).

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microcapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

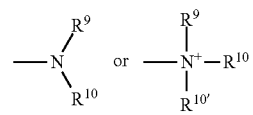

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The terms "amide" and "amido" are art-recognized as an amino-substituted carbonyl and includes a moiety that can be represented by the general formula:

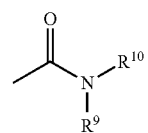

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

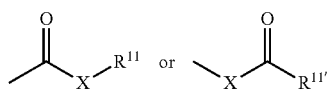

wherein X is a bond or represents an oxygen or a sulfur, and $R^{11}$ represents a hydrogen, an alkyl, an alkenyl, $-(CH_2)_m-R^8$ or a pharmaceutically acceptable salt, $R^{11'}$ represents a hydrogen, an alkyl, an alkenyl or $-(CH_2)_m-R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$hydroxyalkyl" refers to a $C_{1-6}$alkyl group substituted with a hydroxy group.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "proteasome" as used herein is meant to include immuno- and constitutive proteasomes.

The term "substantially pure" as used herein, refers to a crystalline polymorph that is greater than 90% pure, meaning that contains less than 10% of any other compound, including the corresponding amorphous compound. Preferably, the crystalline polymorph is greater than 95% pure, or even greater than 98% pure.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

EXEMPLIFICATION
Example 1
Synthesis of Compound 1
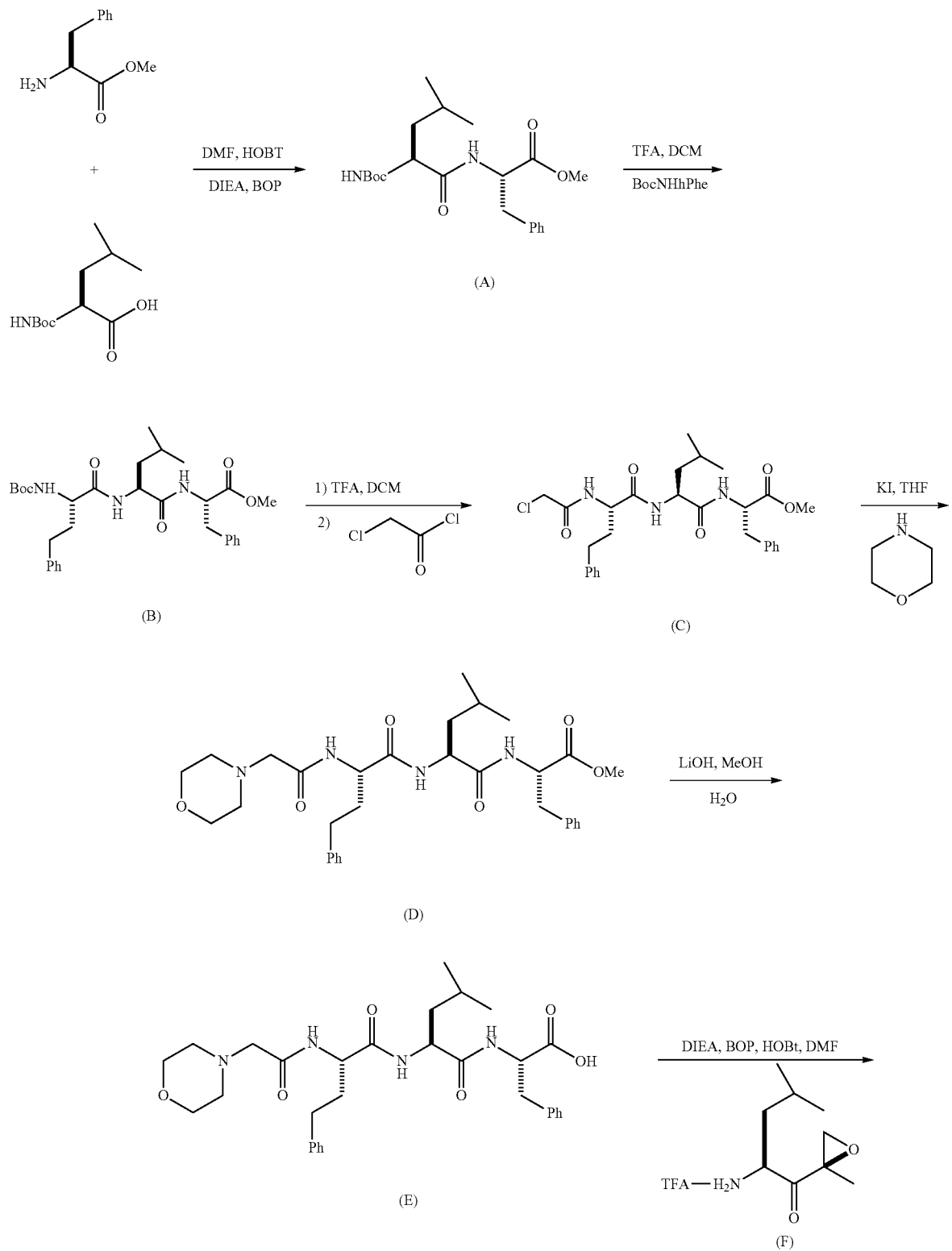

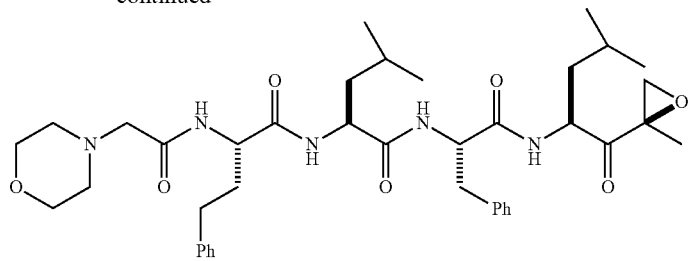

Synthesis of (B)

Hydroxybenztriazole (HOBT) (10.81 g, 80.0 mmol) and DIEA (200.0 mmol, 25.85 g, 35 mL) was added to a solution of NBoc leucine (50.0 mmol, 11.56 g) and phenylalanine methyl ester (50.0 mmol, 10.78 g) in 500 mL of DMF. The mixture was cooled to 0° C. in an ice-water bath and benzotriazol-1-yloxytris(dimethylamino)-phosphonium hexafluorophosphate (BOP) (80.0 mmol, 35.38 g) was added in several portions over five minutes. The reaction was placed under an atmosphere of argon and stirred overnight. The reaction was diluted with brine (1000 mL) and extracted with EtOAc (5×200 mL). The organic layers were combined and washed with water (10×100 mL) and brine (2×150 mL) and dried over $MgSO_4$. The $MgSO_4$ was removed by filtration and the volatiles removed under reduced pressure to give (A) (18.17 g). To a 50 mL 0° C. cooled solution of 80% TFA/DCM was added BocNHLeuPheOMe (45.86 mmol, 18.0 g). The solution was stirred and allowed to warm to room temperature over 2 hr. The volatiles were removed under reduced pressure to give an oil. BocNHhPhe (45.86 mmol, 12.81 g), DMF (500 mL), HOBT (73.37 mmol, 9.91 g) and DIEA (183.44 mmol, 23.70 g, 32.0 mL) were then added to the oil. The mixture was cooled to 0° C. in an ice-water bath and BOP (73.37 mmol, 32.45 g) was added in several portions over five minutes. The reaction was placed under argon and allowed to warm to room temperature overnight. The reaction was diluted with $H_2O$ (1500 mL) and extracted with DCM (5×300 mL). The organic layers were combined and washed with $H_2O$ (6×300 mL) and brine (1×300 mL) and dried over $MgSO_4$. The $MgSO_4$ was removed by filtration and the volatiles removed under reduced pressure to give a yellow solid. EtOH (200 mL, 95%) was then added to the yellow solid and the mixture was heated to 65° C. to dissolve all of the solids. The solution was then added to 1000 mL of chilled $H_2O$ and the resulting precipitate collected to give (B) (21.59 g).

Synthesis of (C)

(B) (1.80 mmol, 1.0 g) was mixed with TFA/DCM (80%) and was stirred at room temperature for 1 hr, at which time the mixture was concentrated and placed under high vacuum for 2 hr giving the TFA salt of the tri-peptide amine. To a 0° C. solution of the TFA salt (1.80 mmol) in DMF (10 mL) was added DIEA (3.6 mmol, 0.7 mL) followed by chloroacetyl chloride (2.7 mmol, 0.215 mL). The reaction was allowed to warm to RT while stirring overnight under an atmosphere of nitrogen. The mixture was then diluted with brine (15 mL) and extracted with EtOAc (3×15 mL). The organic layers were combined, washed with $H_2O$ (2×15 mL) and brine (2×15 mL) and dried over $Na_2SO_4$. The $Na_2SO_4$ was removed by filtration and the volatiles removed under reduced pressure. The crude material was suspended in EtOAc and filtered to give (C) (0.640 g)

Synthesis of (D)

KI (0.019 mmol, 0.0032 g) and morpholine (0.110 mmol, 0.0096 g) were added to a solution of (C) (0.094 mmol, 0.050 g) in THF (10 mL) and the mixture was stirred overnight under an atmosphere of nitrogen. The volatiles were removed under reduced pressure and the crude material taken up in EtOAc (15 mL), washed with $H_2O$ (2×10 mL) and brine (2×10 mL) and dried over $MgSO_4$. The $MgSO_4$ was removed by filtration and the volatiles removed under reduced pressure to give (D).

Synthesis of (E)

LiOH (0.94 mmol, 0.023 g) was added to a slurry of (D) (0.094 mmol) in 4 mL of 3:1 $MeOH/H_2O$ cooled to 0° C. After 12 hr at 5° C. the reaction was quenched with 20 mL sat. $NH_4Cl$ and diluted further with 10 mL $H_2O$. The pH of the reaction mixture was adjusted to 3 with 1 N HCl, extracted with DCM (3×15 mL), and dried over $MgSO_4$. The $MgSO_4$ was removed by filtration and the volatiles were removed under reduced pressure to give (E).

Synthesis of Compound 1

(E) (0.082 mmol, 0.046 g), DIEA (0.328 mmol, 0.057 mL) and HOBT (0.133 mmol, 0.018 g) were added to a stirred solution of (F) (0.082 mmol) in DMF (2 mL). The mixture was cooled to 0° C. in an ice bath and BOP (0.131 mmol, 0.058 g) was added in several portions. The mixture was stirred at 5° C. under an atmosphere of argon overnight. The reaction was then diluted with $H_2O$ (15 mL) and extracted with EtOAc. The organic layer was washed with water, sat. $NaHCO_3$, and brine and dried over anhydrous $MgSO_4$. The $MgSO_4$ was removed by filtration and the volatiles removed under reduced pressure to give compound 1 (0.034 g) ($IC_{50}$ 20S CT-L<100 nM; $IC_5$s Cell-Based CT-L<100 nM).

Example 2

Compound 1 (1.0 g) was dissolved in methanol (16 mL) heated to 80° C. Water (4 mL) was then slowly added and the clear solution was allowed to cool to ambient temperature and the solution was brought to supersaturation by evaporating off 10 mL of solvent with compressed air. The resulting crystals were filtered, washed with 8 mL 1:1 deionized water-methanol, and dried under vacuum for 12 hours to provide crystalline compound 1 (0.9 g) with a melting point of 212° C.

The characteristic DSC curve of the sample is shown in FIG. 1 as recorded on a TA Instruments Differential Scanning Calorimeter 2920 at a heating rate of 10° C./minute.

Example 3

Compound 1 (1.0 g) was dissolved in acetonitrile (17 mL) heated to 80° C. Water (8 mL) was then slowly added and the clear solution was allowed to cool to ambient temperature and the solution was brought to supersaturation by evaporating off 10 mL of solvent with compressed air. The resulting crystals were filtered, washed with 8 mL 1:1 deionized water-acetonitrile, and dried under vacuum for 12 hours to provide crystalline compound 1 (0.85 g) with a melting point of 212° C.

Example 4

Compound 1 (1.0 g) was dissolved in ethanol (17 mL) heated to 80° C. Water (5 mL) was then slowly added and the clear solution was allowed to cool to ambient temperature and the solution was brought to supersaturation by evaporating off 15 mL of solvent with compressed air. The resulting crystals were filtered, washed with 8 mL 1:1 deionized water-ethanol, and dried under vacuum for 12 hours to provide crystalline compound 1 (0.82 g) with a melting point of 212° C.

Example 5

Compound 1 (1.0 g) was dissolved in ethyl acetate (30 mL) heated to 80° C. Water (5 mL) was then slowly added and the clear solution was allowed to cool to ambient temperature and the solution was brought to supersaturation by evaporating off 20 mL of solvent with compressed air. The resulting crystals were filtered, washed with 5 mL ethyl acetate, and dried under vacuum for 12 hours to provide crystalline compound 1 (0.60 g) with a melting point of 212° C.

Example 6

Compound 1 (1.0 g) was dissolved in ethanol (15 mL) heated to 80° C. Water (5 mL) was then slowly added and the clear solution was allowed to cool to ambient temperature and the solution was brought to supersaturation by evaporating off 10 mL of solvent with compressed air. The resulting crystals were filtered, washed with 10 mL 1:1 deionized water-ethanol, and dried under vacuum for 12 hours to provide crystalline compound 1 (0.54 g) with a melting point of 212° C.

Example 7

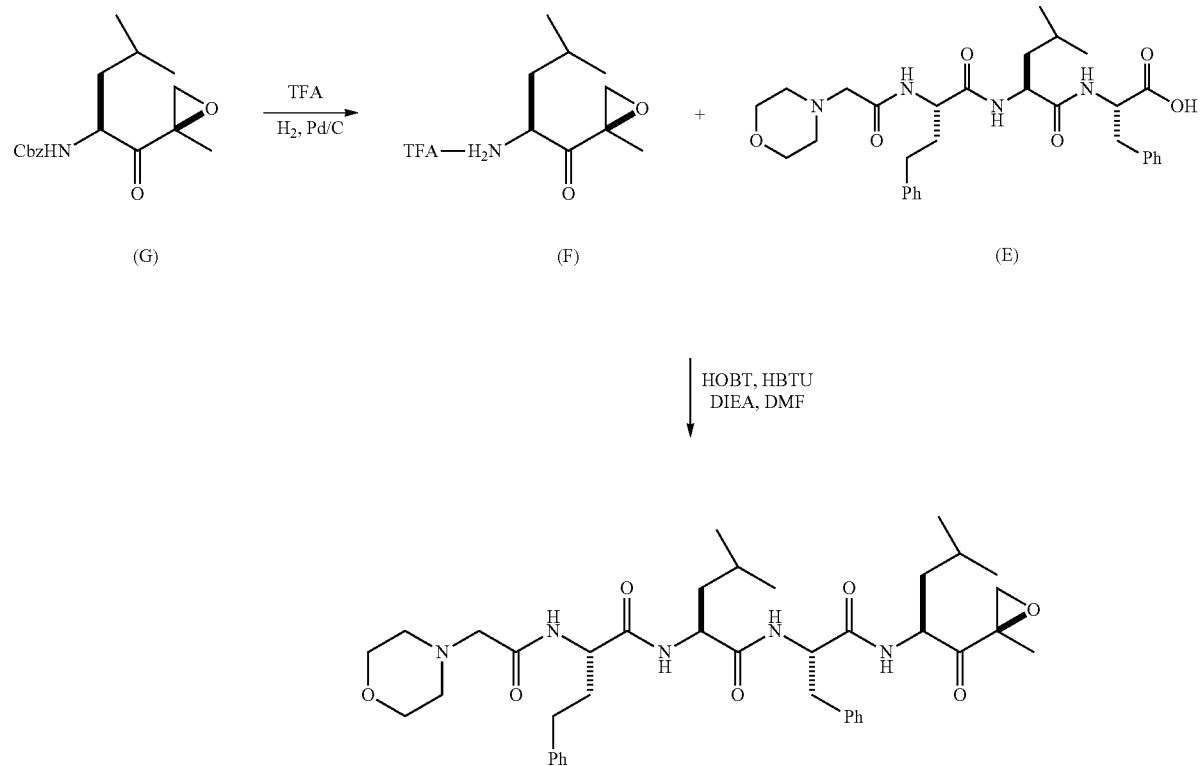

Synthesis of (F)

Compound (G) (0.43 g) was prepared according to U.S. Pat. Application No. 2005-0256324 and was added to a flask along with Pd/C (10% wt, 0.10 g) followed by slow addition of TFA (35 mL). The flask was evacuated and back-flushed with hydrogen gas three times and then the reaction mixture was stirred under one atmosphere of hydrogen at room temperature for two hours. The reaction mixture was then filtered through Celite and the filtrate was concentrated under reduced pressure. Dichloromethane (25 mL) was added and the volatiles removed under reduced pressure. The resultant thick yellow syrup was dried under high vacuum to a constant weight. The syrup was then transferred to 50 mL volumetric flask and rinsed with 8.5 mL diethyl ether to yield crystalline compound (F) (0.33 g).

Synthesis of Compound 1

A 10 mL volumetric flask was charged with 1-hydroxybenzotriazole (HOBT, 0.54 g) and N,N,N',N'-tetramethyl-O-(1H-benzotriazol-1-yl)uronium hexafluorophosphate (HBTU, 1.54 g) and diluted to 50 mL with DMF. This stock solution of coupling reagents was 0.40 M for both HOBT and HBTU.

(E) (0.61 g), (F) (0.33 g), and the coupling reagent stock solution (2.7 mL), were added to a 10 mL volumetric flask and the mixture was cooled to 0° C. DIEA (0.56 mL) was then added dropwise to the cooled solution. The mixture was allowed to stir at 0° C. for 60 minutes and was then quenched by the addition of saturated sodium bicarbonate (15 mL). The mixture was diluted with ethyl acetate (35 mL) and the layers separated. The organic layer was washed saturated sodium bicarbonate (3×15 mL), brine (2×15 mL) and dried over sodium sulfate. The sodium sulfate was removed by filtration and the volatiles removed under reduced pressure to give a thick syrup which was further dried under high vacuum to give a crude compound 1 as a foam (0.59 g).

Example 8

Crude compound 1 (0.590 g) was completely dissolved in methanol (11 mL) by stirring and heating in an oil bath (80° C.) and deionized water (17 mL) was added dropwise. The mixture was seeded with crystalline compound 1, stirred and allowed to slowly evaporate for 12 hours to approximately 20 mL to precipitate compound 1. The suspension was filtered, washed with 1:1 deionized water-methanol (4 mL), and dried under vacuum for 12 hours at room temperature to yield compound 1 as a white solid (0.25 g). The crystallization was repeated two additional times to yield crystalline compound 1 (0.13 g).

Crystalline compound 1 (0.3 g) was dissolved in isopropanol (15 mL) by stirring and heating in an oil bath (80° C.). The solution was concentrated under reduced pressure to reduce volume to 5 mL. Deionized water (20 mL) was quickly added and the resultant suspension was rigorously stirred for 1 hour. The glassy precipitate was filtered, rinsed with deionized water (25 mL) and dried to yield amorphous Compound 1 (0.3 g).

Figure 7:
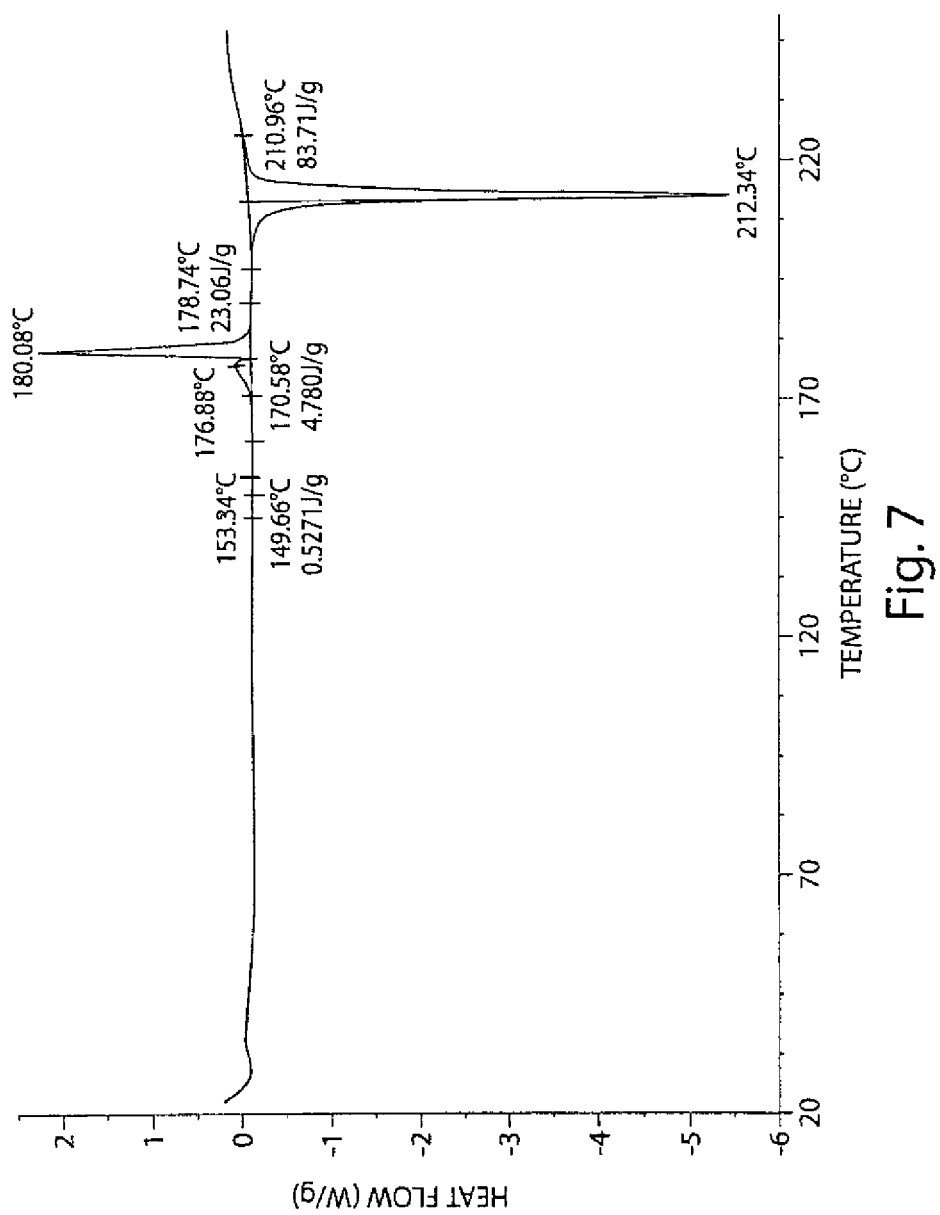
FIG. 7 shows a DSC curve of an amorphous sample of compound 1.

The characteristic DSC curve of the amorphous sample is shown in FIG. 7 which was recorded on a TA Instruments Differential Scanning Calorimeter 2920 at a heating rate of 1° C./minute for the amorphous form of Compound 1.

Figure 8:
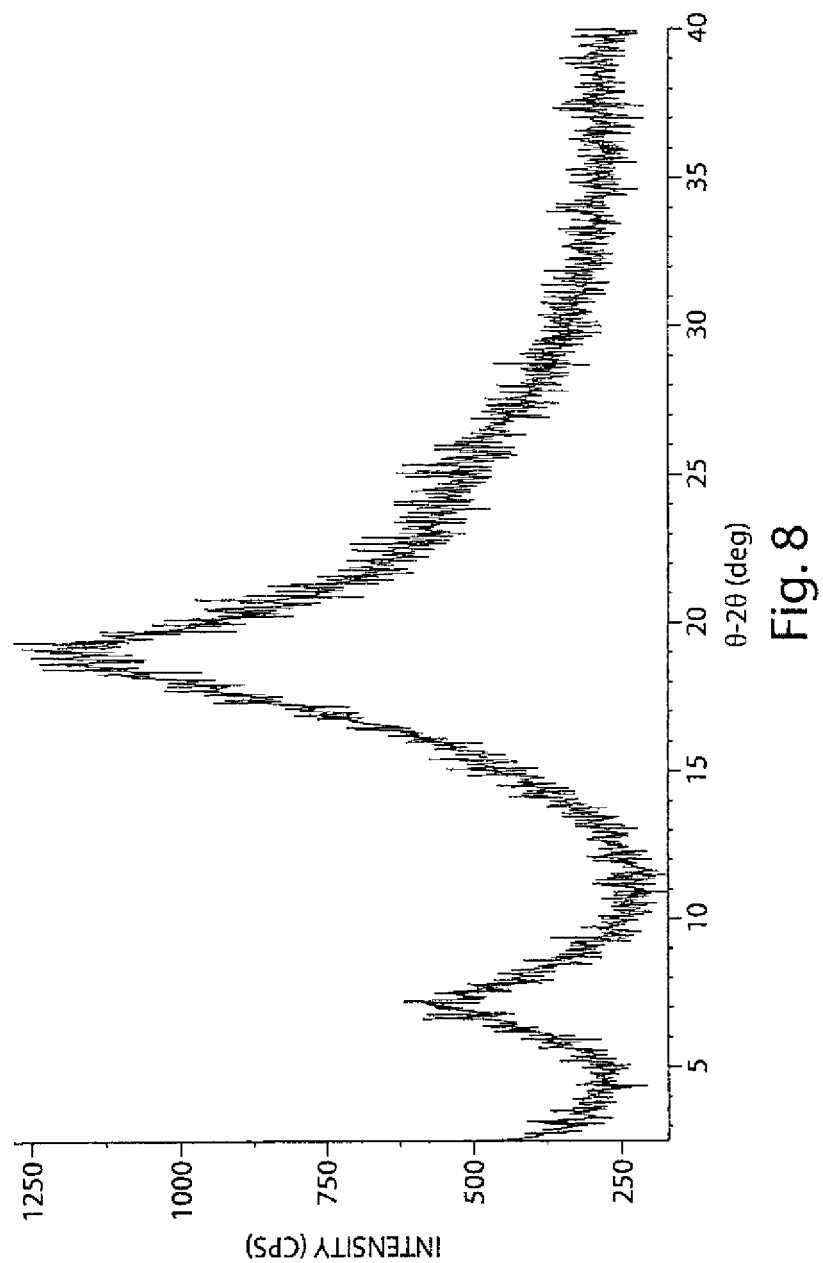
FIG. 8 shows the XRPD pattern of amorphous compound 1.

The characteristic X-ray diffraction pattern of the amorphous powder is shown in FIG. 8 and was recorded on the Shimadzu XRD-6000 under Cu Kα radiation [voltage and current set at 40 kV and 40 mA; divergence and scattering slits set at 10 and receiving slit set at 0.15 mm; NaI scintillation detector used for diffracted radiation; a θ-2θ continuous scan at 3°/min (0.4 sec/0.02° step) from 2.5 to 40° 2θ was used; samples were placed in an aluminum holder with silicon insert; and data collected and analyzed with XRD-6100/7000 v.5.0].

Example 9

Synthesis of (F)

A flask was charged with (G) and ethyl acetate (400 mL) and the solution was cooled in an ice bath for 15 minutes with stirring. Trifluoroacetic acid (200 mL) was added dropwise, maintaining an internal temperature of less than 10° C. Pd/C (3.6 g) was added in one portion and the flask was purged under high vacuum and refilled with hydrogen three times. After 2 hours, the reaction was filtered through Celite and the filtrate evaporated under reduced pressure to a thick orange oil which was swirled gently with 170 mL diethyl ether. As the flask was swirled, fine crystals formed. The flask was allowed to sit at room temperature, and rapid crystallization occurred. After 1 hour at ambient temperature, the flask was capped tightly and placed in the freezer overnight (<−5° C.). The resulting crystalline solid was filtered and washed with ice cold ethyl ether (50 mL) and dried under high vacuum. Fine white crystals (14.1 g; melting point: 137° C.) of (F) were obtained.

Synthesis of Compound 1

A flask was charged with (F) (10 g), (E) (15.3 g), HBTU (15.3 g), HOBt (5.5 g), and DMF (300 mL). The mixture was stirred vigorously until dissolved and was placed in an NaCl/ice bath (−5° C.). After 15 minutes, DIEA (7.1 mL) was added dropwise over <10 minutes, maintaining an internal temperature of less than −3° C. After addition was complete, the reaction mixture was stirred in the bath for one hour and was quenched by addition of saturated NaHCO$_3$ (aq.) (200 mL). The slurry was extracted with ethyl acetate (1.5 L) and the organic layer was washed with sat. NaHCO$_3$ (aq.) (2×300 mL) and sat. NaCl (aq.) (200 mL), and then dried over MgSO$_4$.

The organic layer was concentrated to ~50 mL under reduced pressure and methylethyl ketone (200 mL) was added, and the solution was again concentrated to ~50 mL. Methylethyl ketone (125 mL) was added again, and the solution was stirred in an oil bath (80° C.) until clear. The solution was then allowed to cool and was seeded with pure crystalline Compound 1. The mixture was stirred for 2 hours at 25° C. and then overnight at 0° C. The white solid precipitate was filtered and washed with ice cold methylethyl ketone (300 mL) to give white solids. The solid was dried under high vacuum at ambient temperature to a constant weight to yield 13.5 g of pure compound 1.

Example 10

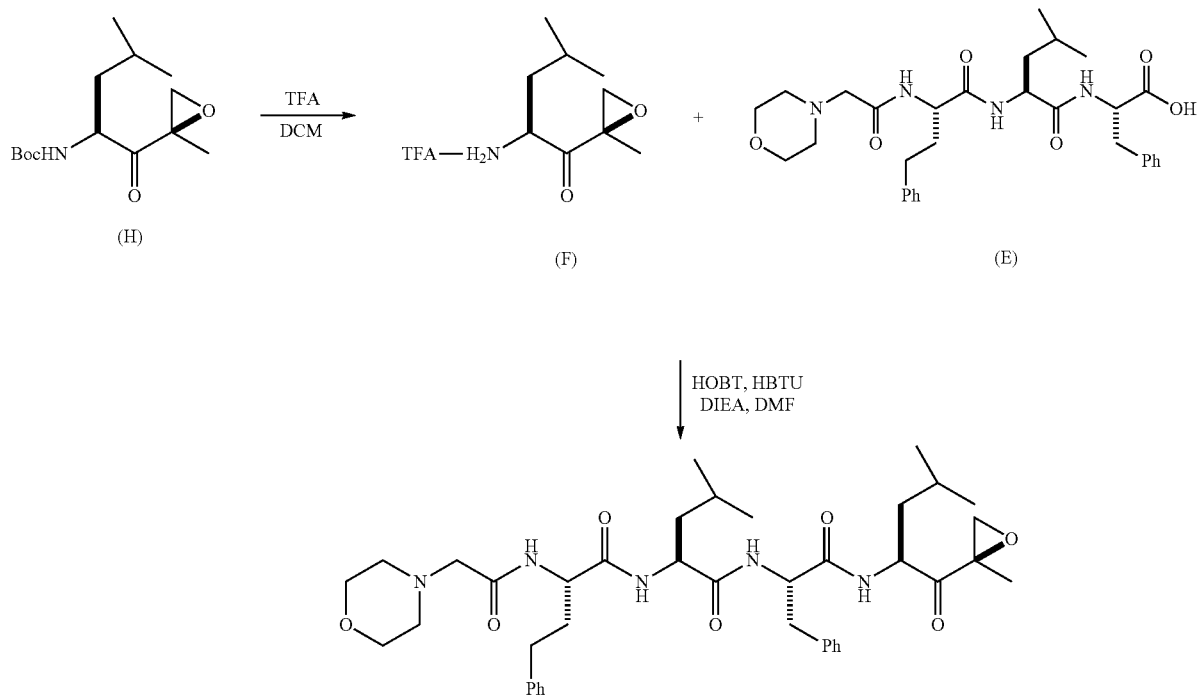

Synthesis of (F)

A flask was charged with (H) (100 g) [see: Bioorg. Med. Chem. Letter 1999, 9, 2283-88], and dichloromethane (300 mL) under nitrogen and the solution was cooled in an ice bath to 0-5° C. Trifluoroacetic acid (136.9 mL) was added dropwise with stirring at 0-10° C., after which the reaction mixture was removed from the ice bath and stirred at room temperature for 2 hours. Methyl tert-butyl ether (300 mL) was then added and 400 mL of solvent was evaporated under reduced pressure. MTBE (200 mL) was then added via addition funnel and the solution stirred for 20 minutes at 20° C., then heptanes (1000 mL) were added within 10 minutes and the reaction mixture cooled to 0-5° C. The reaction mixture was stirred for 30 minutes and then the solids were filtered, rinsed with cold heptanes (0-5° C., 3×100 mL) and dried under high vacuum to the constant weight to yield 90.69 g of (F) as a white solid.

Synthesis of Compound 1

A solution of (F) (137.53 g) in DMF (900 mL) was cooled in a NaCl/ice bath to −2° C. HBTU (138.06 g), HOBT (55.90 g), (F) (90.00 g) and ice cold DMF (180 mL) were then added to the solution followed by addition of neat DIEA (67.19 g, 509.66 mmol) via a dropping funnel at a rate such that the internal temperature remained at −0° C. After two hours, neat isopropylethylamine (24.0 g) was added via a dropping funnel. The mixture was stirred at 0° C. until conversion >99%. The reaction mixture was then transferred portionwise into a dropping funnel and slowly added to an ice cold half-saturated NaHCO₃ solution (3.6 L) (internal temperature maintained at 20° C.). The resulting slurry was stirred with a mechanical stirrer for 30 minutes and the solids were then filtered and the filter cake washed with ice cold water (2×1350 mL). The solids were then dissolved in dichloromethane (2.7 L) and the organic phase was extracted with water (portions of 2700 mL) until relative percent area for HOBt/HBTU was <15% by HPLC (200 μL solution for HPLC sample). The organic phase was filtered through a plug of sodium sulfate and subsequently inline filtered through a pad of active charcoal.

The organic phase was concentrated under reduced pressure and methylethyl ketone (1350 mL) was added and the solution concentrated again under reduced pressure. Methylethyl ketone (1350 mL) was then added and the solution concentrated again under reduced pressure. The resulting concentrated solution was cooled to 0° C. until solids were formed; then the mixture was heated to 75° C. as more methylethyl ketone was added (ca. 750 mL) until complete dissolution. The solution was cooled to 65° C. and seeded and the resulting solution/slurry was cooled at a rate of 0.5° C./minute to 20° C. (stir rate of 60-70 rpm). The slurry was stirred for a minimum of 5 hours at 20° C. to allow for complete crystallization. The solids were filtered off and washed with ice cold methylethyl ketone (720 mL) and the filter cake was dried under a stream of nitrogen for 1 hour. The solids were transferred into a round bottom flask and dried under reduced pressure to constant weight to yield 116 g of crystalline compound 1.

Example 11

Methanol (200 mL) was added to crude Compound 1 and the mixture was concentrated to 100 mL. Additional methanol (275 mL) was added, along with deionized water (75 mL), and the mixture concentrated to 400 mL. The clear solution was then seeded with pure crystalline Compound 1, stirred and allowed to slowly evaporate under a stream of compressed air to 200 mL. The resulting yellowish solid was washed with deionized water (400 mL) and 1:1 deionized water-methanol (300 mL) until it turned white and filtrate turned clear. Compound 1 was then dried under vacuum for 12 hours.

The resulting compound 1 (17.3 g) was completely dissolved in methanol (275 mL) by stirring and heating in oil bath (bath set at 85° C.; mixture temperature less than 65° C.). Deionized water (75 mL) was added dropwise over 15 minutes, and the clear mixture was allowed to cool to room temperature. Seed crystals of compound 1 were added to the stirred solution, and the mixture was allowed to slowly concentrate under a stream of compressed air to approximately 250 mL over 9 hours. The crystals were then filtered and washed with 1:1 deionized water-methanol (300 mL). The white solid was dried under vacuum for 12 hours at 22° C. to yield crystalline compound 1 (14.0 g).

Example 12

Crude compound 1 (12.1 g) was completely dissolved in methanol (50 mL) by stirring and heating in oil bath (bath set at 85° C.; mixture temperature less than 65° C.). The clear solution was allowed to cool to room temperature and seed crystals of compound 1 were added to the solution. The mixture was allowed to crystallize over three hours at room temperature. The resulting solid was washed with 1:1 deionized water-methanol (500 mL), filtered, and dried under vacuum for 12 hours to yield crystalline compound 1 (9.4 g).

Example 13

Synthesis of (F)

A flask was charged with (H) (1 g) and ethyl acetate (20 mL) and the solution was cooled in an ice bath for 15 minutes with stirring. Trifluoroacetic acid (10 mL) was then added dropwise, while maintaining an internal temperature of less than 3° C. After stirring at 0° C. for 2 hours, the reaction was allowed to warm to ambient temperature and was stirred for two additional hours. The solution was then evaporated under reduced pressure to a thick colorless oil. This crude mixture was swirled gently with 10 mL of diethyl ether and as the solution was swirled, fine crystals formed. After 30 minutes at ambient temperature, the flask was capped tightly and placed in the freezer overnight. The resulting crystalline solid was filtered and washed with ice cold diethyl ether, and then dried on high vacuum to a constant weight to give fine white crystals of (F) (670 mg).

Example 14

Synthesis of Compound 1

Compound (E) (14.2 g), HBTU (14.3 g), HOBT (5.1 g) and DMF (300 mL), were added to (F) and the mixture was stirred at room temperature to complete dissolution. The reaction was cooled in ice bath for 15 minutes, and DIEA (32 mL) was added over 15 minutes while maintaining an internal temperature of less than 10° C. The reaction mixture was then stirred at 0° C. for one hour before it was quenched with saturated sodium bicarbonate (200 mL). The mixture was extracted with ethyl acetate (1.5 L), and the organic layer was washed with saturated sodium bicarbonate (2×300 mL) and deionized water (1×200 mL). The combined aqueous wash was extracted with ethyl acetate (200 mL) and the organic layers were combined (1.7 L).

The combined organic layers (1.7 L) were concentrated under reduced pressure to 100 mL followed by addition of methanol (200 mL), and the mixture was again concentrated to 100 mL. Additional methanol (200 mL) was added, deionized water (75 mL) was slowly added with stirring, and the mixture concentrated to 300 mL. The clear solution was seeded with crystalline compound 1, stirred and allowed to slowly concentrate under a stream of compressed air to about 200 mL. The off-white solid was washed until solid turned white and filtrate turned clear with a 4:1 deionized water-methanol (2 L) and 1:1 deionized water-methanol (500 mL). The resulting solid was dried under vacuum for 12 hours at 22° C. to provide compound 1 (16.8 g).

Compound 1 was completely dissolved in ethanol (200 mL) by stirring and heating in oil bath (bath set at 85° C.; mixture temperature less than 65° C.). The clear solution was allowed to cool to room temperature and seed crystals of compound 1 were added to the stirred solution, and the mixture was flushed with air and allowed to crystallize. The mixture was then filtered, washed with 1:1 deionized water-ethanol (200 mL), and dried under vacuum for 12 hours at room temperature to yield 10.2 g of crystalline compound 1.

Example 15

Synthesis of (F)

A 500 mL flask was equipped with a mechanical stirrer, thermocouple, cooling bath. (G) (12.5 g) was dissolved in ethyl acetate (125 mL) and the clear solution was cooled to 0-5° C. followed by slow addition of trifluoroacetic acid (375 mL) such that the internal temperature was maintained below 10° C. After warming to room temperature, 5% Pd/C (1.25 g) was added and the reaction mixture under an atmosphere of hydrogen for 2 hours. The reaction mixture was filtered through a glass fiber and rinsed with ethyl acetate (50 mL). The filtrate was then concentrated under reduced pressure to yield a yellow oil. MTBE (50 mL) was added to the oil and co-evaporated to yellow oil at 25° C. MTBE (60 mL) was again added and the mixture was cooled to −10° C. and stirred for 60 minutes. Heptanes (120 mL) were then slowly added to the stirred mixture and stirring was continued at −10° C. for an additional 15 minutes. The solids were collected by filtration and the crystals were rinsed with heptanes (2×40 mL) and dried under high vacuum at room temperature (22° C.) to a constant weight (10.1 g).

Synthesis of Compound 1

A flask equipped with a mechanical stirrer, thermocouple, cooling bath, nitrogen inlet and drying tube was charged with DMF, (F) (133.9 g), (E) (241.8 g), HBTU (242.8 g), and HOBT (86.5 g) and the mixture was stirred and cooled to 0-5° C. DIEA (156 mL) was then added slowly over at least 30 minutes, while maintaining temperature between 0-5° C. The reaction mixture was stirred at 0-5° C. for one hour and was then poured into a vigorously stirred saturated solution of sodium bicarbonate (3630 mL) and ethyl acetate (900 mL). Additional ethyl acetate (2000 mL) was added to extract the product and the organic layer was separated. The aqueous layer was then extracted with ethyl acetate (1930 mL). The organic phases were combined and washed with saturated solution of sodium bicarbonate (2420 mL) and brine (2420 mL), dried over magnesium sulfate (360 g), filtered through glass fiber filter and rinsed with ethyl acetate (2×360 mL).

The resulting solution was concentrated to a semisolid under reduced pressure and methanol (725 mL) was added and co-evaporated under reduced pressure to yield semi-solid compound 1. The crude product was dissolved in methanol (5320 mL) and the solution was stirred while water (2130 mL) was added over twenty minutes. When addition of water was complete, approximately 0.3 g of pure crystalline seeds were added and the methanol/water solution was stirred for three hours. The resulting crystalline white solid was isolated by filtration and the fine white crystalline product was rinsed with a methanol/water solution (1:1, 1200 mL). The resulting solid was rinsed with methanol/water solution (1:1, 1200 mL) and the crystalline product was poured onto drying tray and dried to a constant weight under high vacuum at 27° C. under nitrogen bleed to yield crystalline compound 1 (230 g).

Example 16

Synthesis of (F)

A 100 mL three-neck round bottom flask was charged with (G) (5 g) and dichloromethane (15 mL). The mixture was stirred until the solids had dissolved, and then placed in an ice bath. After 20 minutes, the internal temperature had reached 0.6° C. and trifluoroacetic acid was added dropwise over 5 min. After the addition was complete, the flask was allowed to warm to room temperature. After 2 hours, MTBE was added to the flask (35 mL) and the mixture was cooled in an ice bath, wherein (F) began to crystallize during cooling. Heptanes (65 mL) were then added to the flask dropwise over 15 min and the flask was placed in the freezer (−5° C.). After 1 hour, the solid white product was collected and washed with heptanes (10 mL) to provide 4.57 g of (F).

Example 17

Synthesis of Compound 1 Citrate Salt

Compound 1 (10 g) and citric acid (2.7 g) were dissolved in THF (75 mL) and acetonitrile (50 mL). The solution was then stirred for 2 hours at room temperature, at which time a white precipitate formed. The flask was then cooled to −10° C. and stirred overnight. The solids were filtered and washed with 100 mL acetonitrile to give 11.52 g of the citrate salt of compound 1.

Example 18

Synthesis of (H) and (Q)

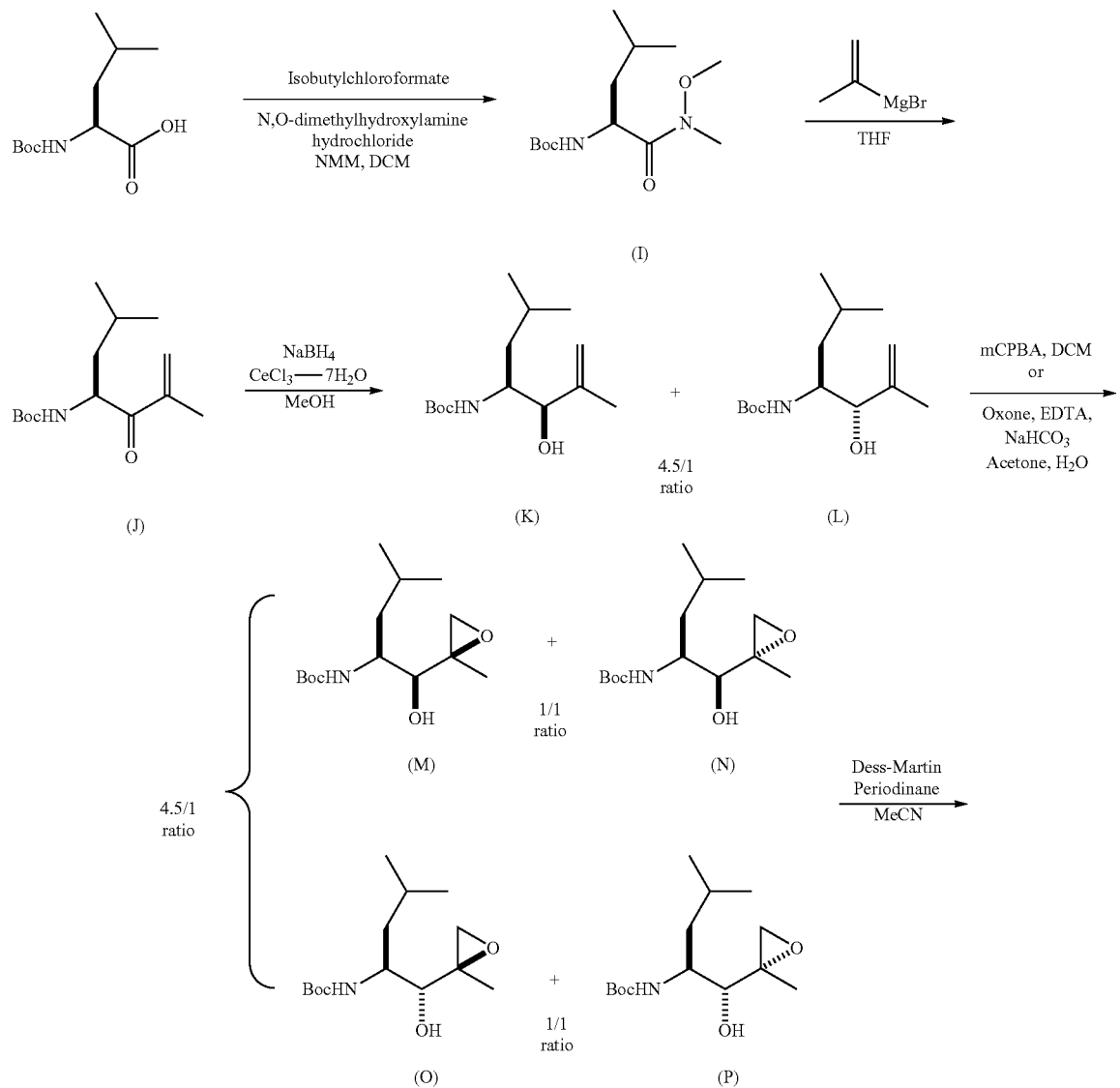

-continued

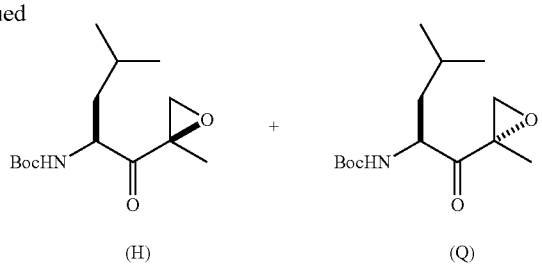

(H)          (Q)

Synthesis of (I)

A suspension of dimethyl hydroxylamine hydrochloride (10.53 g, 108 mmol) in DCM (270 mL) under an atmosphere of argon was stirred vigorously for 0.5 hours followed by addition of TEA (10.92 g, 14.75 mL, 108 mmol) via addition funnel. A solution of Boc-Leucine-OH (25.0 g, 108 mmol) in DCM (270 mL) was cooled to 0° C. followed by dropwise addition of isobutylchloroformate (14.73 g, 13.98 mL, 108 mmol) via addition funnel. The mixture was further cooled to −20° C. and NMM (10.92 g, 11.87 mL, 108 mmol) was added via addition funnel at such a rate to maintain the internal temperature below −10° C. After stirring for 5 minutes at −20° C., the previously prepared dimethylhydroxylamine solution was added via a wide bore Teflon cannula. The reaction mixture was removed from the cooling bath and allowed to warm to room temperature overnight. The mixture was then diluted with water (100 mL) and stirred for 15 minutes. The layers were separated and the aqueous layer extracted with DCM (2×50 mL). The organic layers were combined, washed with 1 N HCl (4×150 mL), water (1×150 mL), sat. NaHCO$_3$ (2×100 mL), brine (1×250 mL) and dried over Na$_2$SO$_4$. The Na$_2$SO$_4$ was removed by filtration and the volatiles removed under reduced pressure to give (I) (28.05 g, 102 mmol).

Synthesis of (J)

To a 0° C. solution of (I) (10.0 g, 36.4 mmol,) in 100 mL of dry THF, under an atmosphere of argon was added isopropenyl magnesium bromide (364 mL, 182 mmol, 5.0 eq, 0.5 M solution in THF) dropwise using an addition funnel. The rate of addition was adjusted such that the internal reaction temperature was maintained below 5° C. After six hours the reaction mixture was poured into 250 mL of sat. NH$_4$Cl and 500 mL wet ice. After stirring for 30 minutes the mixture became clear and the volatiles were removed under reduced pressure and the crude material diluted with EtOAc (200 mL). The layers were separated and the aqueous layer extracted with EtOAc (3×150 mL), the organic layers were combined, washed with water (2×150 mL), brine (2×150 mL) and dried over MgSO$_4$. The MgSO$_4$ was removed by filtration and the volatiles removed under reduced pressure. Purification by flash chromatography (15:1 hexanes/EtOAc) gave (J) as a solid (7.5 g, 29.37 mmol).

Synthesis of (K) and (L)

To a 0° C. solution of (J) (5.0 g, 19.58 mmol) in 200 mL of MeOH was added CeCl$_3$-7H$_2$O (8.75 g, 23.50 mmol). The solution was stirred under an atmosphere of argon until the CeCl$_3$-7H$_2$O was completely dissolved. To this solution was added NaBH$_4$ (0.88 g, 23.50 mmol) in 10 portions over 2 minutes. The reaction was then stirred under an atmosphere of argon at 0° C. for 6 hours. The reaction was quenched at 0° C. with approximately 2.5 mL of glacial HOAc and after 30 minutes of additional stirring at 0° C. the mixture become clear. The volatiles were removed under reduced pressure and the remaining oil taken up in EtOAc (200 mL). The organic layer was washed with water (2×100 mL), brine (2×100 mL) and dried over MgSO$_4$. The MgSO$_4$ was removed by filtration and the volatiles removed under reduced pressure giving (K) and (L) as a waxy, white solid (4.75 g, 18.5 mmol). Ratio of diastereomers 4.5:1 as determined by HPLC.

Synthesis of (M), (N), (O) and (P)

To a solution of (K) and (L) (0.025 g, 0.097 mmol) in DCM (1 mL) was added mCPBA (0.018 g, 0.107 mmol). The mixture was stirred at room temperature for one hour at which time the mixture was diluted with sat. NaHCO$_3$ (5 mL). The layers were separated and the aqueous layer extracted with DCM (2×2 mL). The organic layers were combined and washed with water (2×5 mL), brine (2×5 mL) and dried over MgSO$_4$. The MgSO$_4$ was removed by filtration and the volatiles removed under reduced pressure to give an oil.

Synthesis of (H) and (Q)

To a solution of Dess-Martin Periodinane (0.023 g, 0.055 mmol) in 1 mL MeCN at 5° C. was added a mixture of (M), (N), (O), and (P) (0.010 g, 0.037 mmol) as a solution in MeCN (1 mL). The mixture was placed under an atmosphere of argon and allowed to warm to room temperature while stirring overnight. When complete, a white precipitate had formed and the reaction was cooled in an ice-bath and diluted with 2 mL sat. NaHCO$_3$. The mixture was diluted with 10 mL of EtOAc and the solids removed by filtering through a plug of Celite. The mixture was transferred to a separatory funnel and the layers separated. The aqueous layer was extracted with EtOAc (2×5 mL) and the organic layers combined, washed with water (3×5 mL) and brine (1×10 mL) and then dried over Na$_2$SO$_4$. The Na$_2$SO$_4$ was removed by filtration and the volatiles removed under reduced pressure to give a mixture of (H) and (Q) as a light, yellow oil.

Example 19

Alternate Synthesis of (H) and (Q)

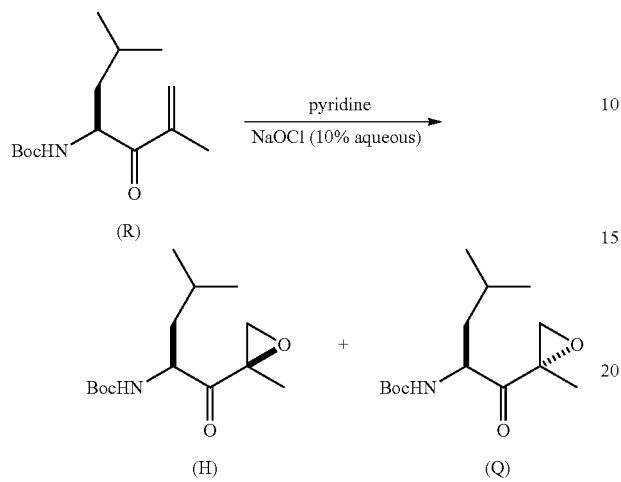

Alternate Synthesis of (H) and (Q)

To a −5° C. solution of (R) (0.200 g, 0.78 mmol) in pyridine (3 mL) was added 10% aqueous NaOCl (1.5 mL) dropwise at a rate such that the internal reaction temperature remained below −4° C. After the addition of NaOCl was complete, the reaction flask was placed in a 0° C. bath and stirred for two hours. The mixture was then diluted with EtOAc (10 mL), washed with water (2×10 mL), brine (2×10 mL) and dried over $Na_2SO_4$. The $Na_2SO_4$ was removed by filtration and the volatiles removed under reduced pressure to give the crude mixture of (H) and (Q). Purification by flash chromatography (20:1 hexanes/EtOAc) gave (H) as an oil (0.059 g, 0.216 mmol) and (Q) as a solid (0.023 g, 0.085 mmol).

Example 20

Synthesis of Compound 1

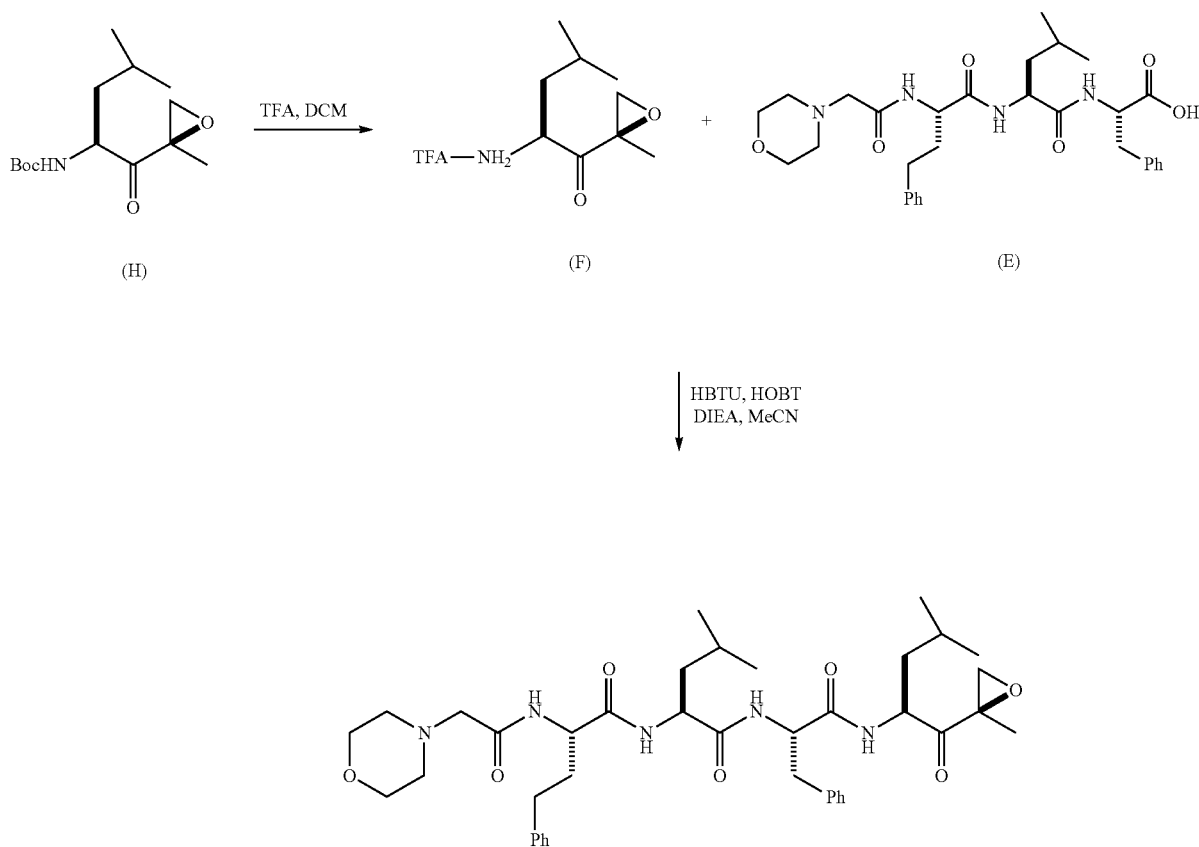

Synthesis of (F)

To a 10 mL round bottomed flask was added (H) (0.050 g, 0.18 mmol) and DCM (0.80 mL). The mixture was cooled to 0° C. and neat TFA (0.20 mL) was added dropwise. After the addition of TFA was complete the flask was allowed to warm to room temperature while stirring for one hour. The volatiles were then removed under reduced pressure and the resulting oil was chased with DCM (2 mL×2) and the volatiles removed under reduced pressure.

Synthesis of Compound 1

To a 10 mL round bottomed flask containing (F) was added (E) (0.085 g, 0.15 mmol), MeCN (2.0 mL), HOBT (0.031 g, 0.23 mmol), and HBTU (0.087 g, 0.23 mmol) and the mixture was cooled to 0° C. To this mixture was slowly added DIEA (0.077 g, 0.104 mL, 0.6 mmol) and the mixture was allowed to stir at 0° C. for one hour before quenching with saturated NaHCO$_3$ (5 mL). The mixture was diluted with EtOAc (15 mL) and the layers were separated. The organic layer was washed with saturated NaHCO$_3$ (3×5 mL), brine (2×5 mL) and dried over Na$_2$SO$_4$. The Na$_2$SO$_4$ was removed by filtration and the volatiles removed under reduced pressure to give a thick oil. To the flask containing the oil was added DCM (1 mL) and the placed under high vacuum while swirling giving Compound 1 (0.100 g, 0.14 mmol) as a foam.

Example 21

Synthesis of Compound 1

Alternate Synthesis of (S)

To a 10 mL round bottomed flask was added (G) (0.055 g, 0.18 mmol), formic acid (2 mL), and Pd/C (5% wt, 0.05 g). Once the deprotection was deemed complete by TLC and LCMS, the volatiles were removed under reduced pressure. The oil was chased with DCM (2 mL×2) and the volatiles removed under reduced pressure.

Synthesis of Compound 1

To a 10 mL round bottomed flask containing (S) was added (E) (0.085 g, 0.15 mmol), MeCN (2.0 mL), HOBT (0.031 g, 0.23 mmol), HBTU (0.087 g, 0.23 mmol) and the mixture was cooled to 0° C. To this mixture was slowly added DIEA (0.077 g, 0.104 mL, 0.6 mmol). The mixture was then allowed to stir at 0° C. for 60 minutes and was quenched by the addition of saturated NaHCO$_3$ (5 mL). The mixture was diluted with EtOAc (15 mL) and the layers separated. The organic layer was washed with saturated NaHCO$_3$ (3×5 mL), brine (2×5 mL) and dried over Na$_2$SO$_4$. The Na$_2$SO$_4$ was removed by filtration and the volatiles removed under reduced pressure to give a thick oil. To the flask containing the oil was added DCM (1 mL) and the mixture placed under high vacuum while swirling giving Compound 1 as a foam.

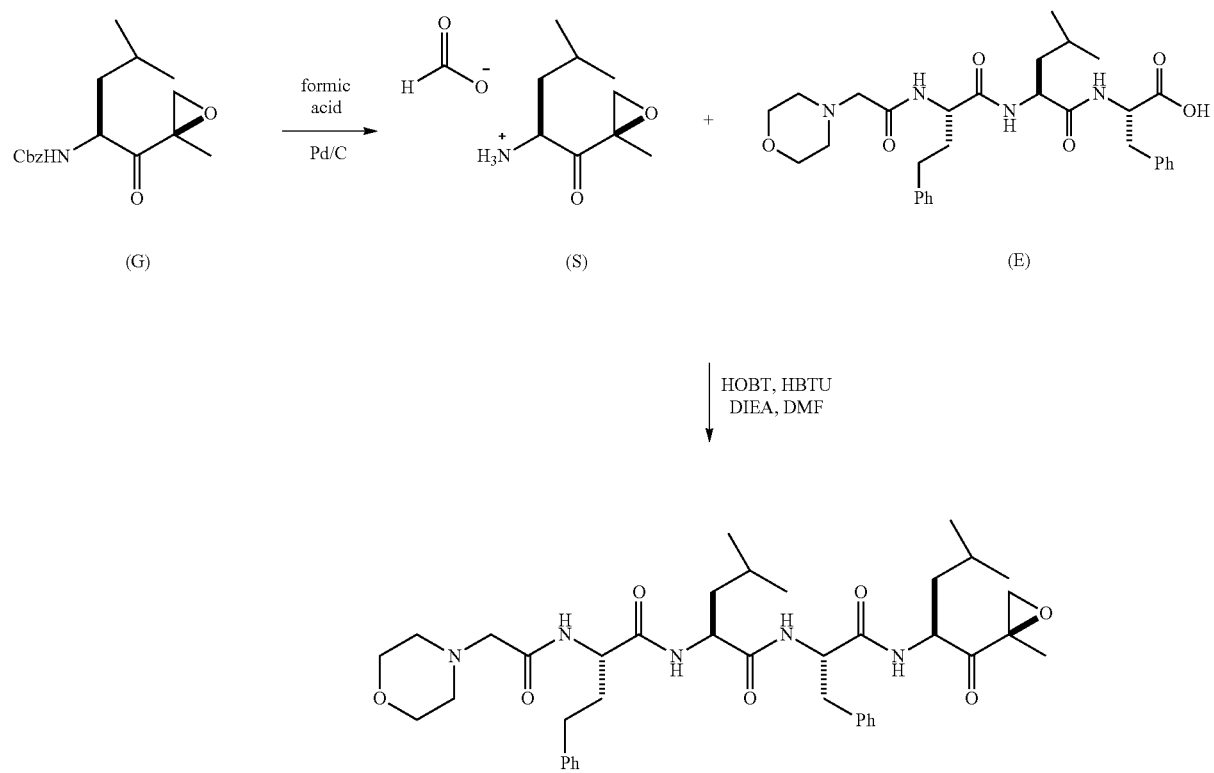

Example 22

Synthesis of (H)

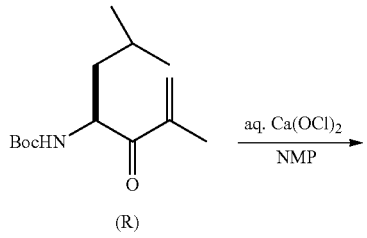

(R)

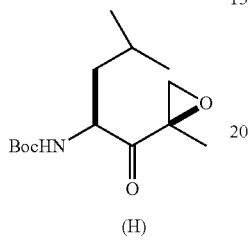

(H)

Water (214 mL) was added to a three neck flask equipped with a mechanical stirrer, an addition funnel, and a thermocouple with display and cooled to an internal temperature of −5 to 0° C. Solid calcium hypochlorite (107 g, 748 mmol) was then added over approximately 5 minutes, while the temperature of the mixture is maintained at approximately −5° C. to 0° C. The mixture was then further cooled to −10° C. to −5° C. and stirred for 10 minutes followed by addition of NMP (1000 mL) via addition funnel at a rate to maintain internal temperature between −10° C. to −5° C. The reaction slurry was then stirred at −10° C. for 15 minutes. (R) (47.8 g, 187 mmol) was dissolved in NMP (400 mL) and added dropwise to the reaction mixture while maintaining the internal temperature between −15° C. and −10° C. The reaction mixture was then stirred at −5° C. to 0° C. until the reaction was complete by TLC. Upon reaction completion, the mixture was quenched by slow addition of 1.0 M sodium thiosulfate solution (500 mL), maintaining an internal temperature of −10° C. to −5° C. Ethyl Acetate (1000 mL) was then added, the layers were separated and the aqueous layer was extracted twice more. The combined organic layers were washed with water (500 mL) and brine (500 mL), dried over magnesium sulfate, filtered and concentrated under reduced pressure to a to yellow oil which was dissolved in hexanes (600 mL) and filtered through a plug of silica to provide (H) as a pale yellow oil (20.8 g).

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A method for preparing a crystalline salt of a compound of Formula (II)

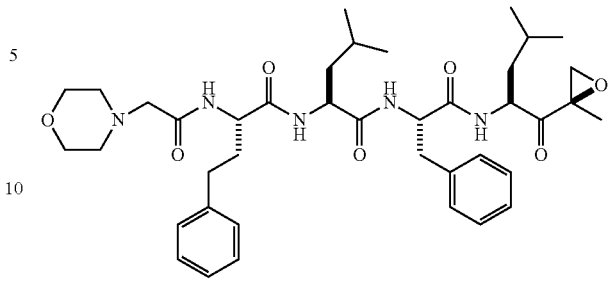

wherein the salt is a citrate salt; and the method comprises (i) preparing a solution of a compound of Formula (II) in an organic solvent; (ii) adding citric acid; (iii) bringing the solution to supersaturation to cause formation of crystals; and (iv) isolating the crystals, wherein said crystalline compound has 2θ values of 4.40; 7.22; 9.12; 12.36; 13.35; 14.34; 15.54; 16.14; 16.54; 17.00; 18.24; 18.58; 19.70; 19.90; 20.30; 20.42; 21.84; 22.02; 23.34; 23.84; 24.04; 24.08; 24.48; 24.76; 25.48; 26.18; 28.14; 28.20; 28.64; 29.64; 31.04; 31.84; 33.00; 33.20; 34.06; 34.30; 34.50; 35.18; 37.48; 37.90; and 39.48.

2. A method of claim 1, wherein the organic solvent is selected from diethyl ether, THF, acetonitrile, and MTBE, or any combination thereof.

3. A method of claim 2, wherein the organic solvent is a mixture of THF and acetonitrile.

4. A method of claim 1, wherein bringing the solution to supersaturation comprises slow addition of an anti-solvent, allowing the solution to cool, reducing the volume of the solution, or any combination thereof.

5. A method of claim 4, wherein bringing the solution to supersaturation comprises cooling the solution to ambient temperature or lower.

6. A method of claim 1, further comprising washing the crystals.

7. A method of claim 6, wherein the washing comprises washing with a liquid selected from diethyl ether, THF, acetonitrile, and MTBE, or any combination thereof.

8. A method of claim 7, wherein washing comprises washing with acetonitrile.

9. A method of claim 1, wherein isolating the crystals comprises filtering the crystals.

10. A method of claim 1, further comprising drying the crystals under reduced pressure.

11. A crystalline salt of a compound having a structure of Formula (II)

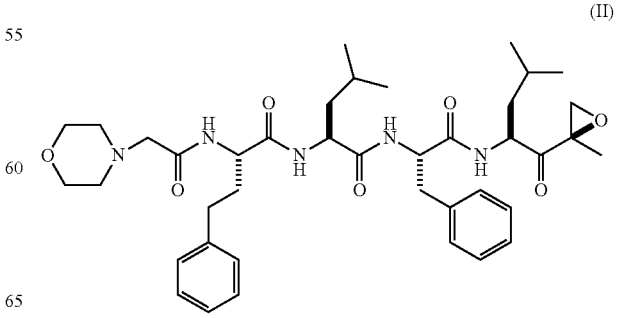

wherein the salt is a citrate salt, and wherein said crystalline compound has 2θ values of 4.40; 7.22; 9.12; 12.36; 13.35; 14.34; 15.54; 16.14; 16.54; 17.00; 18.24; 18.58; 19.70; 19.90; 20.30; 20.42; 21.84; 22.02; 23.34; 23.84; 24.04; 24.08; 24.48; 24.76; 25.48; 26.18; 28.14; 28.20; 28.64; 29.64; 31.04; 31.84; 33.00; 33.20; 34.06; 34.30; 34.50; 35.18; 37.48; 37.90; and 39.48.

12. A crystalline salt of claim 11, having a DSC thermogram substantially as shown in FIG. 11.

13. A crystalline salt of claim 11, having a melting point of about 180 to about 190° C.

14. A crystalline salt of claim 13, having a melting point of about 184 to about 188° C.

15. A crystalline salt of claim 11, having an XRPD pattern substantially as shown in FIG. 12.

* * * * *